US012492208B2

(12) United States Patent
Nakamura et al.

(10) Patent No.: US 12,492,208 B2
(45) Date of Patent: Dec. 9, 2025

(54) CRYSTAL OF PYRIMIDINE COMPOUND

(71) Applicant: TAIHO PHARMACEUTICAL CO., LTD., Tokyo (JP)

(72) Inventors: Hiroyuki Nakamura, Ibaraki (JP); Hiroyoshi Yamanaka, Ibaraki (JP); Takahiro Asai, Ibaraki (JP)

(73) Assignee: TAIHO PHARMACEUTICAL CO., LTD., Tokyo (JP)

( * ) Notice: Subject to any disclaimer, the term of this patent is extended or adjusted under 35 U.S.C. 154(b) by 443 days.

(21) Appl. No.: 18/015,997

(22) PCT Filed: Jul. 14, 2021

(86) PCT No.: PCT/JP2021/026460
§ 371 (c)(1),
(2) Date: Jan. 13, 2023

(87) PCT Pub. No.: WO2022/014638
PCT Pub. Date: Jan. 20, 2022

(65) Prior Publication Data

US 2023/0331730 A1 Oct. 19, 2023

(30) Foreign Application Priority Data

Jul. 15, 2020 (JP) ................................ 2020-121520

(51) Int. Cl.
*C07D 487/04* (2006.01)
*A61K 9/00* (2006.01)
*A61P 35/00* (2006.01)

(52) U.S. Cl.
CPC .......... *C07D 487/04* (2013.01); *A61K 9/0053* (2013.01); *A61P 35/00* (2018.01); *C07B 2200/13* (2013.01)

(58) Field of Classification Search
None
See application file for complete search history.

(56) References Cited

U.S. PATENT DOCUMENTS 11,078,207 B2 * 8/2021 Nakamura .............. A61P 35/00
2010/0144705 A1 6/2010 Miller
(Continued)

FOREIGN PATENT DOCUMENTS

EP 3 590 516 A1 1/2020
WO WO 2010/065898 A2 6/2010
(Continued)

OTHER PUBLICATIONS

Abdallah et al., "Brain metastases in non-small-cell lung cancer: are tyrosine kinase inhibitors and checkpoint inhibitors now viable options?", Current Oncology, Jun. 2018, vol. 25, Supp. 1, pp. S103-S114.
(Continued)

*Primary Examiner* — Jeffrey S Lundgren
*Assistant Examiner* — Anthony Joseph Seitz
(74) *Attorney, Agent, or Firm* — Birch, Stewart, Kolasch & Birch, LLP

(57) ABSTRACT

A crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (compound (I)), and a crystal thereof with an acid (salt crystal or co-crystal) are provided.

There are provided: a type II crystal of compound (I) with fumaric acid, having characteristic peaks at three or more diffraction angles (2θ±0.2°) selected from 5.5°, 6.8°, 9.3°, 13.4°, 15.3°, 16.3°, 18.5°, 19.8°, 22.0°, and 24.5° in a powder X-ray diffraction spectrum;

a (free-form) type II crystal of compound (I) having characteristic peaks at three or more diffraction angles selected from 8.3°, 14.8°, 17.3°, 18.0°, 19.1°, 20.3°, 21.0°, 22.5°, 23.0°, and 26.2° in a powder X-ray diffraction spectrum;

a (free-form) type I crystal of compound (I) having characteristic peaks at three or more diffraction angles (Continued)

Powder X-ray diffraction spectrum of type II crystal of compound (I) with 1 equivalent of fumaric acid selected from 9.9°, 11.7°, 13.2°, 17.7°, 18.1°, 18.8°, and 20.8° in a powder X-ray diffraction spectrum;
a type V crystal of compound (I) with fumaric acid, having characteristic peaks at four or more diffraction angles selected from 6.9°, 9.4°, 10.2°, 13.7°, 21.1°, 23.6°, and 26.5° in a powder X-ray diffraction spectrum; and
a type I crystal of compound (I) with fumaric acid, having characteristic peaks at four or more diffraction angles selected from 6.4°, 10.3°, 12.8°, 15.0°, 20.7°, 23.4°, and 26.6° in a powder X-ray diffraction spectrum.

18 Claims, 31 Drawing Sheets

Specification includes a Sequence Listing.

(56) References Cited

U.S. PATENT DOCUMENTS

| | | | |
|---|---|---|---|
| 2017/0217970 | A1 | 8/2017 | Kawai et al. |
| 2021/0024530 | A1 | 1/2021 | Nakamura et al. |
| 2021/0252000 | A1 | 8/2021 | Irie et al. |

FOREIGN PATENT DOCUMENTS

| | | | |
|---|---|---|---|
| WO | WO 2013/118817 | A1 | 8/2013 |
| WO | WO 2017/038838 | A1 | 3/2017 |
| WO | WO 2020/04546 | A1 | 3/2020 |
| WO | WO 2020/145374 | A1 | 7/2020 |

OTHER PUBLICATIONS

Burstein et al., "Neratinib, an Irreversible ErbB Receptor Tyrosine Kinase Inhibitor, in Patients With Advanced ErbB2-Positive Breast Cancer", Journal of Clinical Oncology, Mar. 10, 2010, vol. 28, No. 8, pp. 1301-1307.
Freedman et al., "Translational Breast Cancer Research Consortium (TBCRC) 022: A Phase II Trial of Neratinib for Patients With Human Epidermal Growth Factor Receptor 2—Positive Breast Cancer and Brain Metastases", Journal of Clinical Oncology, Mar. 20, 2016, vol. 34, No. 9, pp. 945-952.
Gomez et al., "Efficacy and Safety of Lapatinib As First-Line Therapy for ErbB2—Amplified Locally Advanced or Metastatic Breast Cancer", Journal of Clinical Oncology, Jun. 20, 2008, vol. 26, No. 18, pp. 2999-3005.
Heffron, "Small Molecule Kinase Inhibitors for the Treatment of Brain Cancer", J. Med. Chem., 2016, vol. 59, pp. 10030-10066.
International Search Report (PCT/ISA/210), issued in PCT/JP2021/026460, dated Aug. 24, 2021.
Kennecke et al., "Metastatic Behavior of Breast Cancer Subtypes", Journal of Clinical Oncology, Jul. 10, 2010, vol. 28, No. 20, pp. 3271-3277.
Lin et al., "Phase II Trial of Lapatinib for Brain Metastases in Patients With Human Epidermal Growth Factor Receptor 2—Positive Breast Cancer", Journal of Clinical Oncology, Apr. 20, 2008, vol. 26, No. 12, pp. 1993-1999.
Witzel et al., "Breast cancer brain metastases: biology and new clinical perspectives", Breast Cancer Research, 2016, vol. 18, No. 8, pp. 1-9.
Written Opinion of the International Searching Authority (PCT/ISA/237), issued in PCT/JP2021/026460, dated Aug. 24, 2021.
Yan et al., "HER2 aberrations in cancer: Implications for therapy", Cancer Treatment Reviews, 2014, vol. 40, pp. 770-780.
English translation of the Written Opinion of the International Searching Authority for International Application No. PCT/JP2021/026460, dated Aug. 24, 2021.
Extended European Search Report for European Application No. 21842747.4, dated Jun. 18, 2024.

* cited by examiner

[Figure 1]
Powder X-ray diffraction spectrum of type II crystal of compound (I) with 1 equivalent of fumaric acid
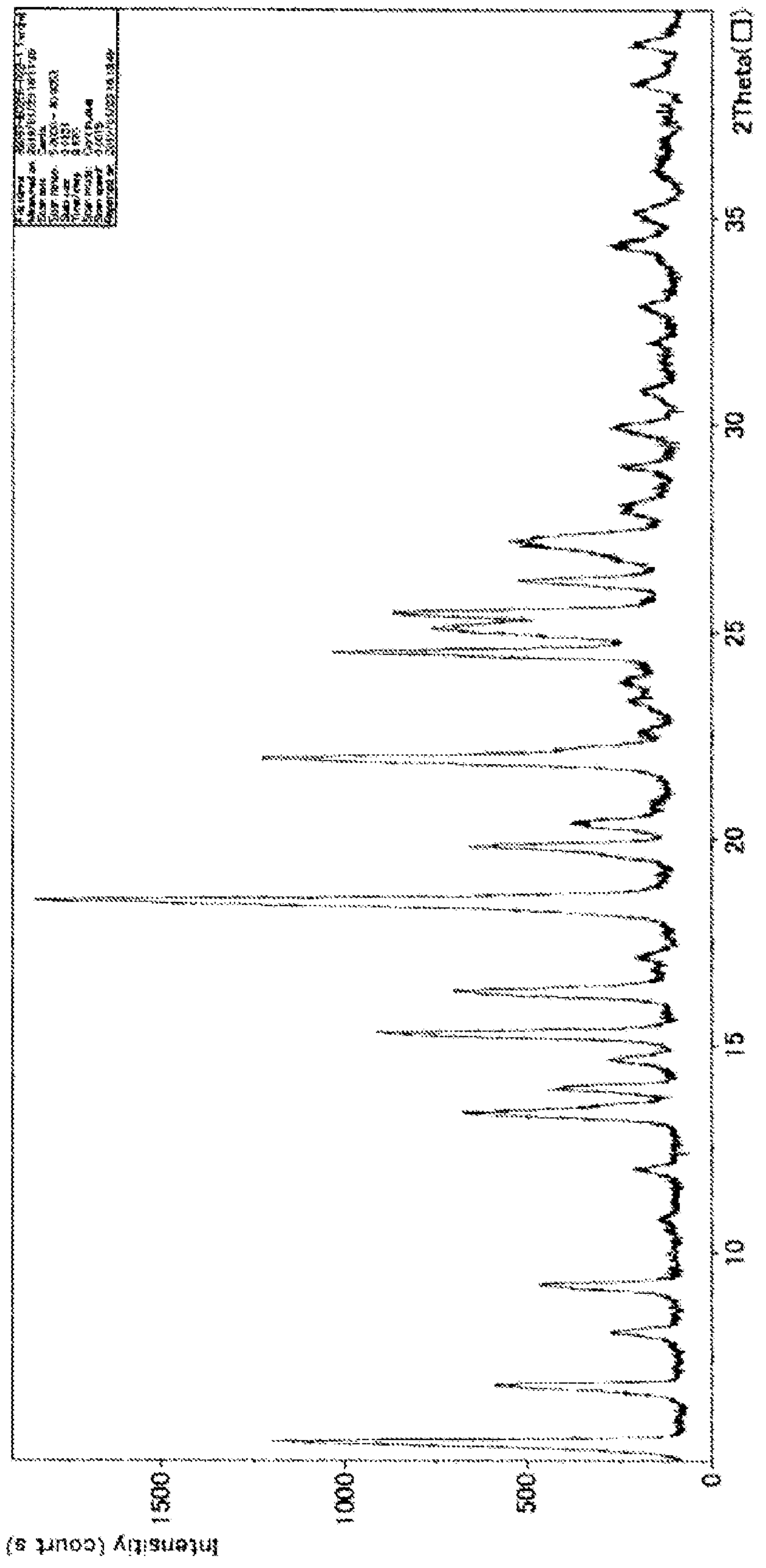

[Figure 2]
Simultaneous thermogravimetry-differential thermal analysis (TG-DTA) of type II crystal of compound (I) with 1 equivalent of fumaric acid
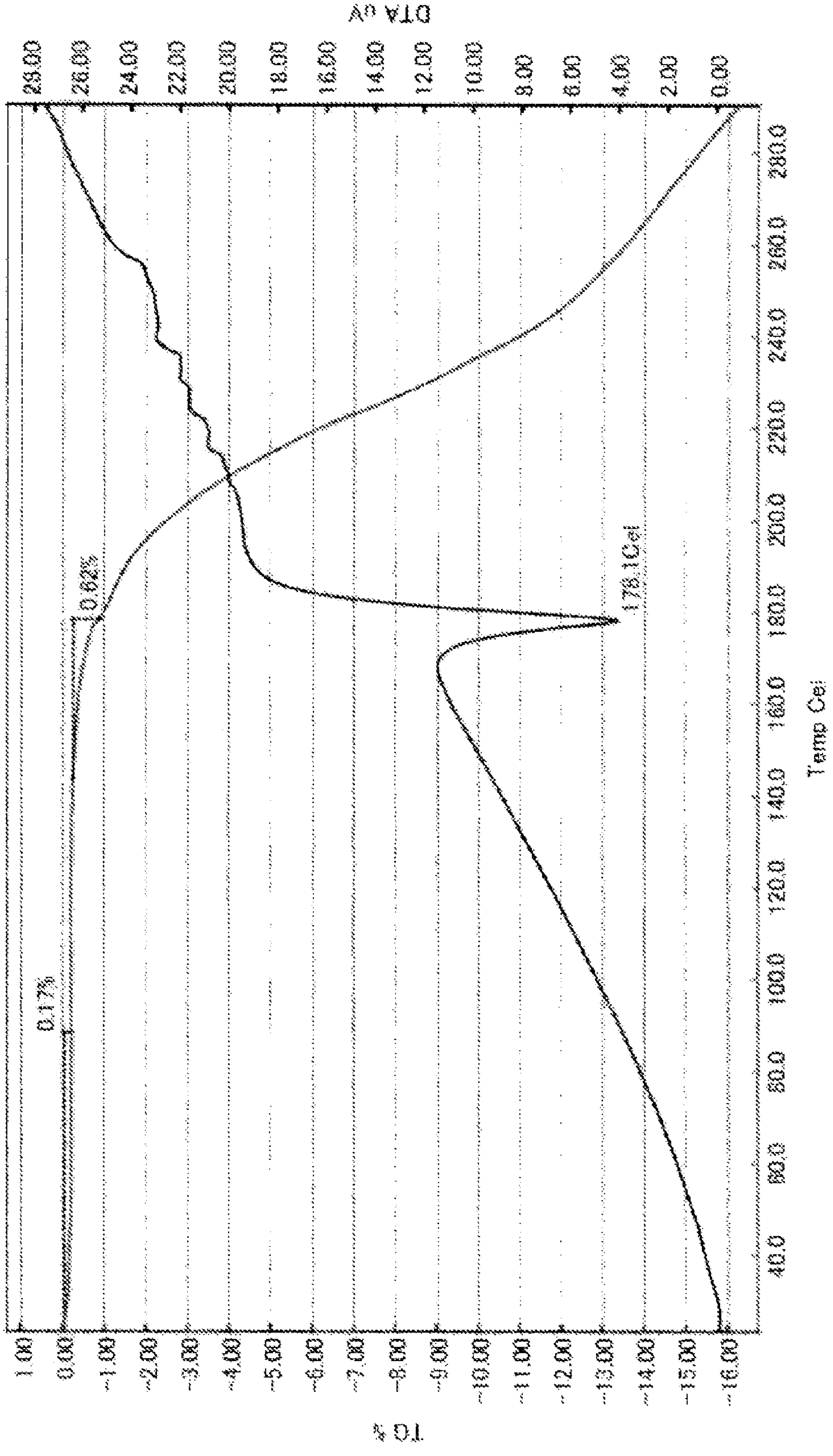

[Figure 3]
Powder X-ray diffraction spectrum of type II crystal of compound (I)
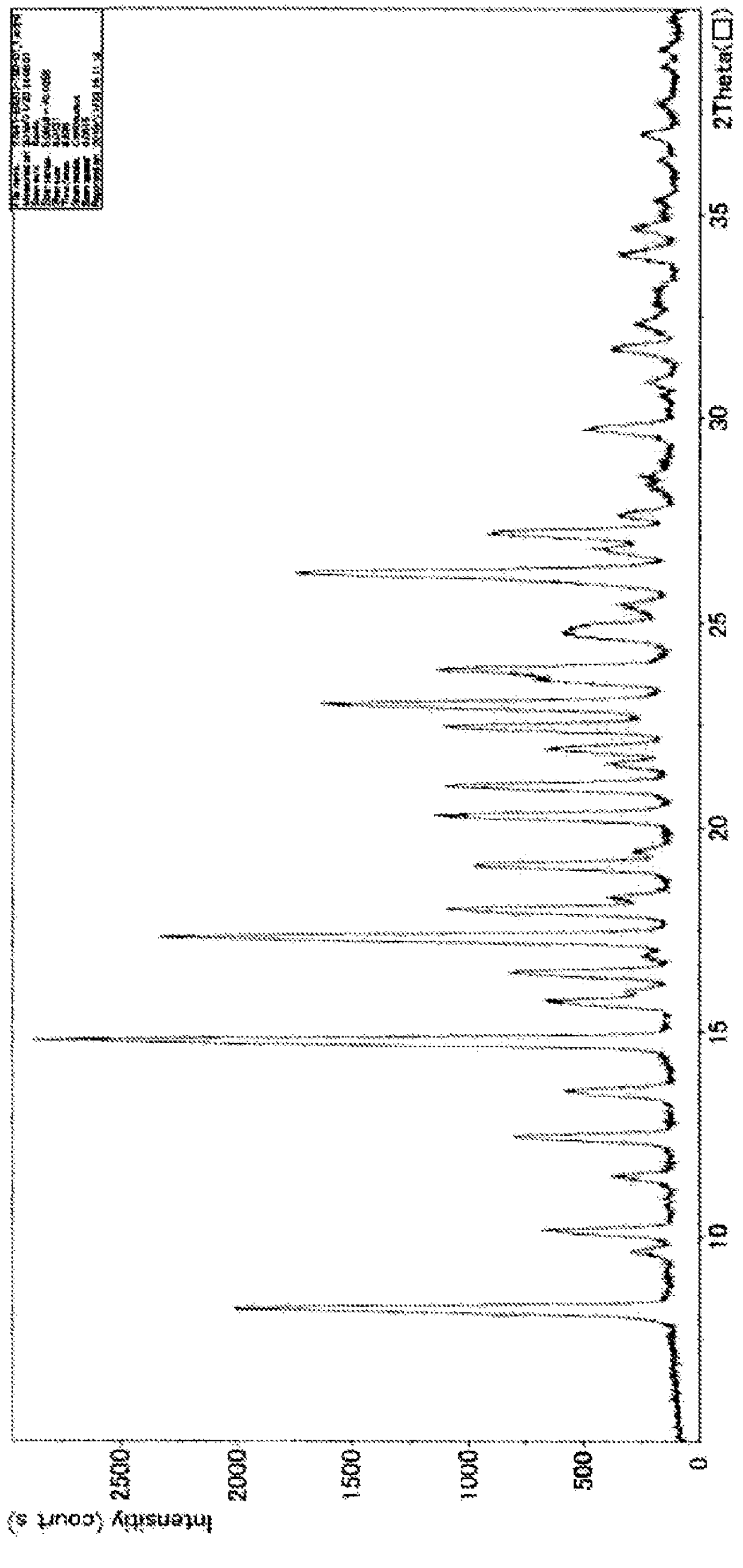

[Figure 4]
Simultaneous thermogravimetry-differential thermal analysis (TG-DTA) of type II crystal of compound (I)
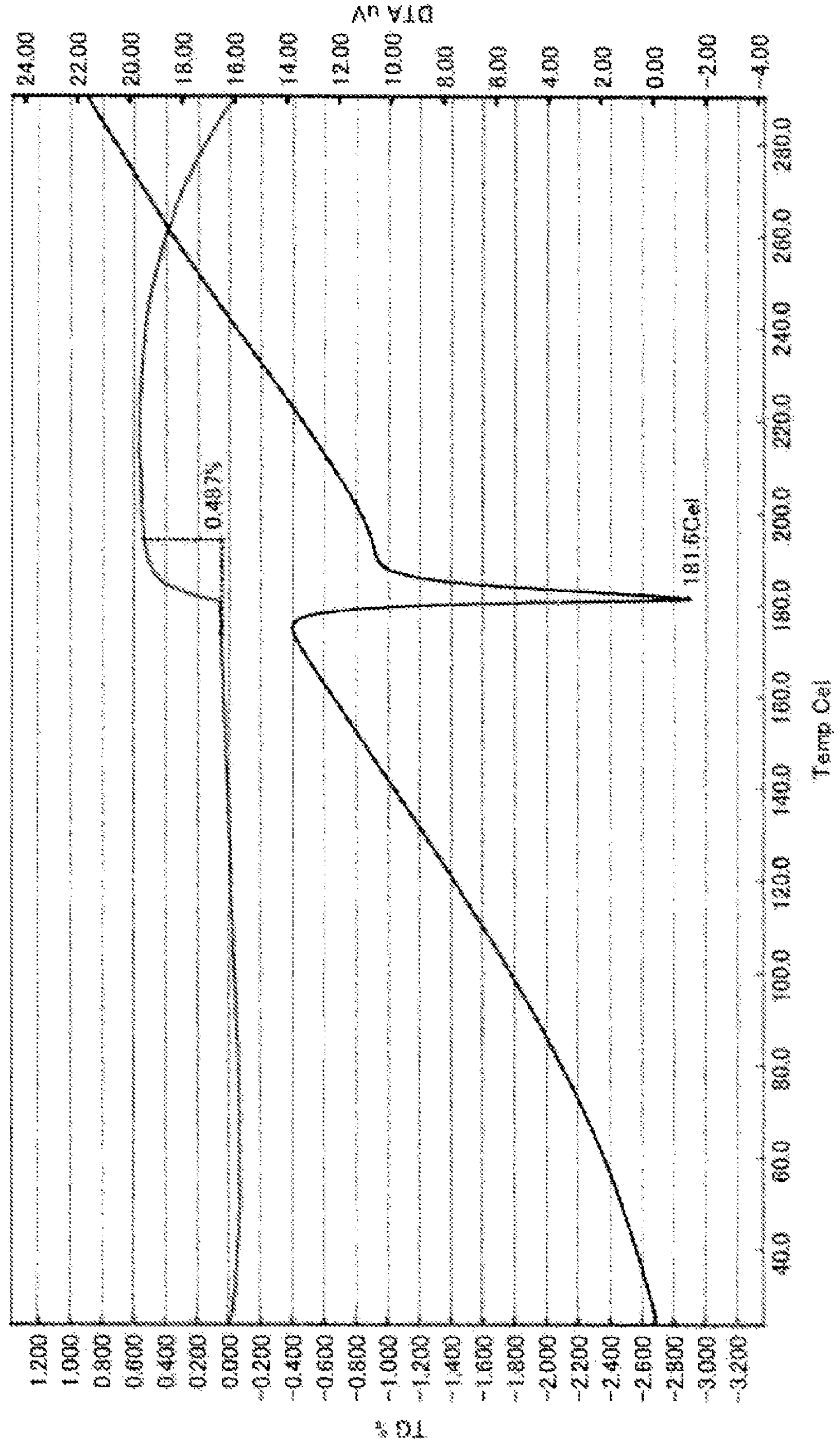

[Figure 5]
Powder X-ray diffraction spectrum of type I crystal of compound (I)
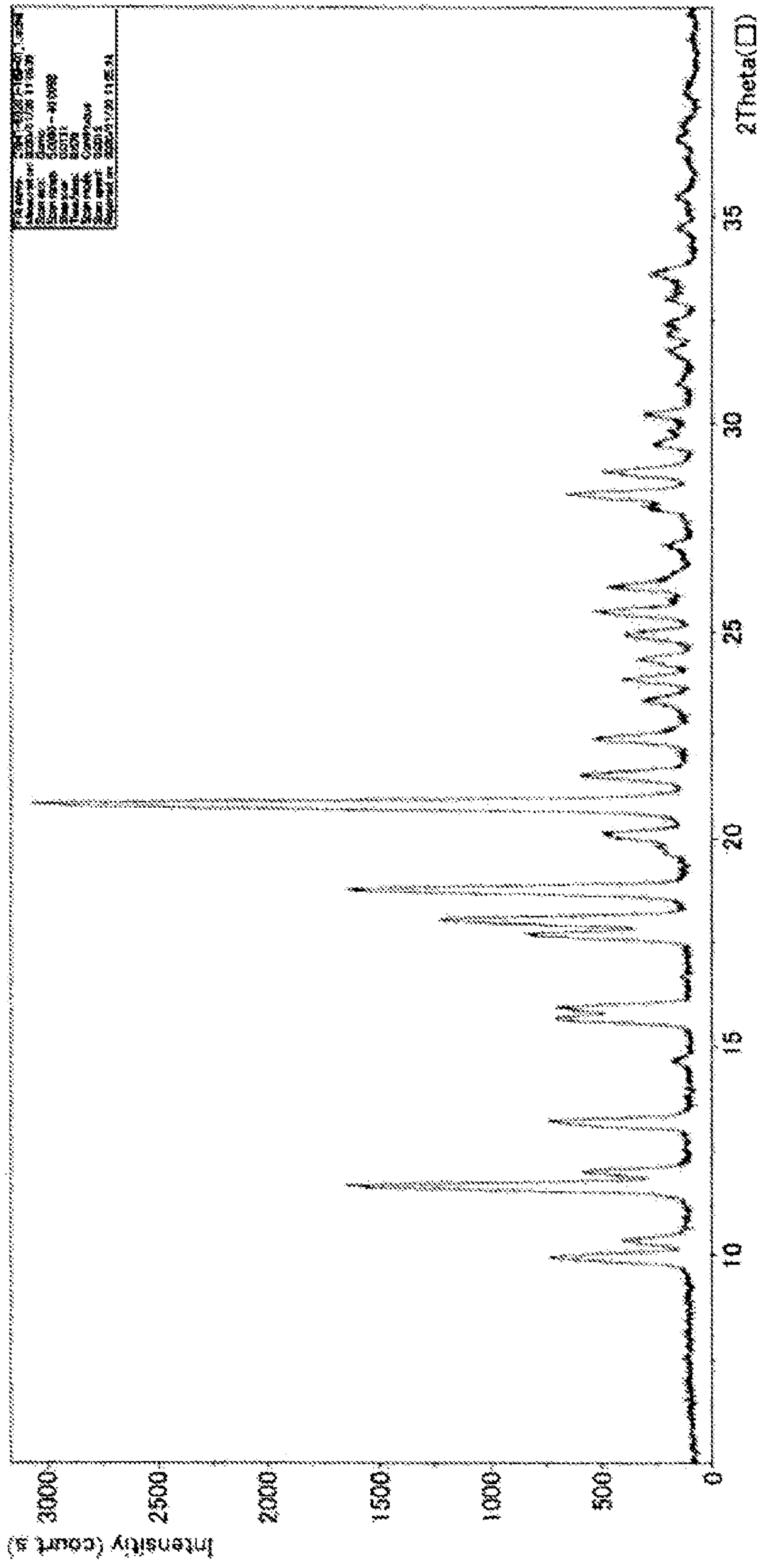

[Figure 6]
Simultaneous thermogravimetry-differential thermal analysis (TG-DTA) of type I crystal of compound (I)
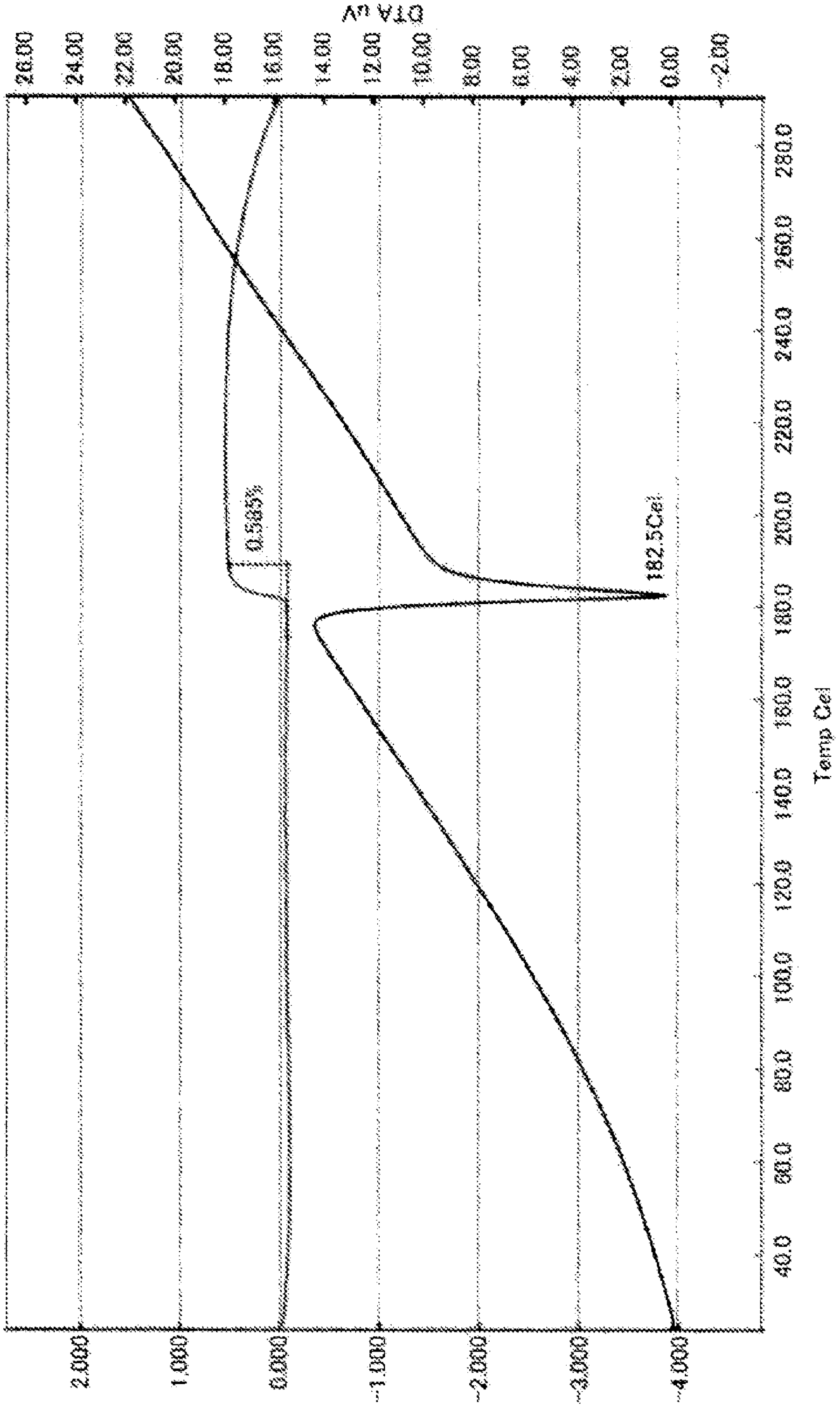

[Figure 7]
Powder X-ray diffraction spectrum of type V crystal of compound (I) with 1 equivalent of fumaric acid
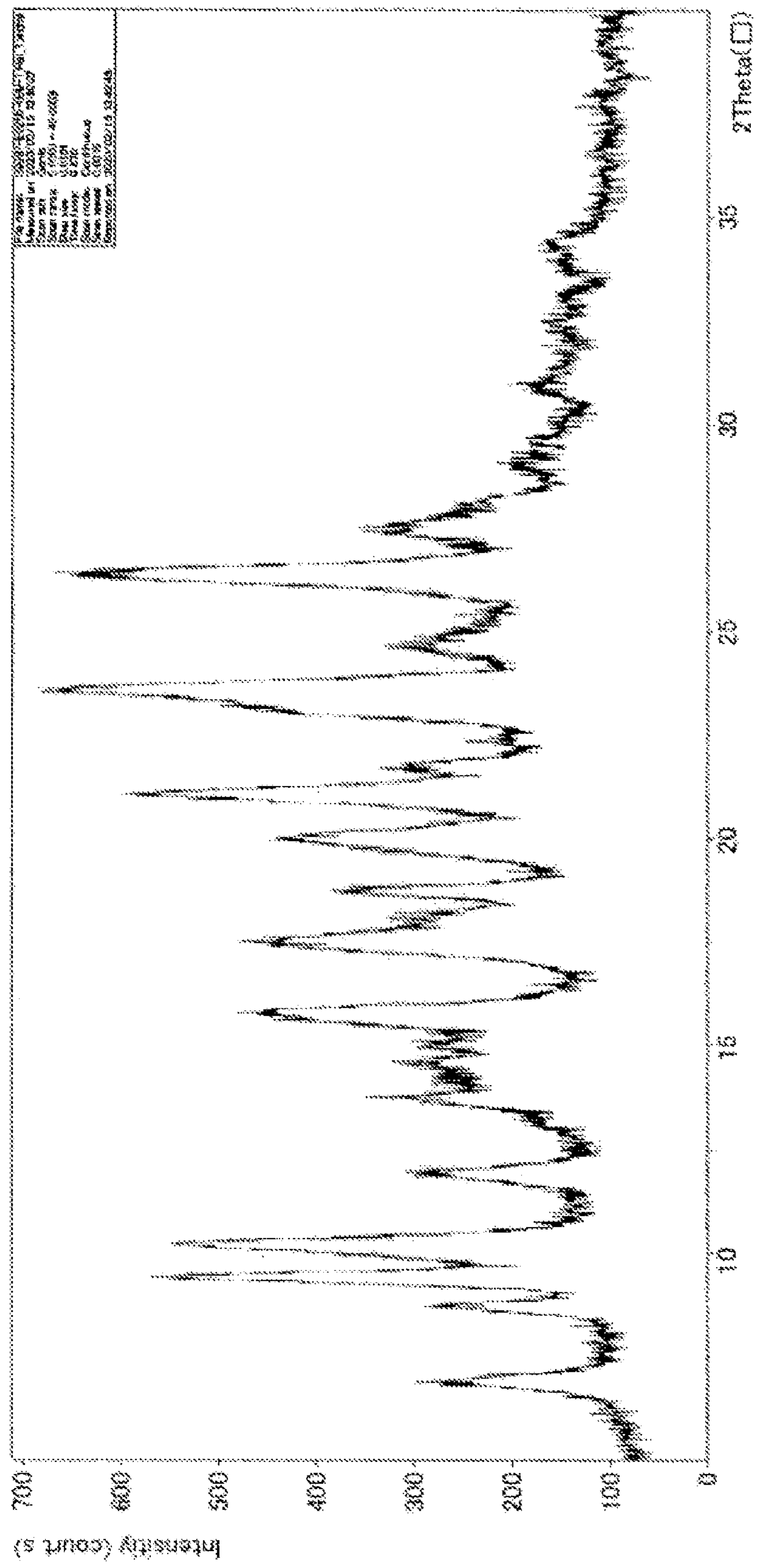

[Figure 8]
Simultaneous thermogravimetry-differential thermal analysis (TG-DTA) of type V crystal of compound (I) with 1 equivalent of fumaric acid
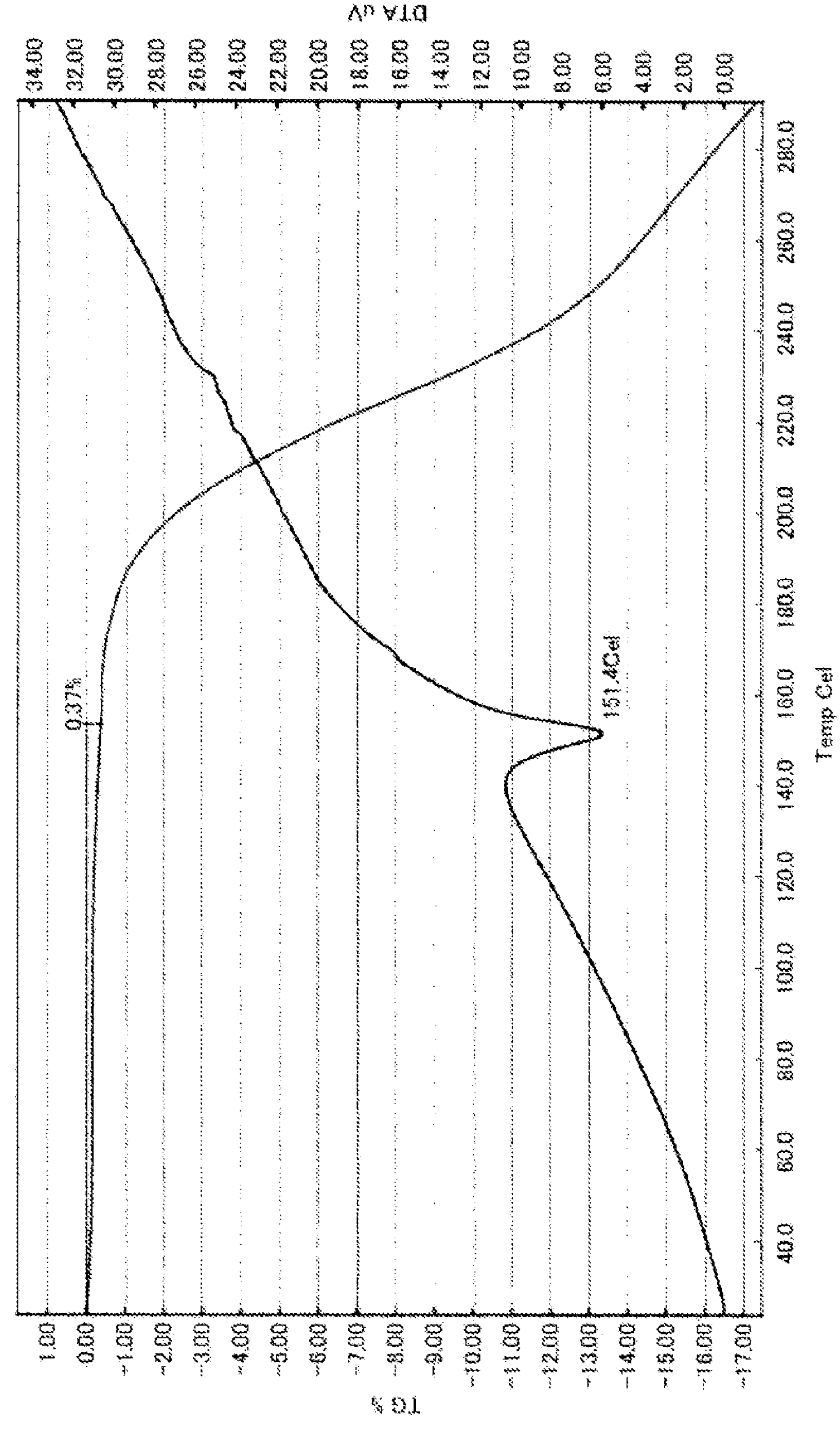

[Figure 9]
Powder X-ray diffraction spectrum of type I crystal of compound (I) with 1 equivalent of fumaric acid
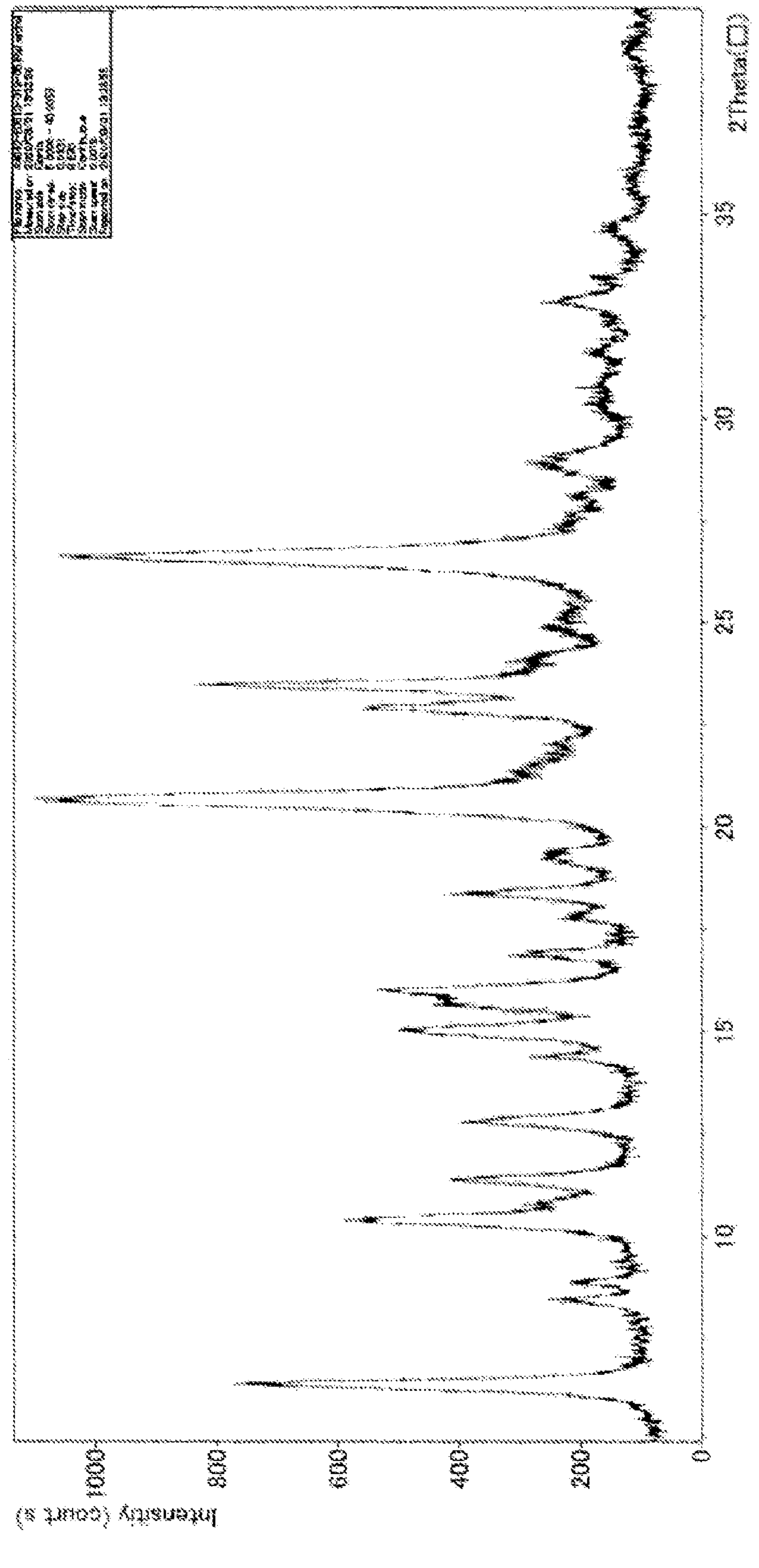

[Figure 10]
Simultaneous thermogravimetry-differential thermal analysis (TG-DTA) of type I crystal of compound (I) with 1 equivalent of fumaric acid
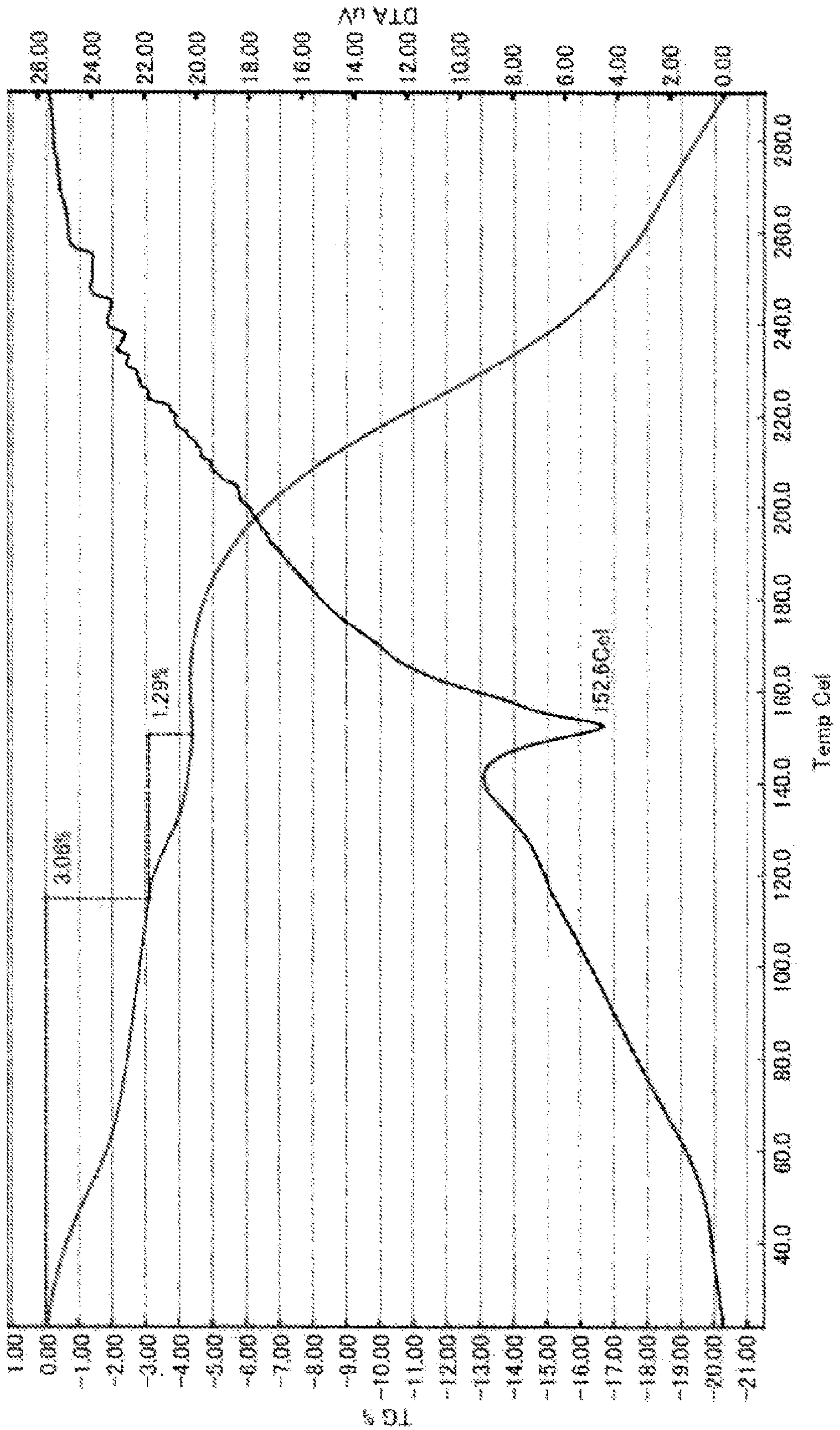

[Figure 11]
Powder X-ray diffraction spectrum of type I crystal of compound (I) with 0.5 equivalents of fumaric acid
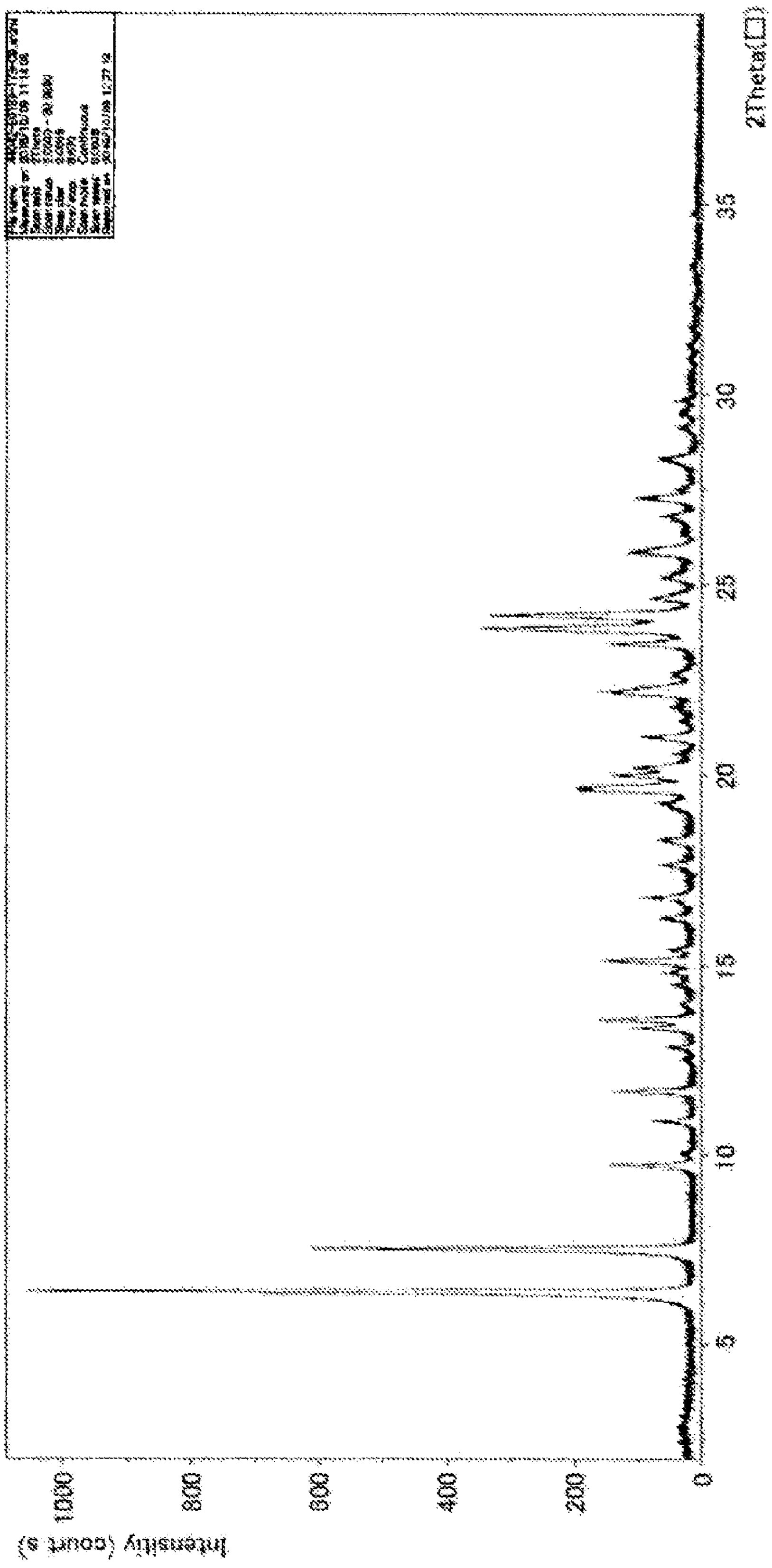

[Figure 12]
Simultaneous thermogravimetry-differential thermal analysis (TG-DTA) of type I crystal of compound (I) with 0.5 equivalents of fumaric acid
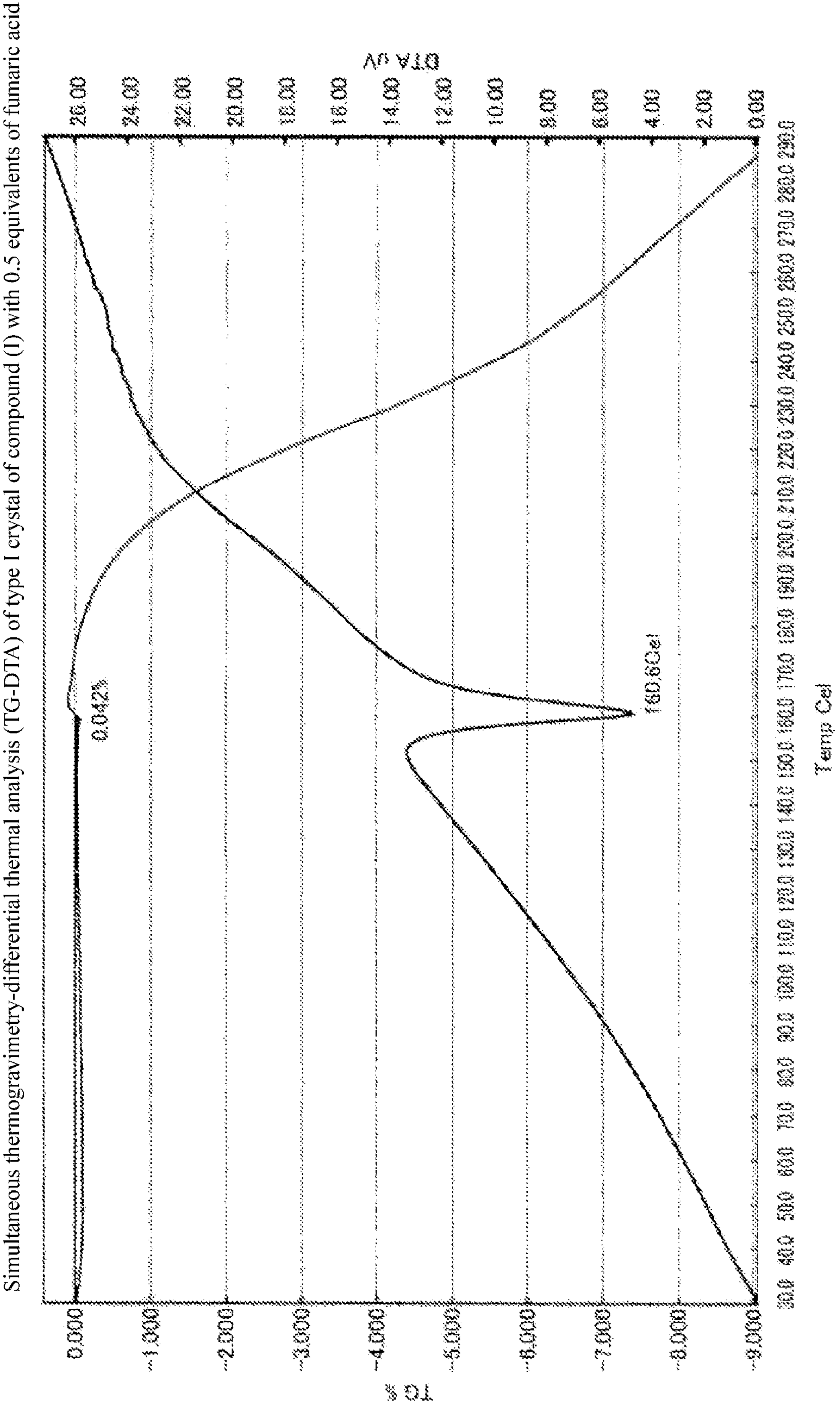

[Figure 13]
Powder X-ray diffraction spectrum of type II crystal of compound (I) with 0.5 equivalents of fumaric acid
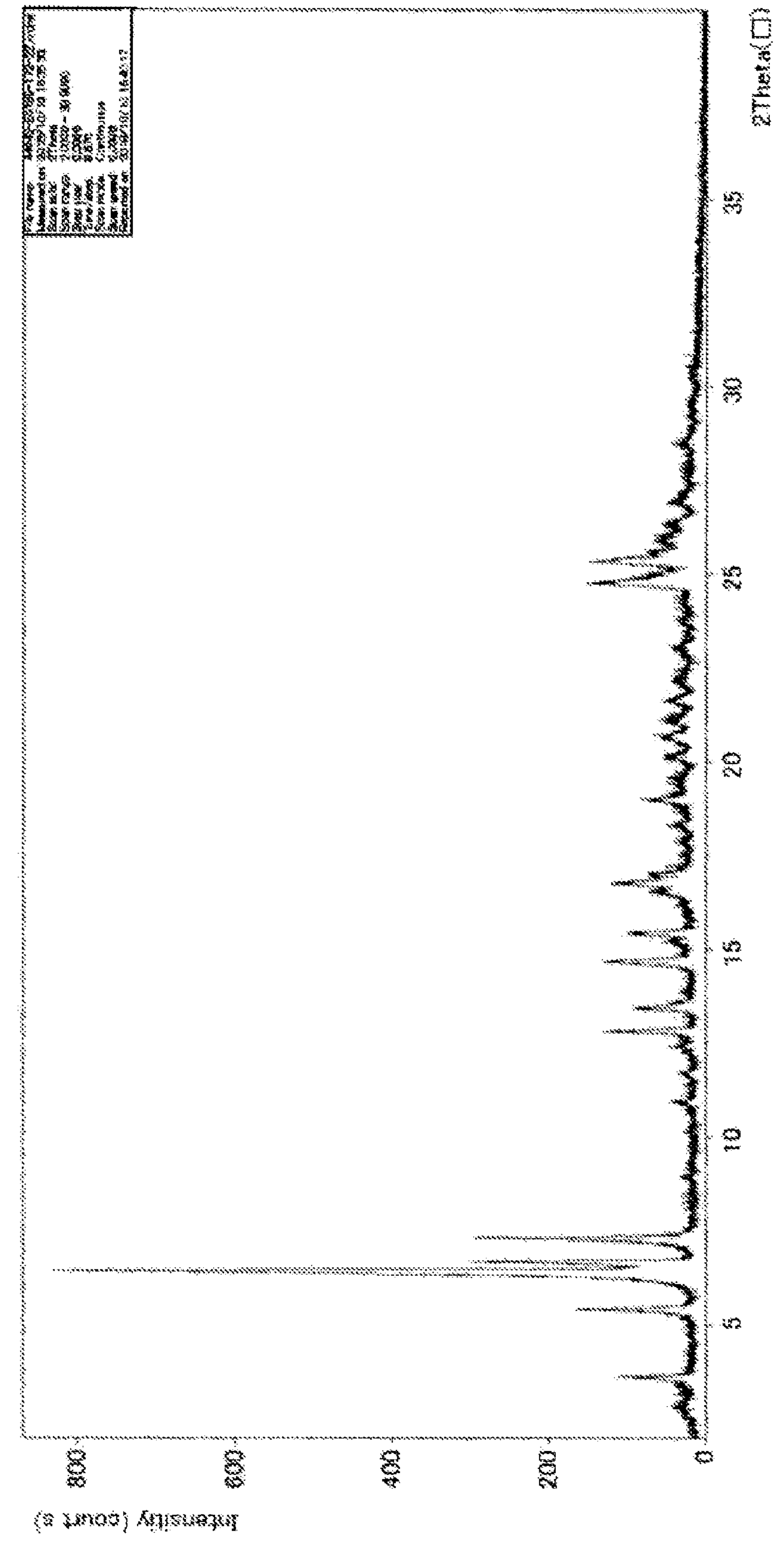

[Figure 14]
Simultaneous thermogravimetry-differential thermal analysis (TG-DTA) of type II crystal of compound (I) with 0.5 equivalent of fumaric acid
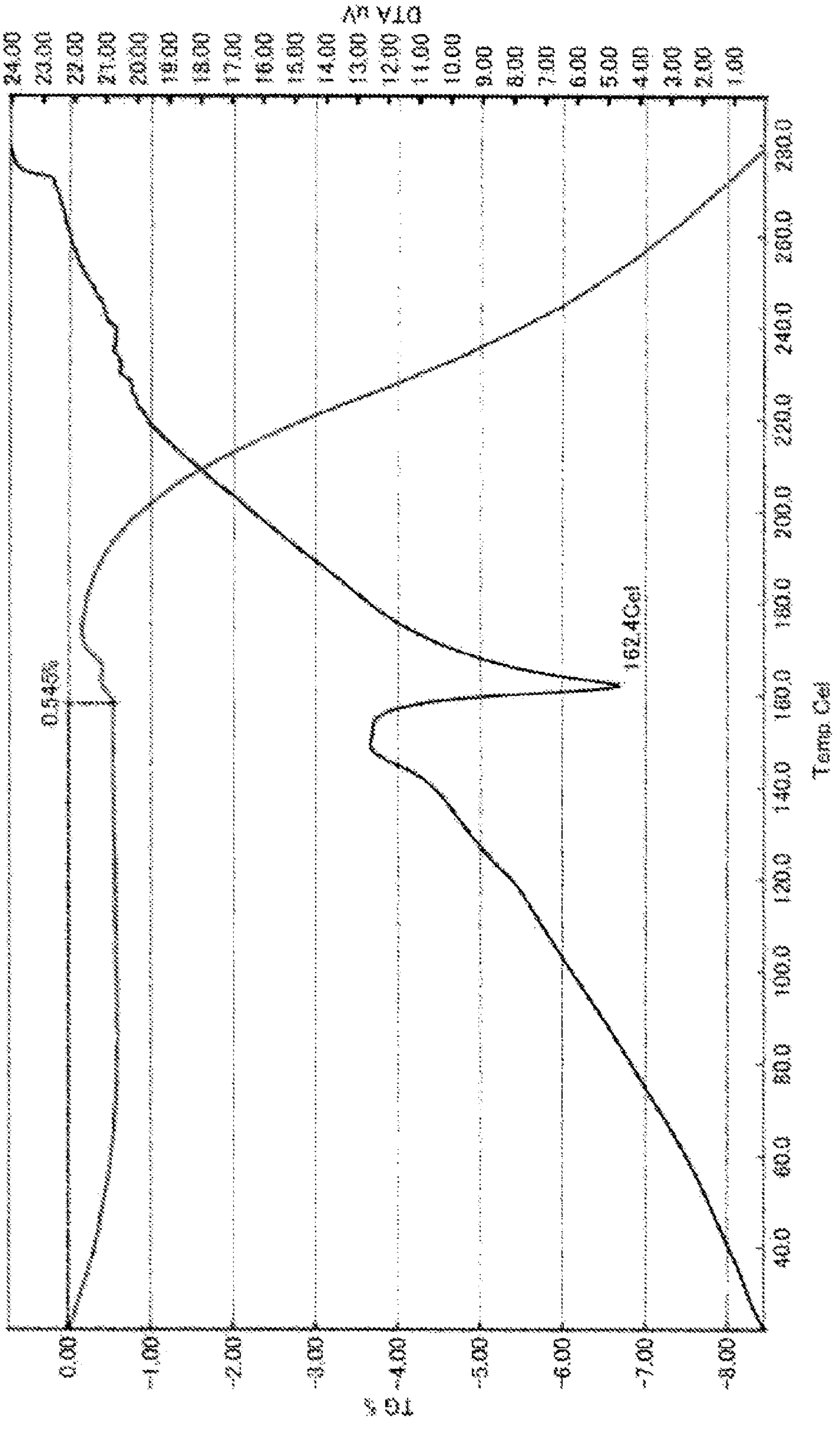

[Figure 15]
Powder X-ray diffraction spectrum of type III crystal of compound (I) with 1 equivalent of fumaric acid
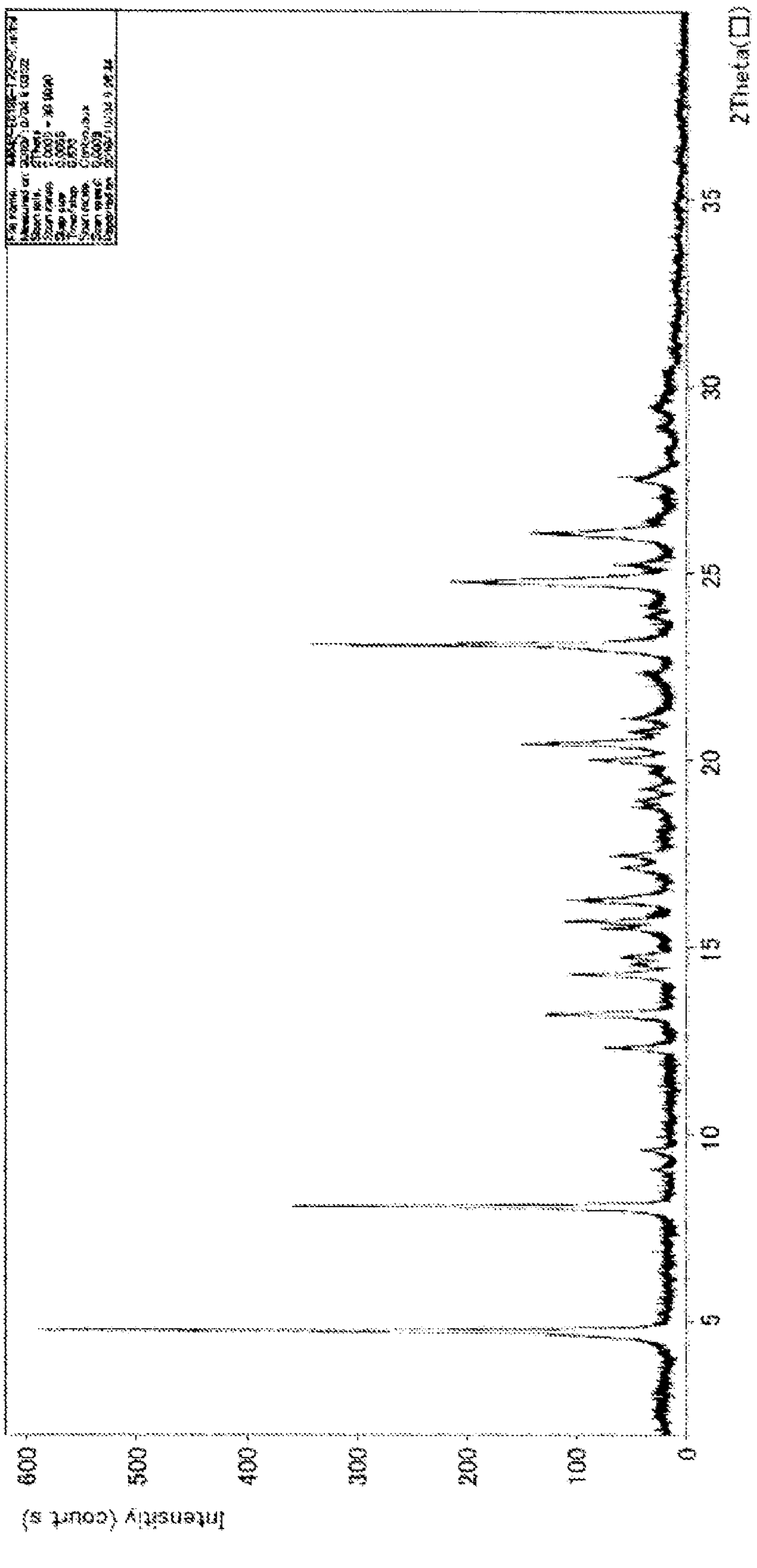

[Figure 16]
Simultaneous thermogravimetry-differential thermal analysis (TG-DTA) of type III crystal of compound (I) with 1 equivalent of fumaric acid
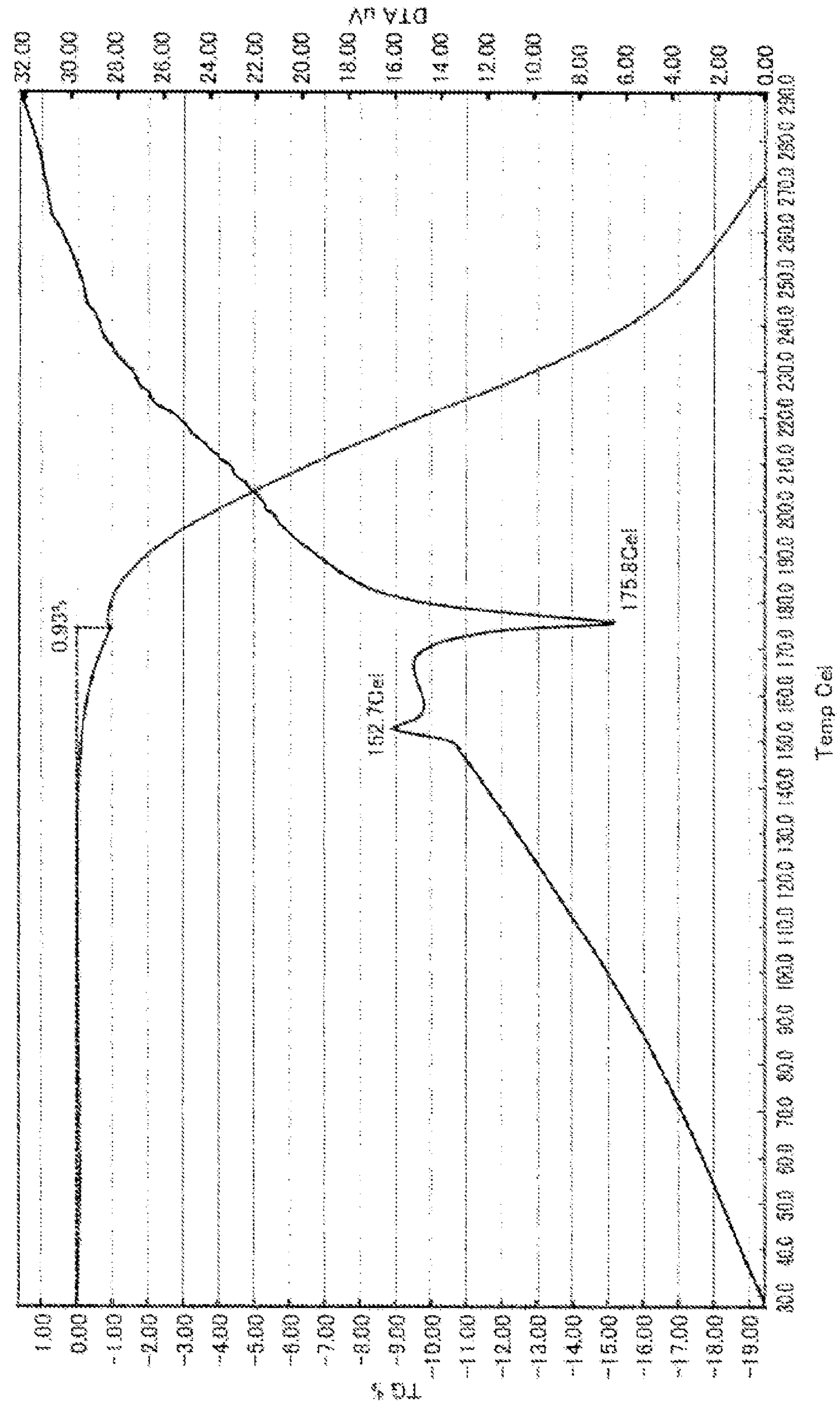

[Figure 17]
Powder X-ray diffraction spectrum of type IV crystal of compound (I) with 1 equivalent of fumaric acid
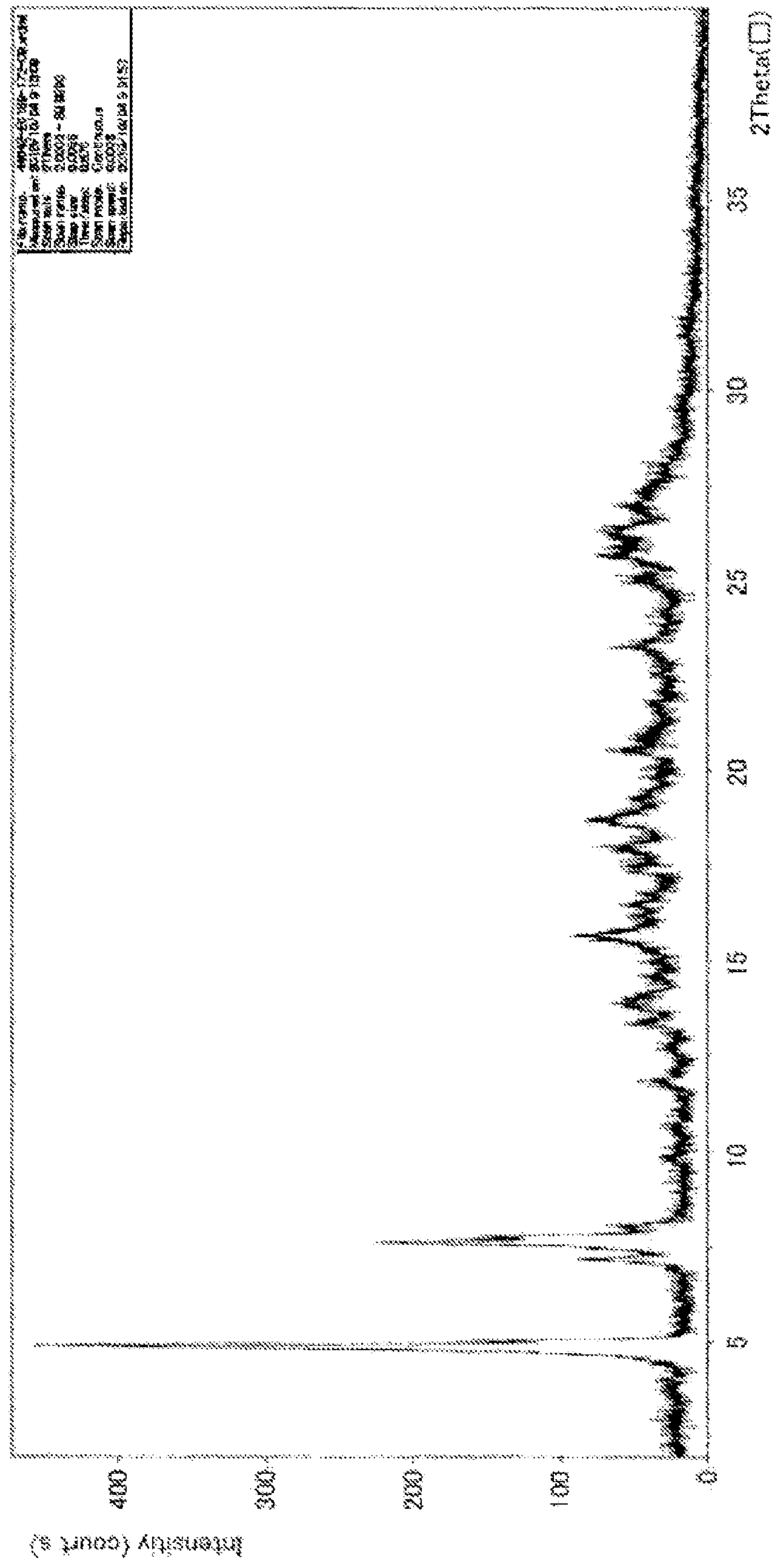

[Figure 18]
Simultaneous thermogravimetry-differential thermal analysis (TG-DTA) of type IV crystal of compound (I) with 1 equivalent of fumaric acid
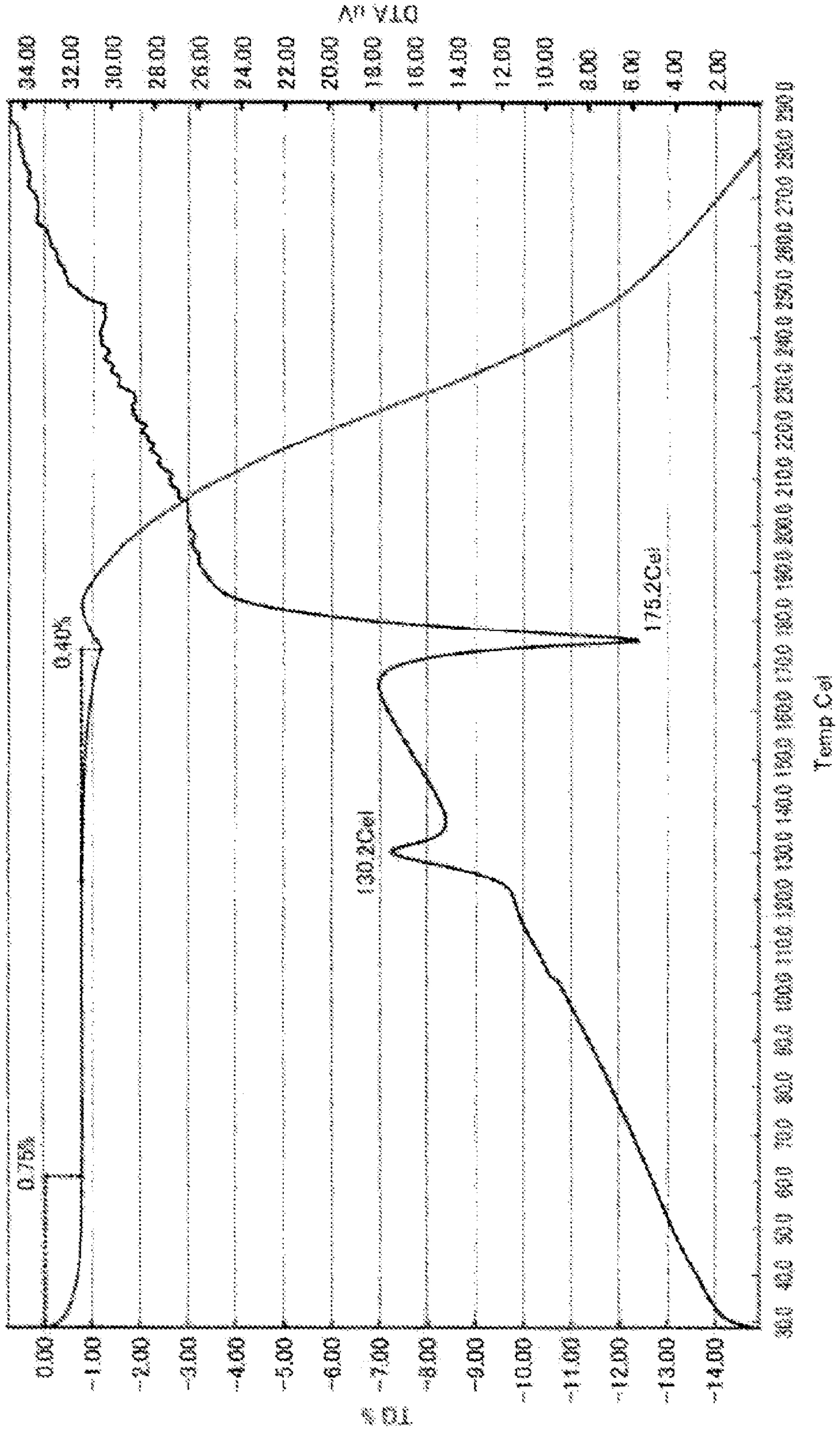

[Figure 19]
Powder X-ray diffraction spectrum of type I crystal of compound (I) with hydrochloric acid
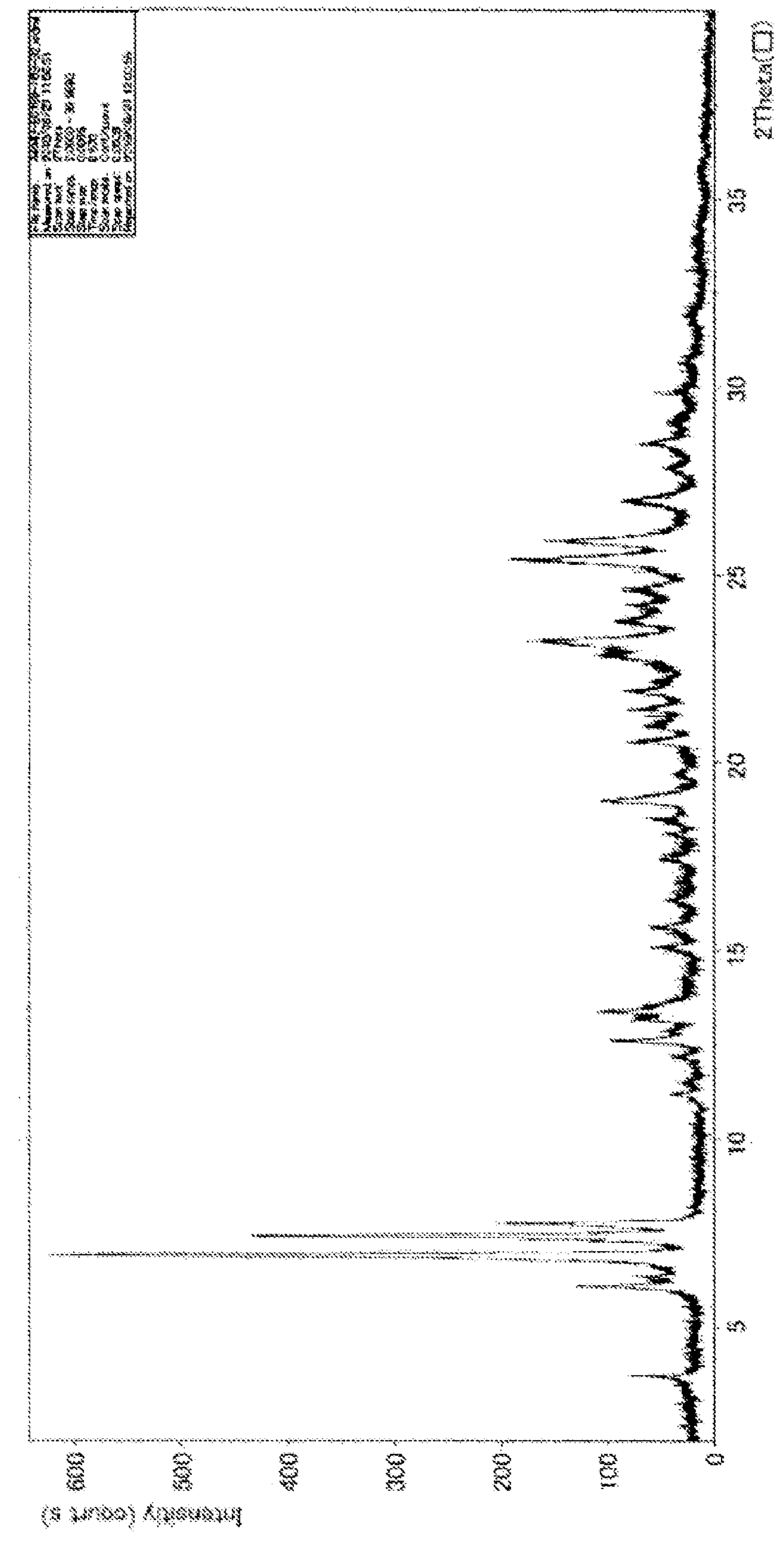

[Figure 20]
Simultaneous thermogravimetry-differential thermal analysis (TG-DTA) of type I crystal of compound (I) with hydrochloric acid
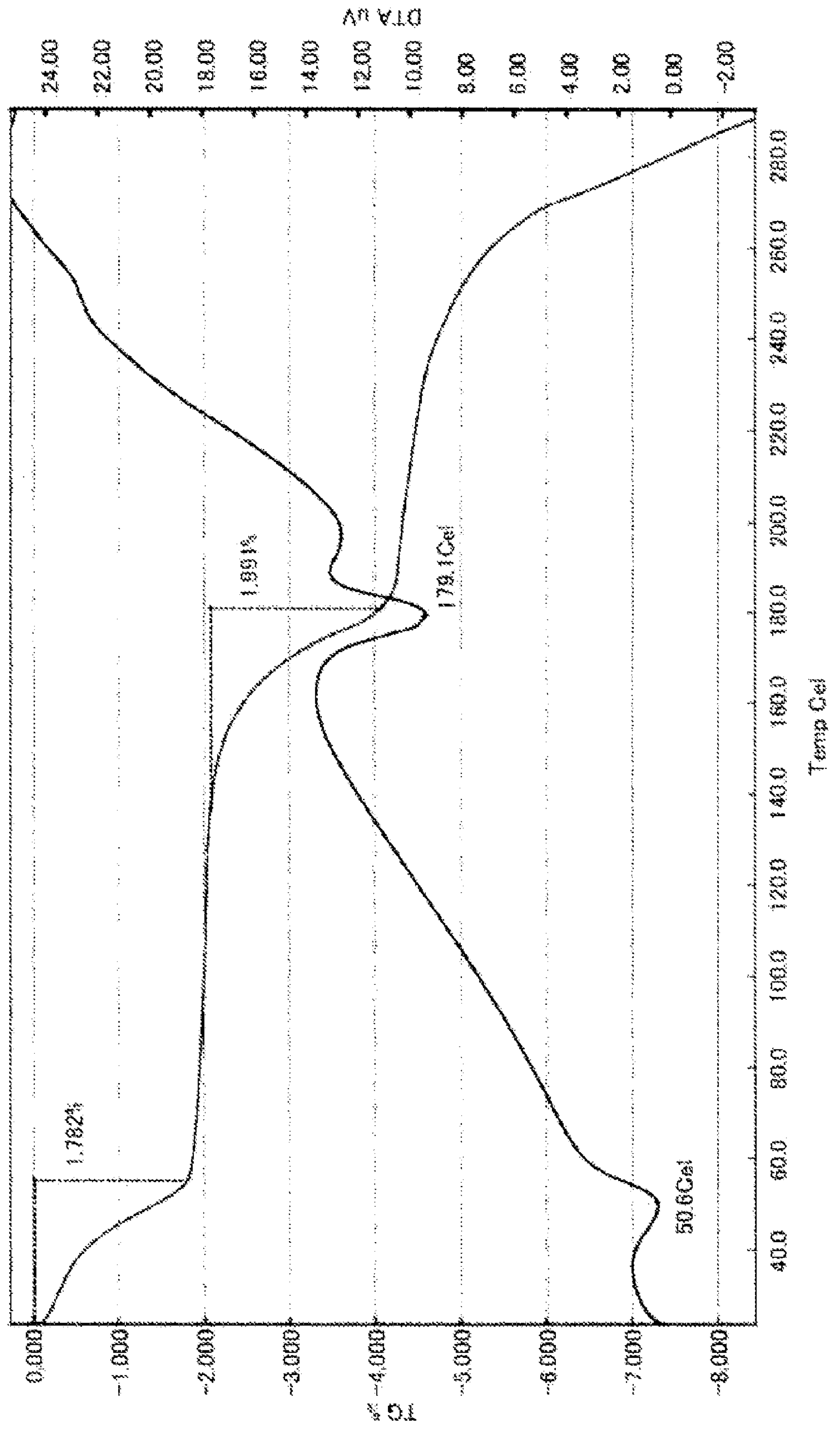

[Figure 21]
Powder X-ray diffraction spectrum of type II crystal of compound (I) with hydrochloric acid
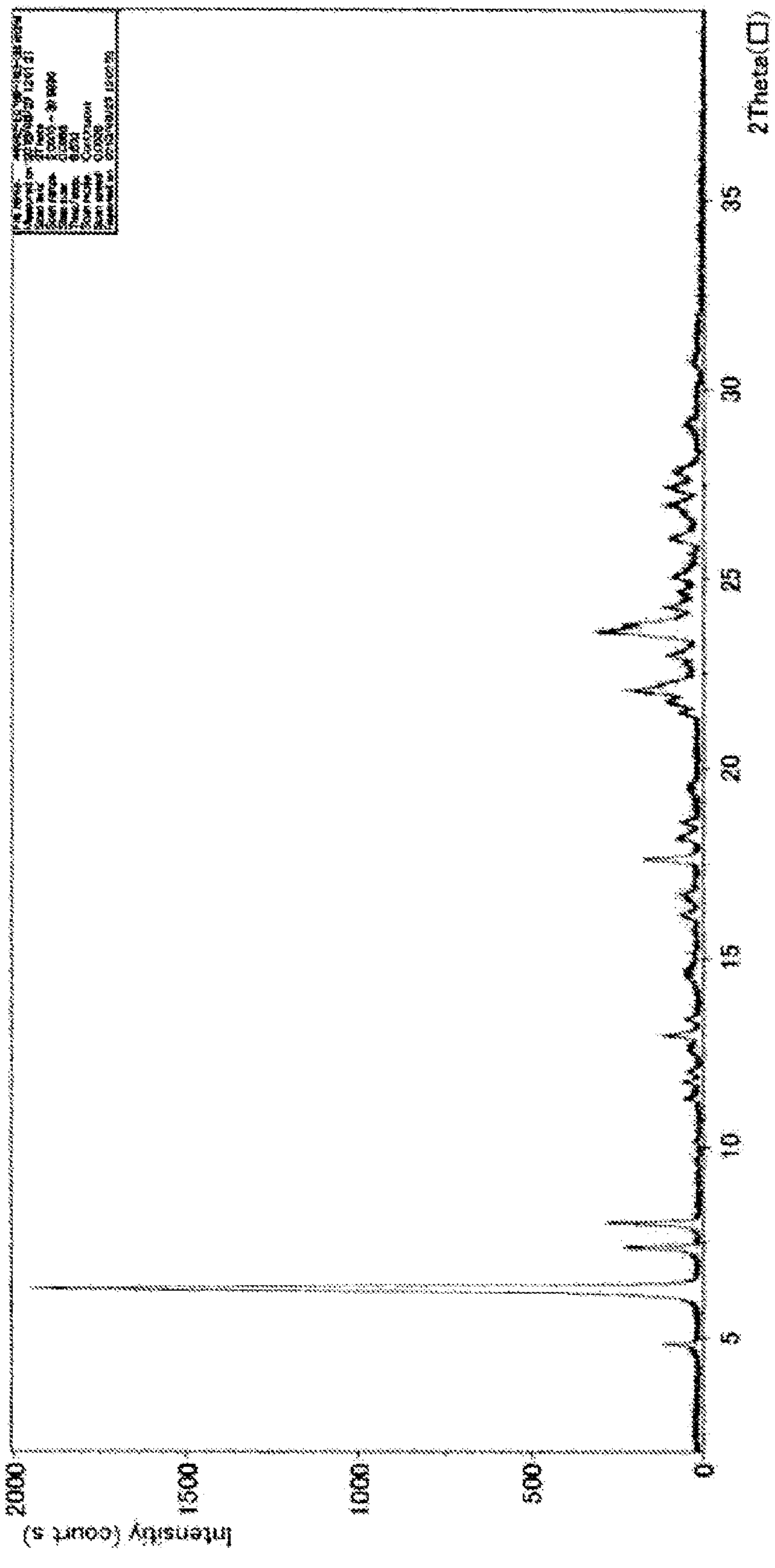

[Figure 22]
Simultaneous thermogravimetry-differential thermal analysis (TG-DTA) of type II crystal of compound (I) with hydrochloric acid
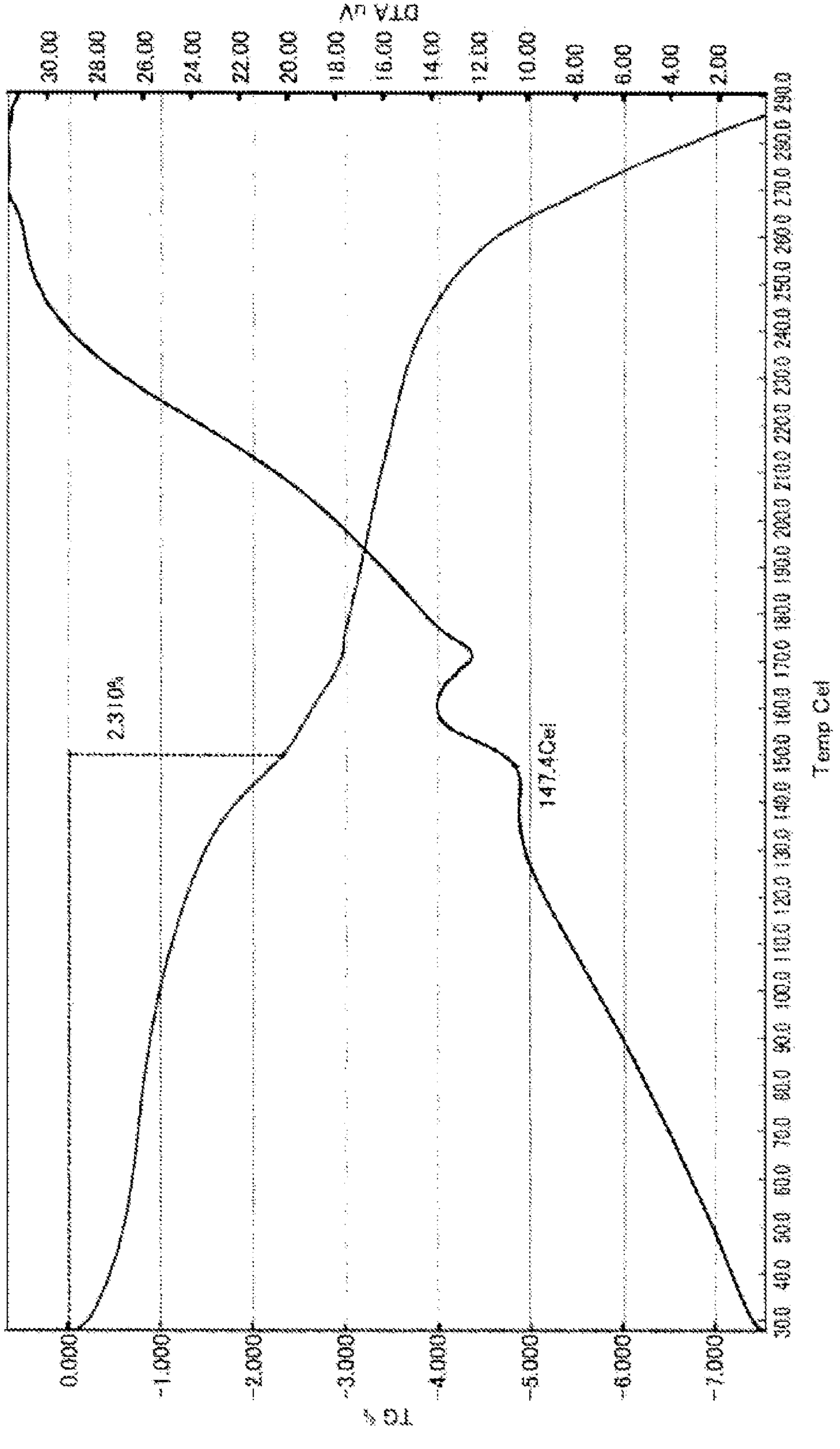

[Figure 23]
Powder X-ray diffraction spectrum of type III crystal of compound (I) with hydrochloric acid
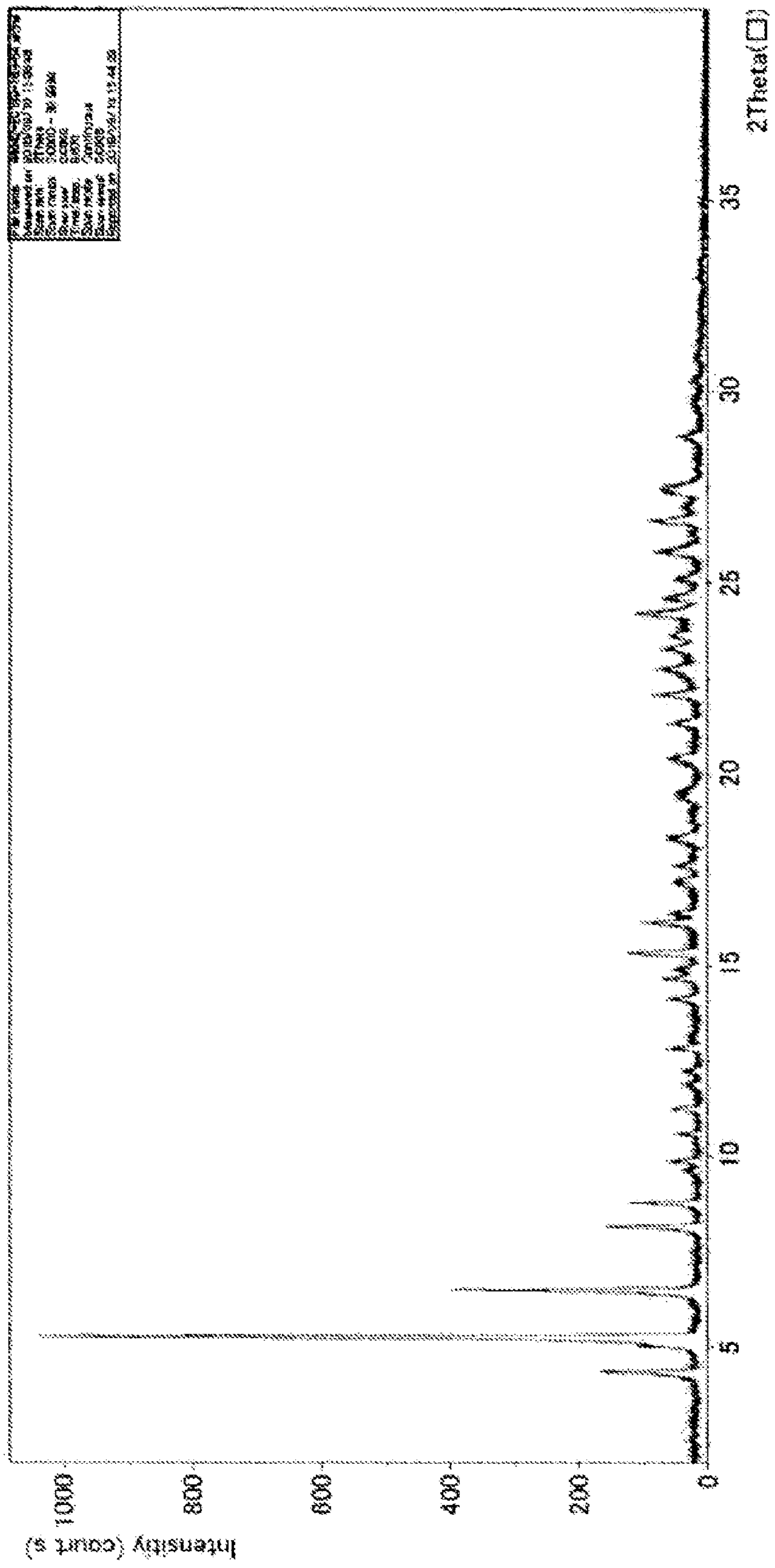

[Figure 24]
Simultaneous thermogravimetry-differential thermal analysis (TG-DTA) of type III crystal of compound (I) with hydrochloric acid
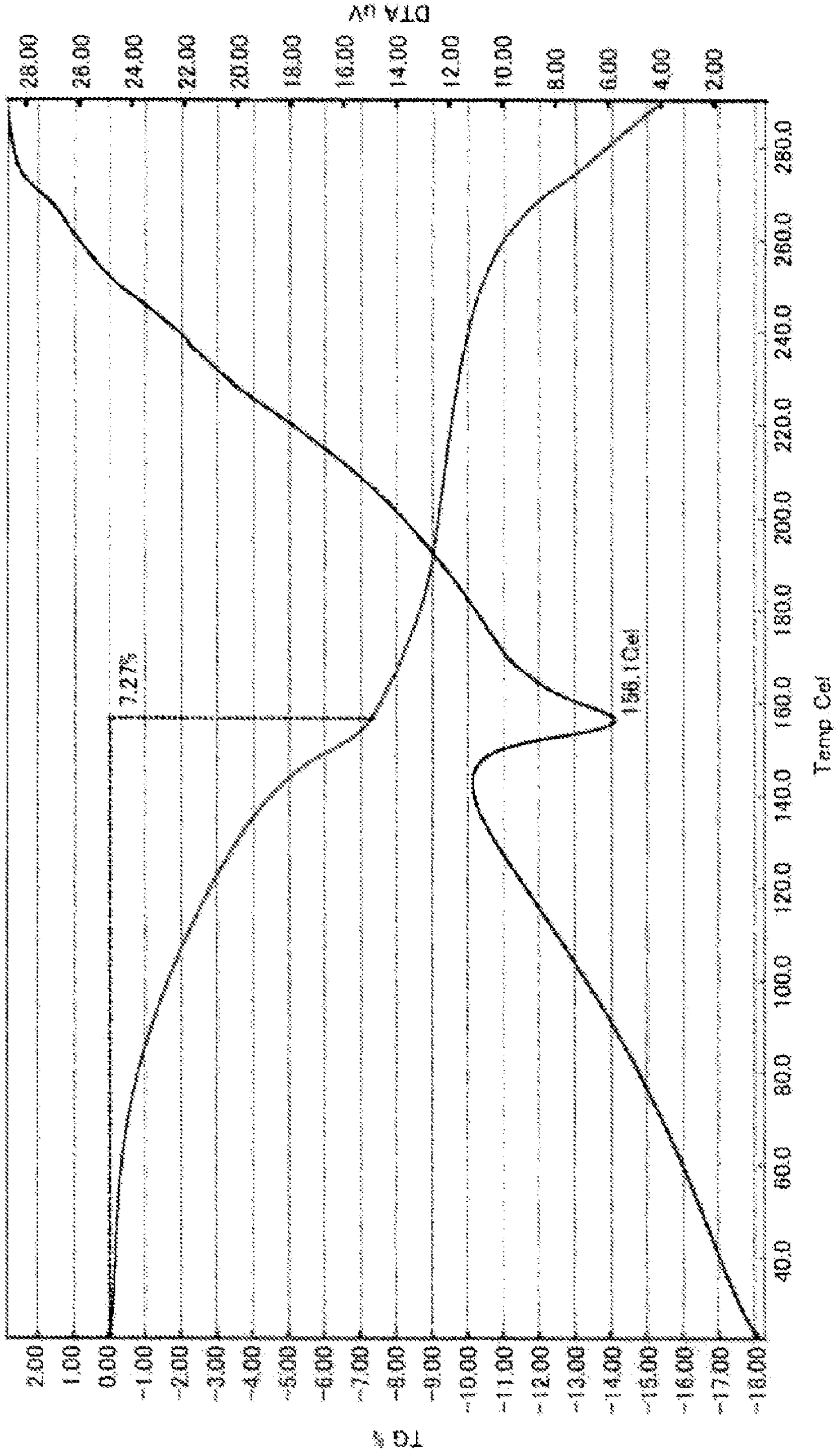

[Figure 25]
Powder X-ray diffraction spectrum of crystal of compound (I) with hydrobromic acid
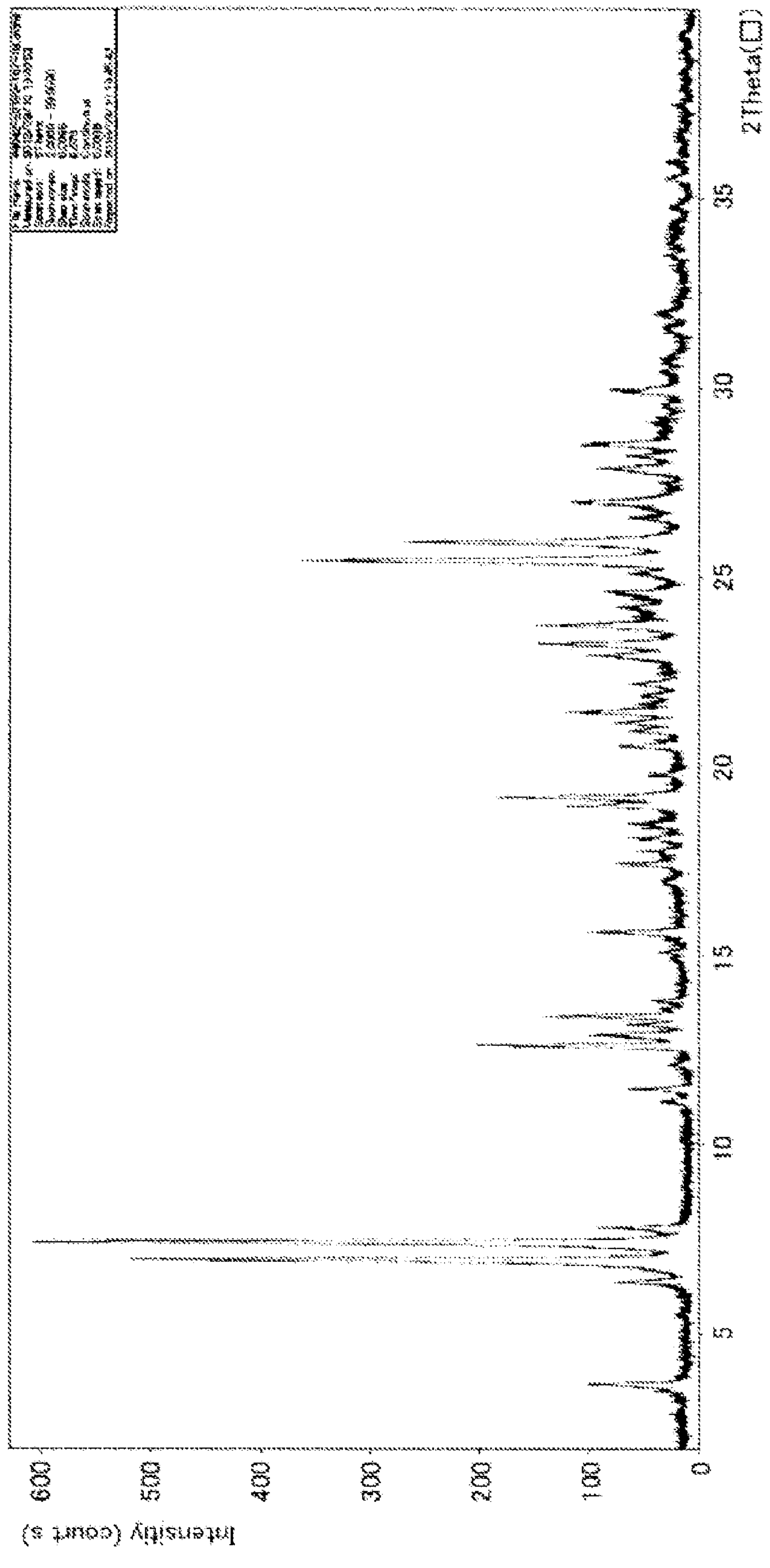

[Figure 26]
Simultaneous thermogravimetry-differential thermal analysis (TG-DTA) of crystal of compound (I) with hydrobromic acid
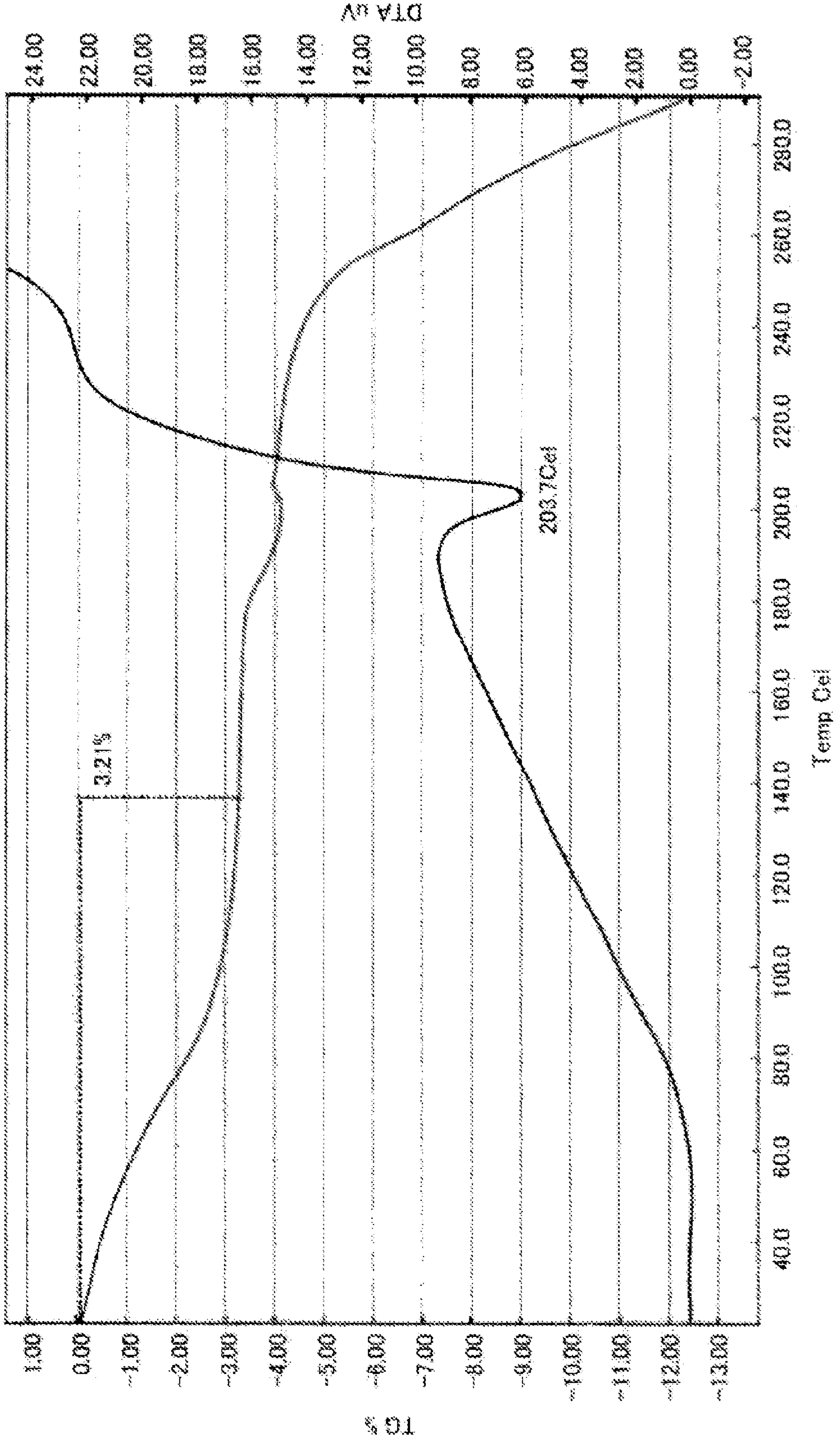

[Figure 27]
Powder X-ray diffraction spectrum of crystal of compound (I) with 1 equivalent of L-tartaric acid
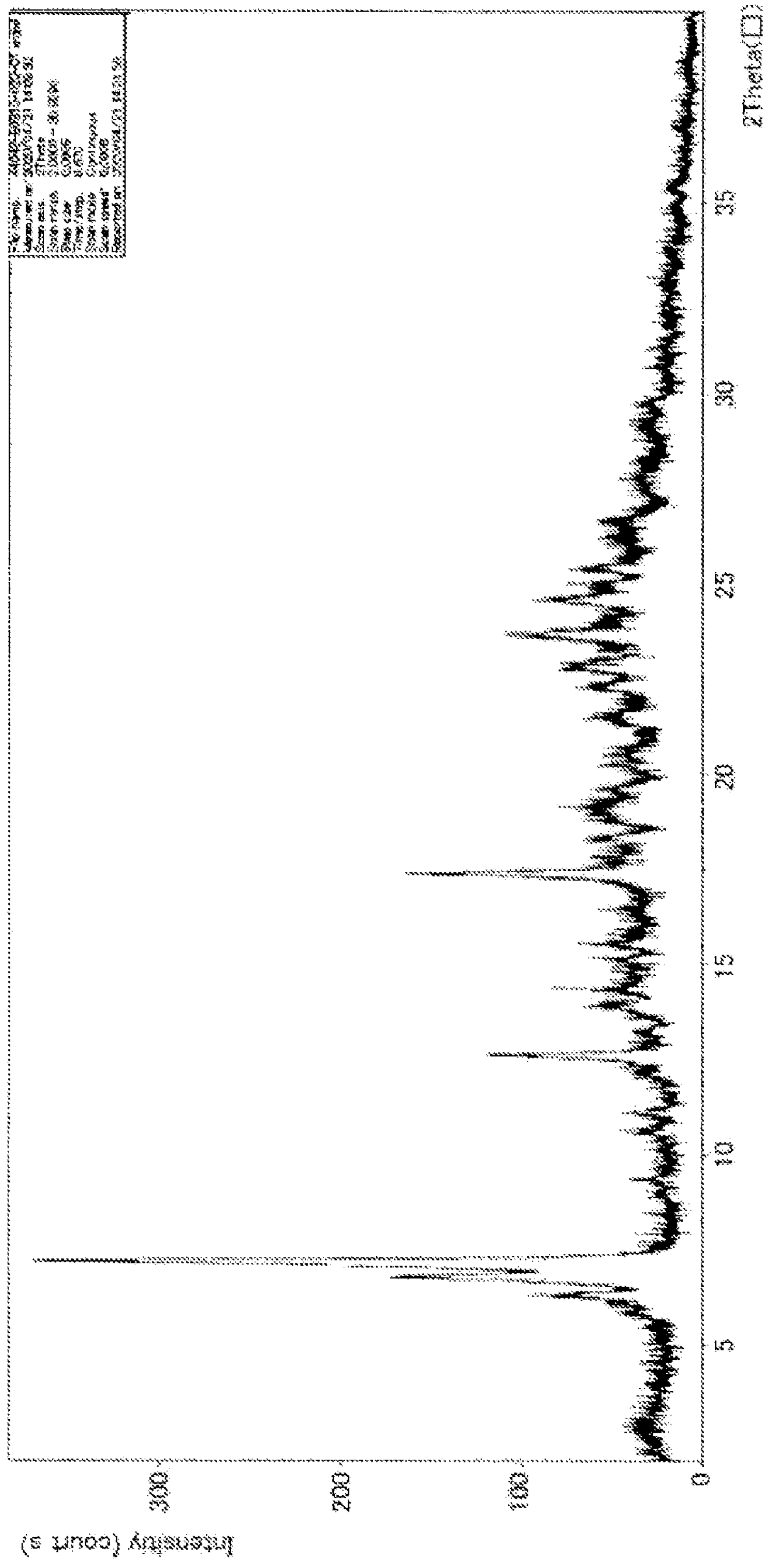

[Figure 28]
Simultaneous thermogravimetry-differential thermal analysis (TG-DTA) of crystal of compound (I) with 1 equivalent of L-tartaric acid
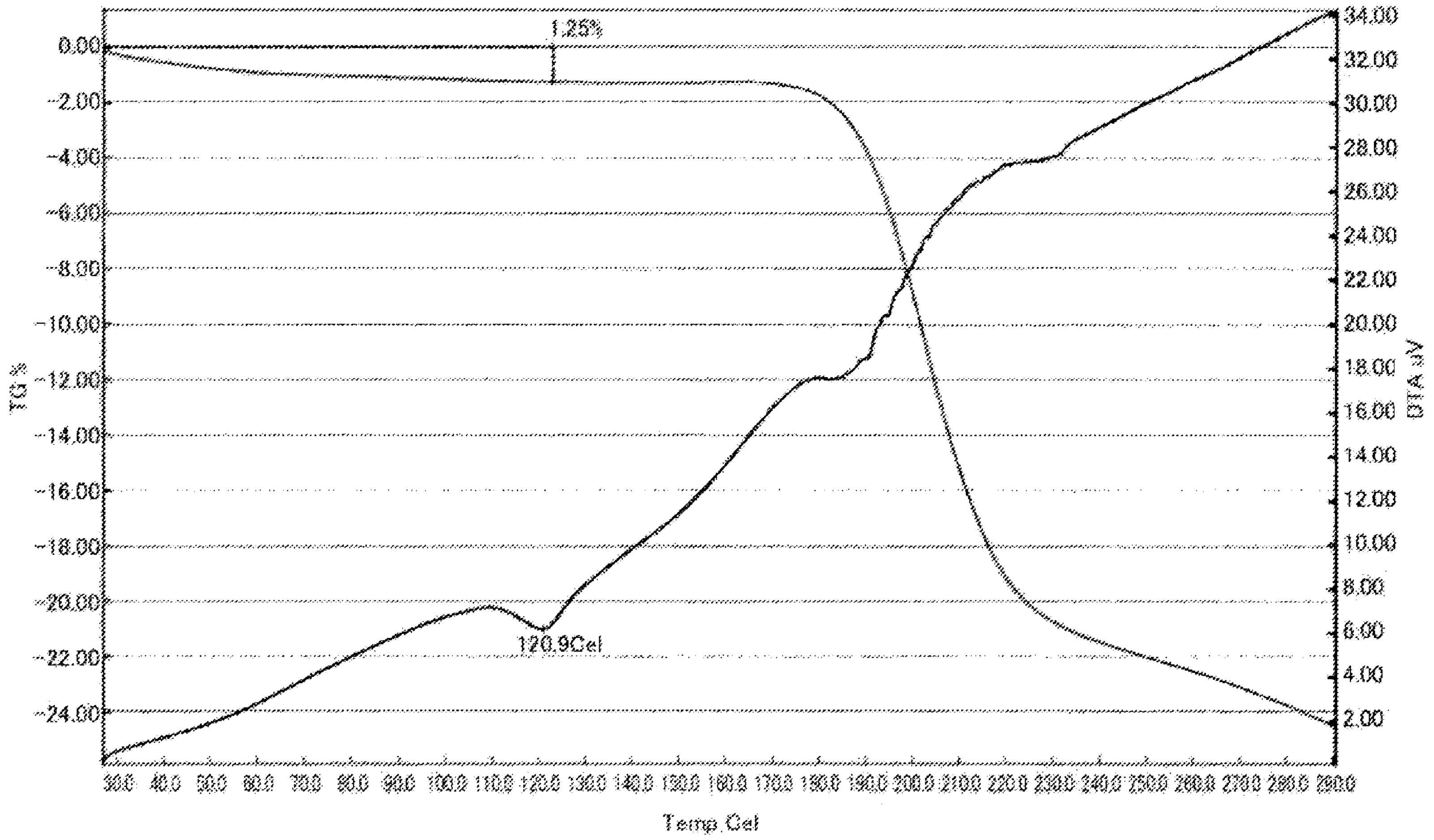

[Figure 29]
Powder X-ray diffraction spectrum of crystal of compound (I) with succinic acid
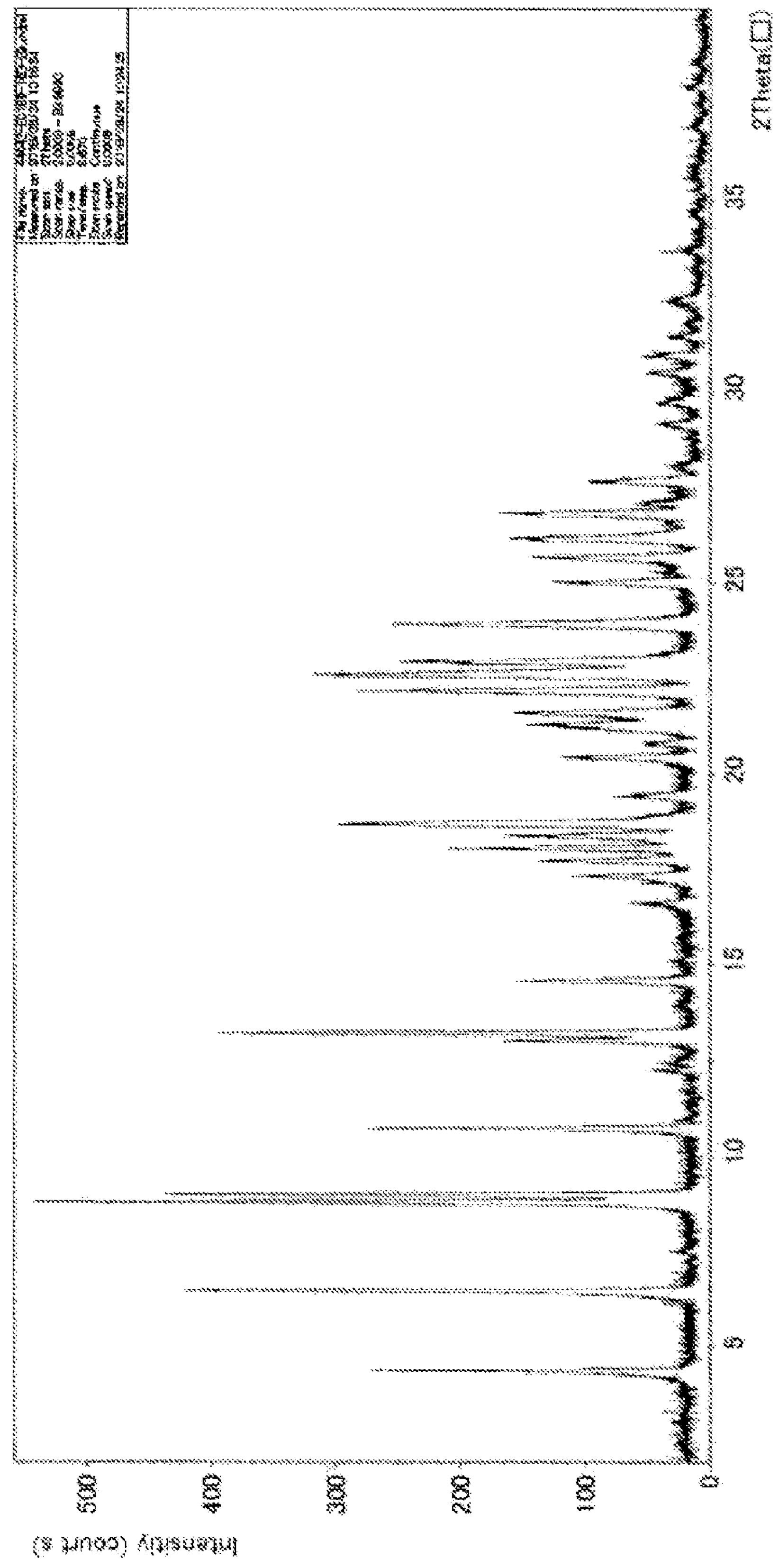

[Figure 30]
Simultaneous thermogravimetry-differential thermal analysis (TG-DTA) of crystal of compound (I) with succinic acid
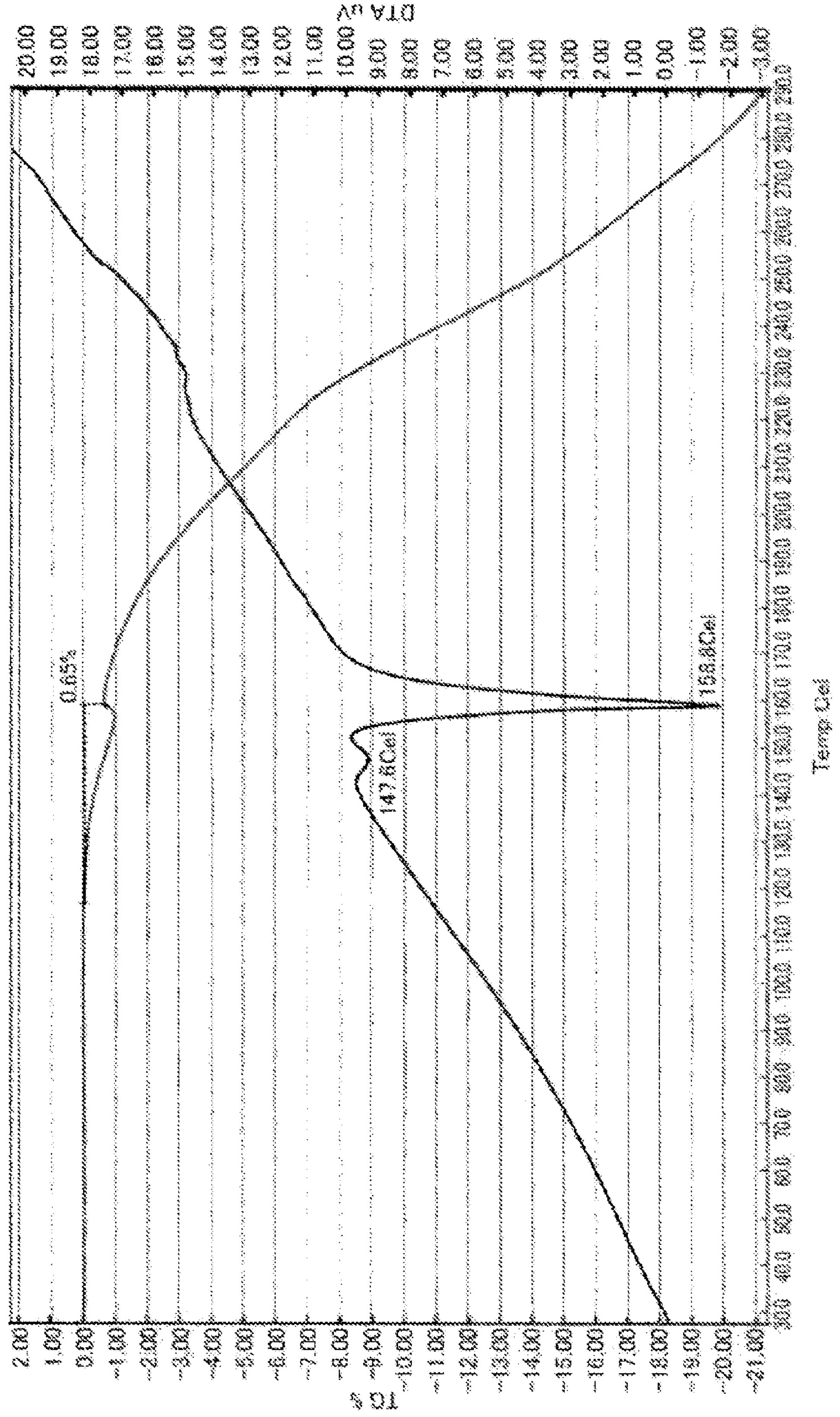

[Figure 31]
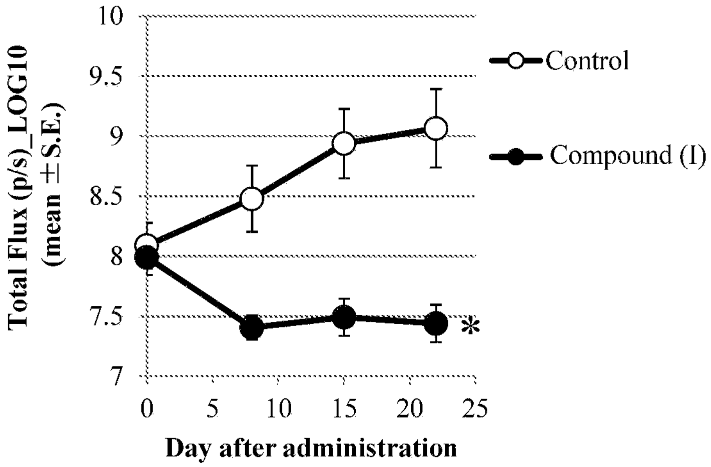
* : P=0.0007
[Figure 32]
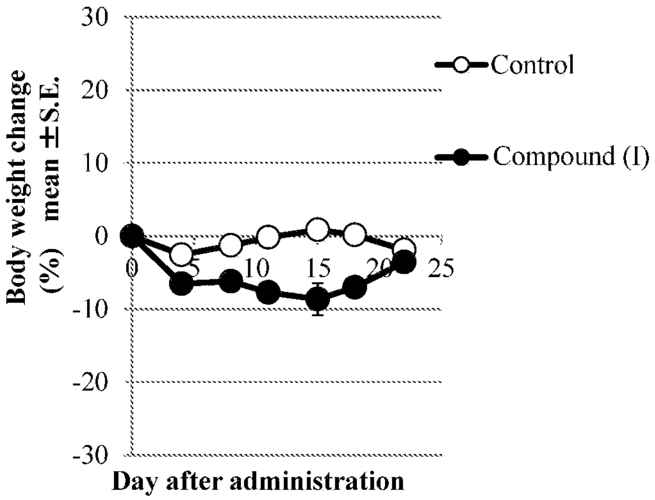

CRYSTAL OF PYRIMIDINE COMPOUND

TECHNICAL FIELD

The present invention relates to a crystal of pyrimidine compound useful as an antitumor agent, and a pharmaceutical composition comprising the crystal.

BACKGROUND ART

HER2 (which is also referred to as "ErbB2") is receptor tyrosine kinase belonging to the ErbB family.

HER2 is considered to be a proto-oncogene. It has been reported that HER2 gene amplification, overexpression, mutation and the like occur in various types of cancers. From non-clinical and clinical research data, it is considered that activation of HER2 and downstream signals plays an important role in the survival and/or proliferation, etc. of cancer cells associated with the genetic abnormality, overexpression and the like of HER2 (Non Patent Literature 1).

Accordingly, an inhibitor capable of regulating the kinase activity of HER2 is assumed to inhibit HER2 and downstream signals in cancer cells having HER2 gene amplification, overexpression or mutation, so as to exhibit antitumor effects on the cancer cells. Therefore, such an inhibitor is considered to be useful for the treatment, life-prolonging, or QOL improvement of cancer patients.

It has been reported that brain metastasis occurs in approximately 25% to 40% of lung cancer cases, in approximately 15% to 30% of breast cancer cases, and in certain percentages of other multiple cancer cases (Non Patent Literatures 2 and 3). As a matter of fact, it has been reported that brain metastasis occurs in approximately 20% to 30% of HER2-positive breast cancer cases (Non Patent Literature 4).

Compounds having HER2 inhibitory activity, such as Lapatinib and Neratinib, have been approved as therapeutic agents against HER2-positive breast cancer. However, it has been reported that since all of these therapeutic agents are substrates of p-gp or Bcrp, the brain penetration properties of these agents are limited in non-clinical tests (Non Patent Literature 5). In fact, in clinical tests using Lapatinib or Neratinib, sufficient effects of these agents could not be obtained against brain metastatic cancer (Non Patent Literatures 6, 7, 8, and 9).

From the viewpoint of the control of pathological conditions including brain metastasis nidus, it has been desired to develop a HER2 inhibitor having inhibitory activity against HER2 and also having brain penetration properties.

Generally, when a compound is used as an active ingredient in a pharmaceutical product, the chemical and physical stability of the compound is required to maintain stable quality and/or to facilitate storage control. It has been desired to develop a HER2 inhibitor having chemical and physical stability and inhibitory activity against HER2 and also having brain penetration properties.

CITATION LIST

Non Patent Literature

Non Patent Literature 1: Cancer Treatment Reviews, 40, pp. 770-780 (2014)
Non Patent Literature 2: Current Oncology, 25, pp. S103-S114 (2018)
Non Patent Literature 3: Breast Cancer Research, 18 (1), 8, pp. 1-9 (2016)
Non Patent Literature 4: Journal of Clinical Oncology, 28, pp. 3271-3277 (2010)
Non Patent Literature 5: Journal of Medicinal Chemistry, 59, pp. 10030-10066 (2016)
Non Patent Literature 6: Journal of Clinical Oncology, 26, pp. 2999-3005 (2008)
Non Patent Literature 7: Journal of Clinical Oncology, 26, pp. 1993-1999 (2008)
Non Patent Literature 8: Journal of Clinical Oncology, 28, pp. 1301-1307 (2010)
Non Patent Literature 9: Journal of Clinical Oncology, 34, pp. 945-952 (2016)

SUMMARY OF INVENTION

Technical Problem

It is an object of the present invention to provide a HER2 inhibitor having chemical and physical stability and inhibitory activity against HER2 and also having brain penetration properties. In particular, it is an object of the present invention to provide a crystal of a HER2 inhibitor that are excellent in stability, have good oral absorbability, and can be obtained with good reproducibility.

Solution to Problem

As a result of intensive studies in order to achieve the above objects, the present inventors have found that 7-((3R, 5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide represented by the following formula (I) (hereinafter also referred to as "compound (I)") has HER2 inhibitory activity and brain penetration properties, and is useful as a therapeutic agent for diseases involving HER2 (particularly malignant tumor) by inhibiting HER2.

(I)

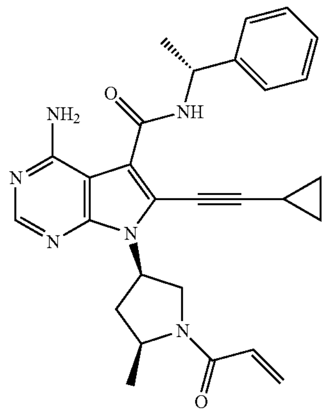

In addition, the present inventors have found that there are two free-form crystals (type I crystal and type II crystal) and crystals with acids (salt crystals or co-crystals) of the compound (I), including crystals with hydrochloric acid (type I crystal with hydrochloric acid, type II crystal with hydrochloric acid, type III crystal with hydrochloric acid), crystals with hydrobromic acid, crystals with 1 equivalent of tartaric acid, crystals with fumaric acid (type I crystal with 0.5 equivalents of fumaric acid, type II crystal with 0.5 equivalents of fumaric acid, type I crystal with 1 equivalent of fumaric acid, type II crystal with 1 equivalent of fumaric acid, type III crystal with 1 equivalent of fumaric acid, type IV crystal with 1 equivalent of fumaric acid, type V crystal with 1 equivalent of fumaric acid), and crystals with succinic acid.

The present inventors have found that among these crystals, a free-form type I crystal, a free-form type II crystal, a type II crystal with 1 equivalent of fumaric acid, a type V crystal with 1 equivalent of fumaric acid have advantageous properties in pharmaceutical manufacturing such as a non-hygroscopic property and excellent solid stability, and also have excellent oral absorbability. This has led to the completion of the present invention.

Specifically, the present invention includes the following embodiments.

[1] A crystal having peaks at three or more diffraction angles (2θ±0.2°) selected from 5.5°, 6.8°, 9.3°, 13.4°, 15.3°, 16.3°, 18.5°, 19.8°, 22.0°, and 24.5° in a powder X-ray diffraction spectrum, which is a type II crystal of 7-((3R, 5S)-1-acryloyl-5-methylpyrrolidin-3-yl)-4-amino-6-(cyclopropylethynyl)-N—((R)-1-phenylethyl)-7H-pyrrolo[2,3-d] pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2,3-d]pyrimidine-5-carboxamide to fumaric acid is 1:1.

[2] The crystal according to [1], which has peaks at diffraction angles (2θ±0.2°) of 5.5°, 6.8°, 9.3°, 13.4°, 15.3°, 16.3°, 18.5°, 19.8°, 22.0°, and 24.5° in a powder X-ray diffraction spectrum.

[3] The crystal according to [1] or [2], which is a crystal having a powder X-ray diffraction spectrum shown in FIG. 1.

[4] The crystal according to any one of [1] to [3], which has an endothermic peak determined by simultaneous thermogravimetry-differential thermal analysis at around 178° C.

[5] The crystal according to any one of [1] to [4], wherein the purity of the crystal is 90% by mass or more.

[6] A crystal having peaks at three or more diffraction angles (2θ±0.2°) selected from 8.3°, 14.8°, 17.3°, 18.0°, 19.1°, 20.3°, 21.0°, 22.5°, 23.0°, and 26.2° in a powder X-ray diffraction spectrum, which is a type II crystal of 7-((3R,5S)-1-acryloyl-5-methylpyrrolidin-3-yl)-4-amino-6-(cyclopropylethynyl)-N—((R)-1-phenylethyl)-7H-pyrrolo [2,3-d]pyrimidine-5-carboxamide.

[7] The crystal according to [6], which has peaks at diffraction angles (2θ±0.2°) of 8.3°, 14.8°, 17.3°, 18.0°, 19.1°, 20.3°, 21.0°, 22.5°, 23.0°, and 26.2° in a powder X-ray diffraction spectrum.

[8] The crystal according to [6] or [7], which is a crystal having a powder X-ray diffraction spectrum shown in FIG. 3.

[9] The crystal according to any one of [6] to [8], which has an endothermic peak determined by simultaneous thermogravimetry-differential thermal analysis at around 182° C.

[10] The crystal according to any one of [6] to [9], wherein the purity of the crystal is 90% by mass or more.

[11] A crystal having peaks at four or more diffraction angles (2θ±0.2°) selected from 9.9°, 11.7°, 13.2°, 17.7°, 18.1°, 18.8°, and 20.8° in a powder X-ray diffraction spectrum, which is a type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide.

[12] The crystal according to [11], which has peaks at diffraction angles (2θ±0.2°) of 9.9°, 11.7°, 13.2°, 17.7°, 18.1°, 18.8°, and 20.8° in a powder X- ray diffraction spectrum.

[13] The crystal according to [11] or [12], which is a crystal having a powder X-ray diffraction spectrum shown in FIG. 5.

[14] The crystal according to any one of [11] to [13], which has an endothermic peak determined by simultaneous thermogravimetry-differential thermal analysis at around 182° C.

[15] The crystal according to any one of [11] to [14] wherein the purity of the crystal is 90% by mass or more.

[16] A crystal having peaks at four or more diffraction angles (2θ±0.2°) selected from 6.9°, 9.4°, 10.2°, 13.7°, 21.1°, 23.6°, and 26.5° in a powder X-ray diffraction spectrum, which is a type V crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2,3-d]pyrimidine-5-carboxamide to fumaric acid is 1:1.

[17] The crystal according to [16], which has peaks at diffraction angles (2θ±0.2°) of 6.9°, 9.4°, 10.2°, 13.7°, 21.1°, 23.6°, and 26.5° in a powder X-ray diffraction spectrum.

[18] The crystal according to [16] or [17], which is a crystal having a powder X-ray diffraction spectrum shown in FIG. 7.

[19] The crystal according to any one of [16] to [18], which has an endothermic peak determined by simultaneous thermogravimetry-differential thermal analysis at around 151° C.

[20] The crystal according to any one of [16] to [19], wherein the purity of the crystal is 90% by mass or more.

[21] A crystal having peaks at four or more diffraction angles (2θ±0.2°) selected from 6.4°, 10.3°, 12.8°, 15.0°, 20.7°, 23.4°, and 26.6° in a powder X-ray diffraction spectrum, which is a type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2,3-d]pyrimidine-5-carboxamide to fumaric acid is 1:1.

[22] The crystal according to [21], which has peaks at diffraction angles (2θ±0.2°) of 6.4°, 10.3°, 12.8°, 15.0°, 20.7°, 23.4°, and 26.6° in a powder X-ray diffraction spectrum.

[23] The crystal according to [21] or [22], which is a crystal having a powder X-ray diffraction spectrum shown in FIG. 9.

[24] The crystal according to any one of [21] to [23], which has an endothermic peak determined by simultaneous thermogravimetry-differential thermal analysis at around 153° C.

[25] The crystal according to any one of [21] to [24], wherein the purity of the crystal is 90% by mass or more.

[26] A crystal having peaks at four or more diffraction angles (2θ±0.2°) selected from 6.4°, 7.5°, 9.7°, 11.7°, 15.1°, 19.6°, and 23.9° in a powder X-ray diffraction spectrum, which is a type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid, wherein a molar ratio of 7-((3R,5S)-1-acryloyl-5-methylpyrrolidin-3-yl)-4-amino-6-

(cyclopropylethynyl)-N—((R)-1-phenylethyl)-7H-pyrrolo2, 3-d]pyrimidine-5-carboxamide to fumaric acid is 1:0.5.

[27] The crystal according to [26], which has peaks at diffraction angles (2θ±0.2°) of 6.4°, 7.5°, 9.7°, 11.7°, 15.1°, 19.6°, and 23.9° in a powder X-ray diffraction spectrum.

[28] The crystal according to [26] or [27], which is a crystal having a powder X-ray diffraction spectrum shown in FIG. 11.

[29] The crystal according to any one of [26] to [28], which has an endothermic peak determined by simultaneous thermogravimetry-differential thermal analysis at around 161° C.

[30] The crystal according to any one of [26] to [29], wherein the purity of the crystal is 90% by mass or more.

[31] A crystal having peaks at four or more diffraction angles (2θ±0.2°) selected from 5.4°, 6.4°, 7.3°, 12.8°, 13.4°, 14.7°, and 15.4° in a powder X-ray diffraction spectrum, which is a type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2, 3-d]pyrimidine-5-carboxamide to fumaric acid is 1:0.5.

[32] The crystal according to [31], which has peaks at diffraction angles (2θ±0.2°) of 5.4°, 6.4°, 7.3°, 12.8°, 13.4°, 14.7°, and 15.4° in a powder X-ray diffraction spectrum.

[33] The crystal according to [31] or [32], which is a crystal having a powder X-ray diffraction spectrum shown in FIG. 13.

[34] The crystal according to any one of [31] to [33], which has an endothermic peak determined by simultaneous thermogravimetry-differential thermal analysis at around 162° C.

[35] The crystal according to any one of [31] to [34], wherein the purity of the crystal is 90% by mass or more.

[36] A pharmaceutical composition comprising the crystal according to any one of [1] to [35].

[37] A pharmaceutical composition for oral administration comprising the crystal according to any one of [1] to [35].

[38] An antitumor agent comprising the crystal according to any one of [1] to [35].

[39] The crystal according to any one of [1] to [35] for use as a medicament.

[40] Use of the crystal according to any one of [1] to [35] for the production of an antitumor agent for oral administration.

[41] The crystal according to any one of [1] to [35] for use in the treatment of tumor.

[42] The crystal according to any one of [1] to [35] for use in the treatment of tumor by oral administration thereof.

[43] A method for treating tumor, comprising administering an effective amount of the crystal according to any one of [1] to [12] to a subject in need thereof.

[44] Use of the crystal according to any one of [1] to [35] for the production of a pharmaceutical composition.

[45] Use of the crystal according to any one of [1] to [35] for the production of an antitumor agent.

Effects of Invention

A free-form type I crystal, a free-form type II crystal, a type II crystal with 1 equivalent of fumaric acid, a type V crystal with 1 equivalent of fumaric acid of the compound (I) (7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide) of the present invention are superior to other crystal forms in terms of high stability, handleability (lower hygroscopicity), quality controllability, and the like. In addition, the free-form type II crystal and the type II crystal with 1 equivalent of fumaric acid have excellent oral absorbability, and thus they are useful forms when using the compound as an active pharmaceutical ingredient. The type I crystal with 1 equivalent of fumaric acid is in a form that can be isolated as a solid from acetone (solvent) (after isolation, it is dried to form a type V crystal), it is also useful as an intermediate for the production of a type V crystal.

According to the present invention, a novel crystal of compound (I) or a novel crystal of compound (I) with an acid, and a pharmaceutical composition, an antitumor agent, or an antitumor agent for oral administration comprising the novel crystal are provided.

In preferred aspects, a type II crystal with 1 equivalent of fumaric acid, a free-form type II crystal, a free-form type I crystal, a type V crystal with 1 equivalent of fumaric acid, a type I crystal with 0.5 equivalents of fumaric acid, and a type II crystal with 0.5 equivalents of fumaric acid of the compound (I) have at least one of advantageous properties in pharmaceutical manufacturing such as a non-hygroscopic property, ability to be obtained with reproducibility, solid stability, and oral absorbability.

BRIEF DESCRIPTION OF DRAWINGS

FIG. 1 shows the powder X-ray diffraction spectrum of the type II crystal of compound (I) with 1 equivalent of fumaric acid obtained in Example 1 (the vertical axis represents the intensity (counts), and the horizontal axis represents the diffraction angle (2θ)).

FIG. 2 shows the results of simultaneous thermogravimetry-differential thermal analysis (TG-DTA) for the type II crystal of compound (I) with 1 equivalent of fumaric acid obtained in Example 1 (the left vertical axis represents the weight (mg) on the TG curve, the right vertical axis represents the heat flux (μV) on the DTA curve, and the horizontal axis represents the temperature (° C.)).

FIG. 3 shows the powder X-ray diffraction spectrum of the type II crystal of compound (I) obtained in Example 2 (the vertical axis represents the intensity (counts), and the horizontal axis represents the diffraction angle (2θ)).

FIG. 4 shows the results of simultaneous thermogravimetry-differential thermal analysis (TG-DTA) for the type II crystal of compound (I) obtained in Example 2 (the left vertical axis represents the weight (mg) on the TG curve, the right vertical axis represents the heat flux (μV) on the DTA curve, and the horizontal axis represents the temperature (° C.)).

FIG. 5 shows the powder X-ray diffraction spectrum of the type I crystal of compound (I) obtained in Example 3 (the vertical axis represents the intensity (counts), and the horizontal axis represents the diffraction angle (2θ)).

FIG. 6 shows the results of simultaneous thermogravimetry-differential thermal analysis (TG-DTA) for the type I crystal of compound (I) obtained in Example 3 (the left vertical axis represents the weight (mg) on the TG curve, the right vertical axis represents the heat flux (μV) on the DTA curve, and the horizontal axis represents the temperature (C)).

FIG. 7 shows the powder X-ray diffraction spectrum of the type V crystal of compound (I) with 1 equivalent of fumaric acid obtained in Example 4 (the vertical axis represents the intensity (counts), and the horizontal axis represents the diffraction angle (2θ)).

FIG. 8 shows the results of simultaneous thermogravimetry-differential thermal analysis (TG-DTA) for the type V crystal of compound (I) with 1 equivalent of fumaric acid obtained in Example 4 (the left vertical axis represents the weight (mg) on the TG curve, the right vertical axis represents the heat flux (μV) on the DTA curve, and the horizontal axis represents the temperature (° C.)).

FIG. 9 shows the powder X-ray diffraction spectrum of the type I crystal of compound (I) with 1 equivalent of fumaric acid obtained in Example 5 (the vertical axis represents the intensity (counts), and the horizontal axis represents the diffraction angle (2θ)).

FIG. 10 shows the results of simultaneous thermogravimetry-differential thermal analysis (TG-DTA) for the type I crystal of compound (I) with 1 equivalent of fumaric acid obtained in Example 5 (the left vertical axis represents the weight (mg) on the TG curve, the right vertical axis represents the heat flux (μV) on the DTA curve, and the horizontal axis represents the temperature (° C.)).

FIG. 11 shows the powder X-ray diffraction spectrum of the type I crystal of compound (I) with 0.5 equivalents of fumaric acid obtained in Example 6 (the vertical axis represents the intensity (counts), and the horizontal axis represents the diffraction angle (2θ)).

FIG. 12 shows the results of simultaneous thermogravimetry-differential thermal analysis (TG-DTA) for the type I crystal of compound (I) with 0.5 equivalents of fumaric acid obtained in Example 6 (the left vertical axis represents the weight (mg) on the TG curve, the right vertical axis represents the heat flux (μV) on the DTA curve, and the horizontal axis represents the temperature (C)).

FIG. 13 shows the powder X-ray diffraction spectrum of the type II crystal of compound (I) with 0.5 equivalents of fumaric acid obtained in Example 7 (the vertical axis represents the intensity (counts), and the horizontal axis represents the diffraction angle (2θ)).

FIG. 14 shows the results of simultaneous thermogravimetry-differential thermal analysis (TG-DTA) for the type II crystal of compound (I) with 0.5 equivalents of fumaric acid obtained in Example 7 (the left vertical axis represents the weight (mg) on the TG curve, the right vertical axis represents the heat flux (μV) on the DTA curve, and the horizontal axis represents the temperature (° C.)).

FIG. 15 shows the powder X-ray diffraction spectrum of the type III crystal of compound (I) with 1 equivalent of fumaric acid obtained in Reference Example 1 (the vertical axis represents the intensity (counts), and the horizontal axis represents the diffraction angle (2θ)).

FIG. 16 shows the results of simultaneous thermogravimetry-differential thermal analysis (TG-DTA) for the type III crystal of compound (I) with 1 equivalent of fumaric acid obtained in Reference Example 1 (the left vertical axis represents the weight (mg) on the TG curve, the right vertical axis represents the heat flux (μV) on the DTA curve, and the horizontal axis represents the temperature (° C.)).

FIG. 17 shows the powder X-ray diffraction spectrum of the type IV crystal of compound (I) with 1 equivalent of fumaric acid obtained in Reference Example 2 (the vertical axis represents the intensity (counts), and the horizontal axis represents the diffraction angle (2θ)).

FIG. 18 shows the results of simultaneous thermogravimetry-differential thermal analysis (TG-DTA) for the type IV crystal of compound (I) with 1 equivalent of fumaric acid obtained in Reference Example 2 (the left vertical axis represents the weight (mg) on the TG curve, the right vertical axis represents the heat flux (μV) on the DTA curve, and the horizontal axis represents the temperature (° C.)).

FIG. 19 shows the powder X-ray diffraction spectrum of the type I crystal of compound (I) with hydrochloric acid obtained in Reference Example 3 (the vertical axis represents the intensity (counts), and the horizontal axis represents the diffraction angle (2θ)).

FIG. 20 shows the results of simultaneous thermogravimetry-differential thermal analysis (TG-DTA) for the type I crystal of compound (I) with hydrochloric acid obtained in Reference Example 3 (the left vertical axis represents the weight (mg) on the TG curve, the right vertical axis represents the heat flux (μV) on the DTA curve, and the horizontal axis represents the temperature (C)).

FIG. 21 shows the powder X-ray diffraction spectrum of the type II crystal of compound (I) with hydrochloric acid obtained in Reference Example 4 (the vertical axis represents the intensity (counts), and the horizontal axis represents the diffraction angle (2θ)).

FIG. 22 shows the results of simultaneous thermogravimetry-differential thermal analysis (TG-DTA) for the type II crystal of compound (I) with hydrochloric acid obtained in Reference Example 4 (the left vertical axis represents the weight (mg) on the TG curve, the right vertical axis represents the heat flux (μV) on the DTA curve, and the horizontal axis represents the temperature (C)).

FIG. 23 shows the powder X-ray diffraction spectrum of the type III crystal of compound (I) with hydrochloric acid obtained in Reference Example 5 (the vertical axis represents the intensity (counts), and the horizontal axis represents the diffraction angle (2θ)).

FIG. 24 shows the results of simultaneous thermogravimetry-differential thermal analysis (TG-DTA) for the type III crystal of compound (I) with hydrochloric acid obtained in Reference Example 5 (the left vertical axis represents the weight (mg) on the TG curve, the right vertical axis represents the heat flux (μV) on the DTA curve, and the horizontal axis represents the temperature (° C.)).

FIG. 25 shows the powder X-ray diffraction spectrum of the crystal of compound (I) with hydrobromic acid obtained in Reference Example 6 (the vertical axis represents the intensity (counts), and the horizontal axis represents the diffraction angle (2θ)).

FIG. 26 shows the results of simultaneous thermogravimetry-differential thermal analysis (TG-DTA) for the crystal of compound (I) with hydrobromic acid obtained in Reference Example 6 (the left vertical axis represents the weight (mg) on the TG curve, the right vertical axis represents the heat flux (μV) on the DTA curve, and the horizontal axis represents the temperature (° C.)).

FIG. 27 shows the powder X-ray diffraction spectrum of the crystal of compound (I) with L-tartaric acid obtained in Reference Example 7 (the vertical axis represents the intensity (counts), and the horizontal axis represents the diffraction angle (2θ)).

FIG. 28 shows the results of simultaneous thermogravimetry-differential thermal analysis (TG-DTA) for the crystal of compound (I) with L-tartaric acid obtained in Reference Example 7 (the left vertical axis represents the weight (mg) on the TG curve, the right vertical axis represents the heat flux (μV) on the DTA curve, and the horizontal axis represents the temperature (° C.)).

FIG. 29 shows the powder X-ray diffraction spectrum of the crystal of compound (I) with succinic acid obtained in Reference Example 8 (the vertical axis represents the intensity (counts), and the horizontal axis represents the diffraction angle (2θ)).

FIG. 30 shows the results of simultaneous thermogravimetry-differential thermal analysis (TG-DTA) for the crystal of compound (I) with succinic acid obtained in Reference Example 8 (the left vertical axis represents the weight (mg) on the TG curve, the right vertical axis represents the heat flux (μV) on the DTA curve, and the horizontal axis represents the temperature (C)).

FIG. 31 shows the antitumor effects of the compound (I) against models involving direct brain transplantation of the Luciferase gene-introduced HER2 expressing cell line (NCI-N87-luc).

FIG. 32 shows the body weight reduction percentage of models involving direct brain transplantation of the Luciferase gene-introduced HER2 expressing cell line (NCI-N87-luc) caused by the compound (I).

DESCRIPTION OF EMBODIMENTS

The present invention relates to a crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide, and a crystal thereof with an acid (crystal of a salt thereof or co-crystal).

(I)

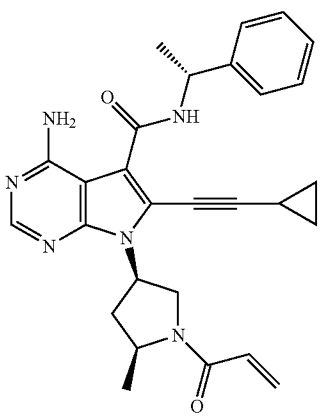

Specifically, the present invention relates to a type II crystal with 1 equivalent of fumaric acid, a free-form type II crystal, a free-form type I crystal, a type V crystal with 1 equivalent of fumaric acid, a type I crystal with 1 equivalent of fumaric acid, a type I crystal with 0.5 equivalents of fumaric acid, a type II crystal with 0.5 equivalents of fumaric acid of the compound (I).

In the present description, type I, type II, type III, type IV, and type V are convenient names for distinguishing the crystal forms, and the crystals according to the present invention are not limited by these names.

In the present description, a crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (compound (I)) with an acid means a salt crystal or a co-crystal with an acid. A salt crystal is a crystal in which a compound (I) and an acid molecule are bonded by an ionic bond, and a co-crystal is a crystal in which a compound (I) and an acid molecule are bonded by a nonionic interaction. In the present invention, a crystal of a compound (I) with an acid may be a salt crystal or a co-crystal, and includes the meanings of both. For example, a type II crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid means a crystal of fumarate of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide or a co-crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid.

A crystal represents a solid in which atoms and molecules have regular repeating structures, and is different from an amorphous solid having no repeating structures. Crystalline or amorphous solids can be examined by methods such as powder X-ray diffraction analysis (XRD analysis), differential scanning calorimetry (DSC analysis), simultaneous thermogravimetry-differential thermal analysis (TG-DTA analysis), and single crystal analysis. It is known that a crystal polymorph indicates that molecules are the same but the arrangement of atoms and molecules is different in a crystal, and the peaks obtained by XRD analysis are different among crystal polymorphs. It is also known that each polymorph has different solubility, oral absorbability, stability, and the like.

In the present description, the terms "crystal" and "amorphous" are used in the usual meaning.

In the present description, the description "compound (I)" simply means 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide, which is used in the meaning including both "amorphous" and "crystal."

In the present description, the description "crystal of compound (I)" is used in the meaning including any of free-form crystals of compound (I) and crystals of compound (I) with an acid (salt crystal of compound (I) and co-crystal of compound (I)).

In the present description, a crystal for which molecules other than the compound (I) constituting the crystal (other molecules constituting a salt or co-crystal) have not been specified means a free-form crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (compound (I)).

In the present description, the term "equivalent" means "molar equivalent."

In a crystal of compound (I) with an acid (a salt-form crystal or co-crystal), the equivalent of the acid to the compound (I) can be analyzed, for example, by NMR or ion chromatography.

In the present description, crystals may be hydrates.

In addition, the present invention also encompasses a labeled compound (I) or salt thereof, i.e., a compound obtained by substituting one or more atoms of a compound (I) or a salt thereof with radioactive or non-radioactive isotopes.

As long as the crystal contains a crystal of compound (I), it may be solely one type of crystal of compound (I) or may be a polymorphic mixture containing another type of crystal of compound (I) in addition to one type of crystal of compound (I). Specifically, it is preferable that the purity of the crystal is 50% by weight or more, that is to say, 50% by weight or more is a single crystal. It is more preferable that the purity of the crystal is 75% by weight or more, that is to say, 75% by weight or more is a single crystal. It is still more preferable that the purity of the crystal is 90% by weight or more, that is to say, 90% by weight or more is a single crystal. It is even more preferable that the purity of the crystal is 95% by weight or more, that is to say, 95% by weight or more is a single crystal. It is particularly preferable that the purity of the crystal is 99% by weight or more, that is to say, 99% by weight or more is a single crystal.

In the present description, the chemical purity is the purity measured by high performance liquid chromatography (HPLC), and when it is described as the chemical purity of the compound (I), it means the purity when the compound (I) is measured by high performance liquid chromatography. At that time, the wavelength of the detector used for the purity measurement can be appropriately set. Specifically, the chemical purity of compound (I) is preferably 95% or more, more preferably 98% or more, and particularly preferably 99% or more.

For powder X-ray diffraction patterns, the diffraction angle and the overall pattern are important when recognizing the crystal identity due to the nature of data. The relative intensity of a powder X-ray diffraction pattern may vary slightly depending on the direction of crystal growth, particle size, and measurement conditions, and thus should not be strictly understood.

Numerical values obtained from various patterns may have some errors depending on the direction of crystal growth, particle size, measurement conditions, and the like. Therefore, in the present description, the numerical value of a diffraction angle (2θ) in a powder X-ray diffraction pattern may have a measurement error in a range of approximately ±0.2°.

In the present description, "room temperature" generally means from approximately 10° C. to approximately 35° C.

In addition, the endothermic peak in a simultaneous thermogravimetry-differential thermal analysis (TG-DTA) curve generally means a value with a measurement error in a range of approximately ±5.0° C. because the measurement temperature may vary depending on the range of temperature increase per minute, the chemical purity of a sample, and the like. Therefore, when the crystal according to the present invention is measured (TG-DTA), an error of the peak (peak top value) of ±5.0° C. is taken into consideration. The term "around" used in such case means±5.0° C.

One embodiment of the present invention relates to a free-form crystal (type I crystal or type II crystal) of the compound (I), a crystal (type I crystal, type II crystal, type III crystal, type IV crystal, or type V crystal) of the compound (I) with 1 equivalent of fumaric acid, and a crystal (type I crystal or type II crystal) of the compound (I) with 0.5 equivalents of fumaric acid.

(Type II Crystal of Compound (I) with 1 Equivalent of Fumaric Acid)

A type II crystal of compound (I) with 1 equivalent of fumaric acid has the powder X-ray diffraction spectrum shown in FIG. 1, and also have the simultaneous thermogravimetry-differential thermal analysis (TG-DTA) curve shown in FIG. 2.

In addition, in one embodiment of the present invention, the type II crystal of compound (I) with 1 equivalent of fumaric acid has the diffraction angle (2θ) and intensity (cts) shown in Table 2 in powder X-ray diffraction.

Here, characteristic peaks in the powder X-ray diffraction spectrum of the type II crystal of compound (I) with 1 equivalent of fumaric acid may have diffraction angles (2θ±0.2°) of 5.5°, 6.8°, 9.3°, 13.4°, 15.3°, 16.3°, 18.5°, 19.8°, 22.0°, and 24.5°.

The type II crystal of compound (I) with 1 equivalent of fumaric acid according to the present invention is a crystal having three or more peaks selected from the above characteristic peaks. It is preferably a crystal having four or more peaks selected from the characteristic peaks, more preferably a crystal having five or more peaks selected from the characteristic peaks, still more preferably a crystal having six or more peaks selected from the characteristic peaks, still more preferably a crystal having seven or more peaks selected from the characteristic peaks, even more preferably a crystal having eight or more peaks selected from the characteristic peaks, still even more preferably a crystal having nine or more peaks selected from the characteristic peaks, and particularly preferably a crystal having all of the peaks.

The endothermic peak (peak top value) of the type II crystal of compound (I) with 1 equivalent of fumaric acid determined by simultaneous thermogravimetry-differential thermal analysis may be 173° C. to 183° C., in other words, around 178° C.

(Free-Form Type II Crystal of Compound (I))

A type II crystal of compound (I) has the powder X-ray diffraction spectrum shown in FIG. 3, and also have the simultaneous thermogravimetry-differential thermal analysis (TG-DTA) curve shown in FIG. 4.

In addition, in one embodiment of the present invention, the free-form type II crystal of compound (I) has the diffraction angle (2θ) and intensity (cts) shown in Table 3 in powder X-ray diffraction.

Here, characteristic peaks in the powder X-ray diffraction spectrum of the type II crystal of compound (I) may have diffraction angles (2θ±0.2°) of 8.3°, 14.8°, 17.3°, 18.0°, 19.1°, 20.3°, 21.0°, 22.5°, 23.0°, and 26.2°.

The type II crystal of compound (I) according to the present invention is a crystal having three or more peaks selected from the above characteristic peaks. It is preferably a crystal having four or more peaks selected from the characteristic peaks, more preferably a crystal having five or more peaks selected from the characteristic peaks, still more preferably a crystal having six or more peaks selected from the characteristic peaks, still more preferably a crystal having seven or more peaks selected from the characteristic peaks, even more preferably a crystal having eight or more peaks selected from the characteristic peaks, still even more preferably a crystal having nine or more peaks selected from the characteristic peaks, and particularly preferably a crystal having all of the characteristic peaks.

The endothermic peak (peak top value) of the type II crystal of compound (I) determined by simultaneous thermogravimetry-differential thermal analysis may be 177° C. to 187° C., in other words, around 182° C.

(Free-Form Type I Crystal of Compound (I))

A type I crystal of compound (I) has the powder X-ray diffraction spectrum shown in FIG. 5, and also have the simultaneous thermogravimetry-differential thermal analysis (TG-DTA) curve shown in FIG. 6.

In addition, in one embodiment of the present invention, the free-form type I crystal of compound (I) has the diffraction angle (2θ) and intensity (cts) shown in Table 4 in powder X-ray diffraction.

Here, characteristic peaks in the powder X-ray diffraction spectrum of the type I crystal of compound (I) may have diffraction angles (2θ±0.2°) of 9.9°, 11.7°, 13.2°, 17.7°, 18.1°, 18.8°, and 20.8°.

The type I crystal of compound (I) according to the present invention is a crystal having three or more peaks selected from the above characteristic peaks. It is preferably a crystal having four or more peaks selected from the characteristic peaks, more preferably a crystal having five or more peaks selected from the characteristic peaks, still more preferably a crystal having six or more peaks selected from the characteristic peaks, and particularly preferably a crystal having all of the characteristic peaks.

Here, characteristic peaks in the powder X-ray diffraction spectrum of the type I crystal of compound (I) may have diffraction angles (2θ±0.2°) of 9.9°, 11.7°, 13.2°, 18.8°, and 20.8°.

The type I crystal of compound (I) according to the present invention is a crystal having three or more peaks selected from the above characteristic peaks. It is preferably a crystal having four or more peaks selected from the characteristic peaks, and particularly preferably a crystal having all of the characteristic peaks.

The endothermic peak (peak top value) of the type I crystal of compound (I) determined by simultaneous thermogravimetry-differential thermal analysis may be 178° C. to 188° C., in other words, around 183° C.

(Type V Crystal of Compound (I) with 1 Equivalent of Fumaric Acid)

A type V crystal of compound (I) with 1 equivalent of fumaric acid has the powder X-ray diffraction spectrum shown in FIG. 7, and also have the simultaneous thermogravimetry-differential thermal analysis (TG-DTA) curve shown in FIG. 8.

In addition, in one embodiment of the present invention, the type V crystal of compound (I) with 1 equivalent of fumaric acid has the diffraction angle (2θ) and intensity (cts) shown in Table 5 in powder X-ray diffraction.

Here, characteristic peaks in the powder X-ray diffraction spectrum of the type V crystal of compound (I) with 1 equivalent of fumaric acid may have diffraction angles (2θ±0.2°) of 6.9°, 9.4°, 10.2°, 13.7°, 21.1°, 23.6°, and 26.5°.

The type V crystal of compound (I) with 1 equivalent of fumaric acid according to the present invention is a crystal having three or more peaks selected from the above characteristic peaks. It is preferably a crystal having four or more peaks selected from the characteristic peaks, more preferably a crystal having five or more peaks selected from the characteristic peaks, still more preferably a crystal having six or more peaks selected from the characteristic peaks, and particularly preferably a crystal having all of the characteristic peaks.

Here, characteristic peaks in the powder X-ray diffraction spectrum of the type V crystal of compound (I) with 1 equivalent of fumaric acid may have diffraction angles (2θ±0.2°) of 6.9°, 13.7°, 21.1°, 23.6°, and 26.5°.

The type V crystal of compound (I) with 1 equivalent of fumaric acid according to the present invention is a crystal having three or more peaks selected from the above characteristic peaks. It is preferably a crystal having four or more peaks selected from the characteristic peaks, and particularly preferably a crystal having all of the characteristic peaks.

The endothermic peak (peak top value) of the type V crystal of compound (I) with 1 equivalent of fumaric acid determined by simultaneous thermogravimetry-differential thermal analysis may be 146° C. to 156° C., in other words, around 151° C.

(Type I Crystal of Compound (I) with 1 Equivalent of Fumaric Acid)

A type I crystal of compound (I) with 1 equivalent of fumaric acid has the powder X-ray diffraction spectrum shown in FIG. 9, and also have the simultaneous thermogravimetry-differential thermal analysis (TG-DTA) curve shown in FIG. 10.

In addition, in one embodiment of the present invention, the type I crystal of compound (I) with 1 equivalent of fumaric acid has the diffraction angle (2θ) and intensity (cts) shown in Table 6 in powder X-ray diffraction.

Here, characteristic peaks in the powder X-ray diffraction spectrum of the type V crystal of compound (I) with 1 equivalent of fumaric acid may have diffraction angles (2θ±0.2°) of 6.4°, 10.3°, 12.8°, 15.0°, 20.7°, 23.4°, and 26.6°.

The type I crystal of compound (I) with 1 equivalent of fumaric acid according to the present invention is a crystal having three or more peaks selected from the above characteristic peaks. It is preferably a crystal having four or more peaks selected from the characteristic peaks, more preferably a crystal having five or more peaks selected from the characteristic peaks, still more preferably a crystal having five or more peaks selected from the characteristic peaks, and particularly preferably a crystal having all of the characteristic peaks.

The endothermic peak (peak top value) of the type I crystal of compound (I) with 1 equivalent of fumaric acid determined by simultaneous thermogravimetry-differential thermal analysis may be 148° C. to 158° C., in other words, around 153° C.

Here, characteristic peaks in the powder X-ray diffraction spectrum of the type V crystal of compound (I) with 1 equivalent of fumaric acid may have diffraction angles (2θ±0.2°) of 6.4°, 10.3°, 12.8°, 20.7°, 23.4°, and 26.6°.

The type I crystal of compound (I) with 1 equivalent of fumaric acid according to the present invention is a crystal having three or more peaks selected from the above characteristic peaks. It is preferably a crystal having four or more peaks selected from the characteristic peaks, more preferably a crystal having five or more peaks selected from the characteristic peaks, and particularly preferably a crystal having all of the characteristic peaks.

The endothermic peak (peak top value) of the type I crystal of compound (I) with 1 equivalent of fumaric acid determined by simultaneous thermogravimetry-differential thermal analysis may be 148° C. to 158° C., in other words, around 153° C.

(Type I Crystal of Compound (I) with 0.5 Equivalents of Fumaric Acid)

A type I crystal of compound (I) with 0.5 equivalents of fumaric acid has the powder X-ray diffraction spectrum shown in FIG. 11, and also have the simultaneous thermogravimetry-differential thermal analysis (TG-DTA) curve shown in FIG. 12.

Here, characteristic peaks in the powder X-ray diffraction spectrum of the type I crystal of compound (I) with 0.5 equivalents of fumaric acid may have diffraction angles (2θ±0.2°) of 6.4°, 7.5°, 9.7°, 11.7°, 15.1°, 19.6°, and 23.9°.

The type I crystal of compound (I) with 0.5 equivalents of fumaric acid according to the present invention is a crystal having four or more peaks selected from the above characteristic peaks. It is preferably a crystal having five or more peaks selected from the characteristic peaks, more preferably a crystal having six or more peaks selected from the characteristic peaks, and particularly preferably a crystal having all of the characteristic peaks.

The endothermic peak (peak top value) of the type I crystal of compound (I) with 0.5 equivalents of fumaric acid determined by simultaneous thermogravimetry-differential thermal analysis may be 156° C. to 166° C., in other words, around 161° C.

(Type II Crystal of Compound (I) with 0.5 Equivalents of Fumaric Acid)

A type II crystal of compound (I) with 0.5 equivalents of fumaric acid has the powder X-ray diffraction spectrum shown in FIG. 13, and also have the simultaneous thermogravimetry-differential thermal analysis (TG-DTA) curve shown in FIG. 14.

Here, characteristic peaks in the powder X-ray diffraction spectrum of the type II crystal of compound (I) with 0.5 equivalents of fumaric acid may have diffraction angles (2θ±0.2°) of 5.4°, 6.4°, 7.3°, 12.8°, 13.4°, 14.7°, and 15.4°.

The type II crystal of compound (I) with 0.5 equivalents of fumaric acid according to the present invention is a crystal having four or more peaks selected from the above characteristic peaks. It is preferably a crystal having five or more peaks selected from the characteristic peaks, more preferably a crystal having six or more peaks selected from the characteristic peaks, and particularly preferably a crystal having all of the characteristic peaks.

The endothermic peak (peak top value) of the type II crystal of compound (I) with 0.5 equivalent of fumaric acid determined by simultaneous thermogravimetry-differential thermal analysis may be 157° C. to 167° C., in other words, around 162° C.

(Type III Crystal of Compound (I) with 1 Equivalents of Fumaric Acid)

A type III crystal of compound (I) with 1 equivalents of fumaric acid has the powder X-ray diffraction spectrum shown in FIG. 15, and also have the simultaneous thermogravimetry-differential thermal analysis (TG-DTA) curve shown in FIG. 16.

Here, characteristic peaks in the powder X-ray diffraction spectrum of the type III crystal of compound (I) with 1 equivalent of fumaric acid may have diffraction angles (2θ±0.2°) of 8.1°, 13.2°, 20.4°, 23.1°, 24.7°, and 26.1°.

The type III crystal of compound (I) with 1 equivalent of fumaric acid according to the present invention is a crystal having three or more peaks selected from the above characteristic peaks. It is preferably a crystal having four or more peaks selected from the characteristic peaks, more preferably a crystal having five or more peaks selected from the characteristic peaks, and particularly preferably a crystal having all of the characteristic peaks.

The exothermic peak (peak top value) of the type III crystal of compound (I) with 1 equivalent of fumaric acid determined by simultaneous thermogravimetry-differential thermal analysis may be 148° C. to 158° C., in other words, around 153° C.

(Type IV Crystal of Compound (I) with 1 Equivalent of Fumaric Acid)

A type IV crystal of compound (I) with 1 equivalent of fumaric acid has the powder X-ray diffraction spectrum shown in FIG. 17, and also have the simultaneous thermogravimetry-differential thermal analysis (TG-DTA) curve shown in FIG. 18.

Here, characteristic peaks in the powder X-ray diffraction spectrum of the type IV crystal of compound (I) with 1 equivalent of fumaric acid may have diffraction angles (2θ±0.2°) of 6.0°, 15.7°, and 18.8°.

The type IV crystal of compound (I) with 1 equivalent of fumaric acid according to the present invention is a crystal having all of the above characteristic peaks.

The exothermic peak (peak top value) of the type IV crystal of compound (I) with 1 equivalent of fumaric acid determined by simultaneous thermogravimetry-differential thermal analysis may be 125° C. to 135° C., in other words, around 130° C.

(Method for Producing Type II Crystal with 1 Equivalent of Fumaric Acid)

In one embodiment of the present description, a type II crystal of compound (I) with 1 equivalent of fumaric acid can be obtained by a method comprising, for example, the following two steps.

Step 1: Step of adding fumaric acid and the following solvent to a type I crystal of compound (I) and optionally adding a seed crystal.

Step 2: Step of stirring the suspension obtained in the above step to obtain a crystal of compound (I) with 1 equivalent of fumaric acid.

Thereafter, the resulting solid was recovered by filtration. It is preferable that the recovered solid is washed with water and dried.

In step 1, preferably 1.5 to 10 equivalents (more preferably 2 to 5 equivalents and most preferably 3 equivalents) of fumaric acid is added with respect to 1 equivalent of a free-form compound (I).

The solvent in step 1 is added in an amount of preferably 5 to 35 times (v/w) (more preferably 5 to 30 times (v/w) and most preferably 10 times (v/w)).

Examples of the solvent used in step 1 may include single solvents or mixed solvents of alcohols such as methanol, ethanol, isopropanol, and tert-butanol, ethers such as 1,4-dioxane and tetrahydrofuran, ketones such as acetone and methyl ethyl ketone, and aprotic polar solvents such as acetonitrile.

A type I crystal of compound (I) can be obtained in the section of "(Method for producing free-form type I crystal)" or the method described later in Example 3.

The temperature during the reaction in step 2 is preferably room temperature or higher and lower than the boiling point of each solvent as described above, but is not particularly limited and can be appropriately set to preferably 25° C. to 70° C. (more preferably 40° C. to 60° C. and most preferably 50° C.).

The stirring time during the reaction in step 2 is preferably 24 to 124 hours (more preferably 48 to 72 hours and most preferably 60 to 65 hours) for stirring the suspension.

(Method for Producing Free-Form Type II Crystal)

(Method A-1)

In one embodiment of the present description, a free-form type II crystal of compound (I) can be obtained by a method comprising, for example, the following two steps (Method A-1).

Step 1: Step of adding any one of succinic acid, phosphoric acid, and adipic acid and a mixed solvent of good solvent/poor solvent to the compound (I), and optionally adding a seed crystal.

Step 2: Step of stirring the suspension obtained in the above step to obtain a crystal of compound (I) in a solid form.

During suspension and stirring described above, an additional solvent (for example, 1-propanol as a good solvent) may be added in a plurality of times as necessary, depending on the amount of evaporation of the solvent.

Thereafter, the resulting solid was recovered by filtration and dried.

Preferably 0.5 to 2 equivalents (more preferably 0.75 to 1.5 equivalents and particularly preferably 1 equivalent) of the acid in step 1 is added with respect to 1 equivalent of the compound (I).

The mixed solvent of good solvent/poor solvent in step 1 (e.g., 1-propanol/water) is added in an amount of preferably 5 to 50 times (v/w) (more preferably 10 to 30 times (v/w) and particularly preferably 20 times (v/w)) the amount of the free-form compound (I).

The temperature during the reaction in step 2 is preferably 25° C. to 70° C. (more preferably 40° C. to 60° C. and particularly preferably 50° C.).

The stirring time during the reaction in step 2 is preferably 2 to 7 days (more preferably 3 to 5 days and particularly preferably 4 days) for stirring the suspension.

(Method A-2)

In another embodiment of the present description, a free-form type II crystal of compound (I) can be obtained by a method comprising, for example, the following two steps (Method A-2).

Step 1: Step of adding a mixed solvent of good solvent/poor solvent and a seed crystal to the compound (I), and optionally adding any one of succinic acid, phosphoric acid, and adipic acid.

Step 2: Step of stirring the suspension obtained in the above step to obtain a crystal of compound (I) in a solid form.

During suspension and stirring described above, an additional solvent (for example, 1-propanol as a good solvent) may be added in a plurality of times as necessary, depending on the amount of evaporation of the solvent.

Thereafter, the resulting solid was recovered by filtration and dried.

Preferably 0.5 to 2 equivalents (more preferably 0.75 to 1.5 equivalents and particularly preferably 1 equivalent) of succinic acid in step 1 is added with respect to 1 equivalent of the compound (I).

The mixed solvent of good solvent/poor solvent in step 1 (e.g., a mixed solvent of 1-propanol/water) is added in an amount of preferably 1 to 10 times (v/w) (more preferably 2 to 5 times (v/w) and particularly preferably 3 times (v/w)) the amount of the free-form compound (I), and a seed crystal (e.g., a seed crystal obtained in either (i) or (ii)) is added thereto.

The reaction temperature in step 2 is preferably 25° C. to 70° C. (more preferably 40° C. to 60° C. and particularly preferably 50° C.).

The reaction time in step 2 is preferably 6 to 48 hours (more preferably 12 to 24 hours and most preferably 17.5 to 24 hours).

(Method B)

In another embodiment of the present description, a free-form type II crystal of compound (I) can be obtained by a method comprising, for example, the following two steps (Method B).

Step 1: Step of adding a poor solvent to the compound (I) and optionally adding a seed crystal.

Step 2: Step of adding a good solvent to the solution obtained in the above step and stirring the resulting suspension to obtain a crystal of compound (I) in a solid form.

The poor solvent (e.g., diisopropyl ether) in step 1 is added in an amount of preferably 2 to 10 times (v/w) (more preferably 3 to 7 times (v/w) and particularly preferably 5 times (v/w)) the amount of the free-form compound (I).

The reaction time in step 1 is preferably 24 to 96 hours (more preferably 36 to 72 hours and particularly preferably 44.5 hours) for suspension and stirring.

The reaction temperature in step 2 is preferably 25° C. to 70° C. (more preferably 40° C. to 60° C. and particularly preferably 50° C.).

The good solvent in step 2 (e.g., ethanol) is added in an amount of preferably 0.5 to 3 times (v/w) (more preferably 0.8 to 2 times (v/w) and particularly preferably 1 time (v/w)) the amount of the free-form compound (I).

The stirring time in step 2 is preferably 6 to 72 hours (more preferably 12 to 48 hours and particularly preferably 21 hours), following which the solid is recovered by filtration and dried.

During suspension and stirring described above, an additional solvent (e.g., diisopropyl ether as a poor solvent and/or ethanol as a good solvent) may be added in a plurality of times as necessary according to the amount of evaporation of the solvent.

Examples of a combination of a good solvent and a poor solvent used in the production of a free form II crystal of compound (I) include methanol (good solvent) and water (poor solvent), methanol (good solvent) and diisopropyl ether (IPE) (poor solvent), methanol (good solvent) and heptane (poor solvent), ethanol (good solvent) and IPE (poor solvent), ethanol (good solvent) and heptane (poor solvent), 1-propanol (good solvent) and water (poor solvent), 1-propanol (good solvent) and IPE (poor solvent), 1-propanol (good solvent) and heptane (poor solvent), 2-propanol (good solvent) and heptane (poor solvent), acetone (good solvent) and IPE (poor solvent), acetone (good solvent) and heptane (poor solvent), dimethyl sulfoxide (DMSO) (good solvent) and water (poor solvent), dimethylacetamide (DMA) (good solvent) and water (poor solvent), tetrahydrofuran (THF) (good solvent) and IPE (poor solvent), and THF (good solvent) and heptane (poor solvent).

Of these, a preferred combination of a good solvent and a poor solvent is ethyl acetate (good solvent) and n-heptane (poor solvent), ethanol (good solvent) and water (poor solvent), 1-propanol (good solvent) and water (poor solvent), or ethanol (good solvent) and diisopropyl ether (poor solvent). The amount of the poor solvent is preferably 1 to 20 times (v/v) and more preferably 1 to 10 times (v/v) of the good solvent.

In the above method, the amount of the seed crystal added can be preferably 0.5% to 30% (w/w), more preferably 1% to 5% (w/w) of the amount of the introduced compound (I).

(Method for Producing Free-Form Type I Crystal)

In one embodiment of the present description, a free-form type I crystal of compound (I) can be obtained by a method comprising, for example, a step of suspending a crude product of the compound (I) in a solvent and optionally adding a seed crystal to obtain a crystal of compound (I) in a solid form.

The seed crystal is optionally added in order to promote the crystallization of the free-form type I crystal, and as the seed crystal, an appropriate amount of a type I crystal of compound (I) or a mixed crystal containing the type I crystal may be added. A type I crystal of compound (I) can be obtained by the above method without adding a seed crystal. However, by adding a seed crystal, the time for obtaining the compound can be shortened. Further, crystallization may be carried out with stirring in order to shorten the crystallization time and control the particle size.

The seed crystal to be added is 0.5% to 30% (w/w) and preferably 1% to 10% (w/w) of the amount of the introduced compound (I).

The temperature can be appropriately set, but is preferably 50° C. to 65° C.

The compound (I) can be precipitated at the above dissolution temperature. However, if it is not precipitated at the dissolution temperature, a free-form type I crystal can be obtained by cooling to 25° C.

As the solvent, ethyl acetate, ethanol, acetonitrile, acetone, tert-butyl methyl ether, or the like can be used.

(Method for Producing Type V Crystal with 1 Equivalent of Fumaric Acid)

In one embodiment of the present description, a type V crystal of compound (I) with 1 equivalent of fumaric acid can be obtained by a method comprising, for example, the following two steps.

Step 1: Step of to the compound (I), adding 1 to 2 equivalents of fumaric acid and acetone as a solvent in an amount 40 to 60 times (v/w) with respect to 1 equivalent of the free-form compound (I) and optionally adding a seed crystal.

Step 2: Step of stirring the suspension obtained in the above step, filtrating the suspension, and recovering the solid.

Step 3: Step of drying the solid obtained in the above step under reduced pressure conditions (preferably a pressure of 2 kPa or less) at preferably 20° C. to 60° C. to obtain a crystal of compound (I) with 1 equivalent of fumaric acid.

Fumaric acid in step 1 is more preferably added in an amount of 2 equivalents to 1 equivalent of the free-form compound (I).

Acetone in step 1 is preferably added in an amount 40 to 60 times (v/w) (more preferably 50 times (v/w)) with respect to the free-form compound (I).

The reaction temperature in step 2 is preferably 10° C. to 30° C. (preferably 25° C.). The reaction time in step 2 is preferably 12 to 96 hours (more preferably 71 hours).

The reaction temperature of step 3 is 20° C. to 60° C. (e.g., room temperature) for the obtained solid.

The reduced pressure time in step 3 (e.g., a pressure of 2 kPa or less) include drying for preferably 6 to 24 hours (more preferably 7.5 hours).

In one embodiment of the present description, a type V crystal of compound (I) with 1 equivalent of fumaric acid can be obtained by a method comprising, for example, the following step.

Step 1: Step of drying a type I crystal with 1 equivalent of fumaric acid under reduced pressure conditions (preferably at a pressure of 2 kPa or less).

The reaction temperature in step 1 is 20° C. to 60° C.

(Method for Producing Type I Crystal with 1 Equivalent of Fumaric Acid)

In one embodiment of the present description, a type I crystal of compound (I) with 1 equivalent of fumaric acid can be obtained by a method comprising, for example, the following two steps.

Step 1: Step of to the compound (I), adding 1 to 2 equivalents of fumaric acid and acetone as a solvent in an amount 40 to 60 times (v/w) with respect to 1 equivalent of the free form compound (I) and optionally adding a seed crystal.

Step 2: Step of stirring the suspension obtained in the above step at 30° C. or less to obtain a crystal of compound (I) with fumaric acid.

Thereafter, the resulting solid was recovered by filtration.

Fumaric acid in step 1 is more preferably added in an amount of 2 equivalents to 1 equivalent of the free-form compound (I).

Acetone in step 1 is preferably added in an amount 40 to 60 times (more preferably 50 times) with respect to the free-form compound (I).

The reaction temperature in step 2 is preferably 10° C. to 30° C. (preferably 25° C.). The reaction time in step 2 is preferably 12 to 24 hours (more preferably 19.5 hours).

(Method for Producing Type III Crystal with 1 Equivalent of Fumaric Acid)

In one embodiment of the present description, a type III crystal of compound (I) with 1 equivalent of fumaric acid can be obtained by a method comprising, for example, the following two steps.

Step 1: Step of adding fumaric acid and acetonitrile as a solvent to the compound (I) and optionally adding a seed crystal.

Step 2: Step of stirring the suspension obtained in the above step in a short time of 1.5 hours or less to obtain a crystal of compound (I) with 1 equivalent of fumaric acid.

Thereafter, the resulting solid was recovered by filtration.

To 1 equivalent of the free-form compound (I) in step 1, preferably 1 to 5 equivalents (more preferably 3 equivalents) of fumaric acid is added.

The solvent (e.g., acetonitrile) in step 1 is preferably added in an amount 25 to 35 times (v/w) (more preferably 30 times (v/w)) with respect to the free-form compound (I).

The reaction temperature in step 2 is preferably 45° C. to 55° C. (particularly preferably 50° C.).

The reaction time in step 2 is preferably 0.5 to 1.5 hours (more preferably 1 hour).

(Method for Producing Type IV Crystal with 1 Equivalent of Fumaric Acid)

In one embodiment of the present description, a type IV crystal of compound (I) with 1 equivalent of fumaric acid can be obtained by a method comprising, for example, the following two steps.

Step 1: Step of adding fumaric acid and water as a solvent to the compound (I) and optionally adding a seed crystal.

Step 2: Step of stirring the suspension obtained in the above step in a short time of 2 hours or less to obtain a crystal of compound (I) with 1 equivalent of fumaric acid.

Thereafter, the resulting solid was recovered by filtration.

To 1 equivalent of the free-form compound (I), preferably 1 to 5 equivalents (more preferably 3 equivalents) of fumaric acid is added in step 1.

Water as the solvent in step 1 is added in an amount preferably 15 to 25 times (more preferably 20 times) with respect to the free-form compound (I).

The reaction temperature in step 2 is preferably 45° C. to 55° C. (particularly preferably 50° C.).

The reaction time in step 2 is preferably 1 to 2 hours (more preferably 1.5 hour).

(Method for Producing Type I Crystal with 0.5 Equivalent of Fumaric Acid)

In one embodiment of the present description, a type I crystal of compound (I) with 0.5 equivalents of fumaric acid can be obtained by a method comprising, for example, the following two steps.

Step 1: Step of adding fumaric acid and water as a solvent to the compound (I) and optionally adding a seed crystal.

Step 2: Step of stirring the suspension obtained in the above step at a temperature of preferably room temperature or higher and lower than the boiling point of the solvent to obtain a crystal.

Thereafter, the resulting solid was recovered by filtration and dried.

In step 1, preferably 0.5 to 1 equivalent (more preferably 0.5 to 0.75 equivalents and most preferably 0.5 equivalents) of fumaric acid is added with respect to 1 equivalent of the free-form compound (I).

Water as the solvent in step 1 is added in an amount of preferably 10 to 40 times (v/w) (more preferably 15 to 25 times (v/w) and most preferably 20 times (v/w)) with respect to the free-form compound (I).

The reaction temperature in step 2 is preferably 40° C. to 60° C. (more preferably 45° C. to 55° C. and particularly preferably 50° C.).

The reaction time in step 2 is preferably 48 to 120 hours (more preferably 72 to 96 hours and most preferably 93.5 hours).

(Method for Producing Type II Crystal with 0.5 Equivalents of Fumaric Acid)

In one embodiment of the present description, a type II crystal of compound (I) with 0.5 equivalents of fumaric acid can be obtained by a method comprising, for example, the following two steps.

Step 1: Step of adding fumaric acid and ethanol to the compound (I) and optionally adding a seed crystal.

Step 2: Step of stirring the suspension obtained in the above step at a temperature of preferably room temperature or higher and lower than the boiling point of the solvent to obtain a crystal.

Thereafter, the resulting solid was recovered by filtration and dried.

To 1 equivalent of the free-form compound (I), preferably 0.5 to 1 equivalent (more preferably 1 equivalent) of fumaric acid is added in step 1.

Ethanol as the solvent in step 1 is added in an amount of preferably 10 to 40 times (v/w) (more preferably 15 to 25 times (v/w) and most preferably 20 times (v/w)) with respect to the free-form compound (I).

The reaction temperature in step 2 is preferably 40° C. to 60° C. (more preferably 45° C. to 55° C. and particularly preferably 50° C.).

The reaction time in step 2 is preferably 6 to 48 hours (more preferably 12 to 24 hours and most preferably 19.5 hours).

A type II crystal with 1 equivalent of fumaric acid, a free-form type II crystal, a free-form type I crystal, a type V crystal with 1 equivalent of fumaric acid, a type I crystal with 0.5 equivalents of fumaric acid, and a type II crystal with 0.5 equivalents of fumaric acid of the compound (I) have at least one of advantageous properties in pharmaceutical manufacturing such as a non-hygroscopic property, ability to be obtained with reproducibility, solid stability, and oral absorbability.

Of these, a type II crystal with 1 equivalent of fumaric acid, a free-form type II crystal, a free-form type I crystal, and a type V crystal with 1 equivalent of fumaric acid of the compound (I) have advantageous properties in pharmaceutical manufacturing such as a non-hygroscopic property, ability to be obtained with reproducibility, solid stability, and oral absorbability, as compared with other crystal forms of the compound (I).

The type II crystal of compound (I) with 1 equivalent of fumaric acid is less hygroscopic and has ability to be obtained with stability. It is important for the industrial manufacturing of pharmaceutical products that drug development candidate compounds are less hygroscopic can be stably obtained. In addition, it has properties that are easy to handle as pharmaceutical products, such as solid stability and solubility, and excellent oral absorbability Therefore, the type II crystal of compound (I) with 1 equivalent of fumaric acid has excellent properties required as a pharmaceutical product or active pharmaceutical ingredient.

The free-form type II crystal of compound (I) is less hygroscopic. It is important for the industrial manufacturing of pharmaceutical products having stable quality with drug development candidate compounds. In addition, it has properties that are easy to handle as pharmaceutical products, such as solid stability and solubility, and excellent oral absorbability Therefore, the free-form crystal of compound (I) has excellent properties required as a pharmaceutical product or active pharmaceutical ingredient.

The free-form type I crystal of compound (I) is less hygroscopic and has excellent ability to be obtained with stability. It is also important for the industrial manufacturing of pharmaceutical products with stable quality that drug development candidate compounds are less hygroscopic and have ability to be stably obtained. Therefore, the type I crystal of compound (I) has excellent properties required as a pharmaceutical product or active pharmaceutical ingredient.

The type V crystal of compound (I) with 1 equivalent of fumaric acid is less hygroscopic and has ability to be obtained with stability. It is also important for the industrial manufacturing of pharmaceutical products with stable quality that drug development candidate compounds are less hygroscopic and have ability to be stably obtained. Therefore, the type V crystal of compound (I) with 1 equivalent of fumaric acid according to the present invention have excellent properties required as a pharmaceutical product or active pharmaceutical ingredient.

The type I crystal of compound (I) with 1 equivalent of fumaric acid has excellent ability to be stablly obtained. It is also important for the industrial manufacturing of pharmaceutical products with stable quality that drug development candidate compounds have ability to be stably obtained. Therefore, the type I crystal of compound (I) with 1 equivalent of fumaric acid has excellent properties required as a pharmaceutical product or active pharmaceutical ingredient.

Since the type I crystal of compound (I) with 1 equivalent of fumaric acid can be recovered as a solid from, it is also useful as an intermediate for the production of a type V crystal with 1 equivalent of fumaric acid.

The type III crystal of compound (I) with 1 equivalent of fumaric acid has excellent ability to be stably obtained. It is also important for the industrial manufacturing of pharmaceutical products with stable quality that drug development candidate compounds have ability to be stably obtained. Therefore, the type III crystal of compound (I) with 1 equivalent of fumaric acid has excellent properties required as a pharmaceutical product or active pharmaceutical ingredient.

The type IV crystal of compound (I) with 1 equivalent of fumaric acid has excellent ability to be stably obtained. It is also important for the industrial manufacturing of pharmaceutical products with stable quality that drug development candidate compounds have ability to be stably obtained. Therefore, the type IV crystal of compound (I) with 1 equivalent of fumaric acid has excellent properties required as a pharmaceutical product or active pharmaceutical ingredient.

The type I crystal of compound (I) with 0.5 equivalents of fumaric acid has excellent ability to be stably obtained. It is also important for the industrial manufacturing of pharmaceutical products with stable quality that drug development candidate compounds have ability to be stably obtained. Therefore, the type I crystal of compound (I) with 0.5 equivalents of fumaric acid has excellent properties required as a pharmaceutical product or active pharmaceutical ingredient.

The type II crystal of compound (I) with 0.5 equivalents of fumaric acid has excellent ability to be stably obtained. It is also important for the industrial manufacturing of pharmaceutical products with stable quality that drug development candidate compounds have ability to be stably obtained. Therefore, the type II crystal of compound (I) with 0.5 equivalents of fumaric acid according to the present invention have excellent properties required as a pharmaceutical product or active pharmaceutical ingredient.

(Crystals with Other Acids)

Another embodiment of the present invention relates to a crystal of compound (I) with hydrochloric acid (type I crystal, type II crystal, or type III crystal), a crystal of compound (I) with hydrobromic acid, a crystal of compound (I) with 1 equivalent of L-tartaric acid, or a crystal of compound (I) with succinic acid.

The powder X-ray diffraction spectra and simultaneous thermogravimetry-differential thermal analysis (TG-DTA) curves for these crystals are shown in FIGS. 19 to 30.

Characteristic peaks in the powder X-ray diffraction spectra of these crystals are described in Reference Examples 3 to 7. These crystals are crystals having three or more (preferably four or more, and if present, more preferably 5 or more) peaks selected from characteristic peaks described in the Reference Examples, and in particular, they are crystals having all of the characteristic peaks.

In addition, endothermic peak temperatures determined by simultaneous thermogravimetry-differential thermal analysis for these crystals are also described in the Reference Examples.

Regarding free-form crystals of the compound (I) and crystals of the compound (I) with an acid (salt crystal or co-crystal) as described above, a precipitated crystal can be isolated and purified from a solution in which the crystal is dissolved, mixed, or the like by a known separation and purification means such as filtration, washing with water, and drying under reduced pressure.

The free-form crystals or crystals with acids (salt crystals or co-crystals) of the compound (I) of the present invention has excellent HER2 inhibitory activity. Moreover, the free-form crystals or crystals with acids (salt crystals or co-crystals) of the compound (I) of the present invention has excellent selectivity to HER2. Accordingly, the free-form crystals or crystals with acids (salt crystals or co-crystals) of the compound (I) of the present invention is useful as an antitumor agent against diseases or malignant tumor having HER2 overexpression, HER2 gene amplification, HER2 mutation, etc. In addition, the free-form crystals or crystals with acids (salt crystals or co-crystals) of the compound (I) of the present invention is advantageous in that it has a few side effects.

In the present description, the term "HER2" includes the HER2 of a human or a non-human mammal, and it is preferably human HER2. Furthermore, the term "HER2" includes isoforms.

Since the free-form crystals or crystals with acids (salt crystals or co-crystals) of the compound (I) of the present invention has excellent HER2 inhibitory activity, it is useful as a medicament for treating disease associated with HER2.

The "disease associated with HER2" means disease, in which a reduction in the incidence, or the remission, alleviation and/or complete recovery of the symptoms thereof is achieved by deleting, suppressing and/or inhibiting the function of HER2. Examples of such disease may include malignant tumors, but are not limited thereto. Preferred examples of the disease may include malignant tumors having HER2 overexpression, HER2 gene amplification, or HER2 mutation.

The free-form crystals or crystals with acids (salt crystals or co-crystals) of the compound (I) of the present invention selectively inhibits wild-type HER2, and mutant HER2 having one or more insertion mutations, point mutations, deletion mutations, etc. in the HER2 domain thereof, such as exon 20 insertion mutation.

One embodiment of the present invention provides: the free-form crystals or crystals with acids (salt crystals or co-crystals) of the compound (I) having inhibitory activity against wild-type HER2, and mutant HER2 including HER2 having YVMA insertion mutation that is one of exon 20 insertion mutations, or a salt thereof; or a medicament or a pharmaceutical composition each comprising the same.

One embodiment of the present invention provides an inhibitor against wild-type HER2, and mutant HER2 including HER2 having YVMA insertion mutation, etc., wherein the inhibitor comprises the free-form crystals or crystals with acids (salt crystals or co-crystals) of the compound (I) of the present invention.

The human HER2 gene is shown in, for example, SEQ ID NO: 1, SEQ ID NO: 3, or SEQ ID NO: 5. The wild-type HER2 protein consists of the amino acid sequence set forth in, for example, SEQ ID NO: 2, SEQ ID NO: 4, or SEQ ID NO: 6. The nucleotide sequence information of the human HER2 gene and the amino acid sequence information of the wild-type HER2 protein can be obtained from, for example, Accession No. NM_004448, NM_001289936, NM_001005862, or the like.

In several embodiments, the free-form crystals or crystals with acids (salt crystals or co-crystals) of the compound (I) of the present invention exhibits inhibitory activity against mutant HER2 comprising one or more mutations from G309A, S310F, R678Q, L755S, L755_T759del, D769H, A775_G776insYVMA, V777L, V8421 and R896C, using the amino acid sequence set forth in SEQ ID NO: 2 as a reference. In another embodiment, the free-form crystals or crystals with acids (salt crystals or co-crystals) of the compound (I) of the present invention exhibits inhibitory activity against mutant HER2 comprising A775_G776insYVMA, using the amino acid sequence set forth in SEQ ID NO: 2 as a reference.

In several embodiments, the free-form crystals or crystals with acids (salt crystals or co-crystals) of the compound (I) of the present invention exhibits inhibitory activity against mutant HER2 comprising one or more mutations from G294A, S295F, R663Q, L740S, L740_T744del, D754H, A760_G761insYVMA, V762L, V827I and R881C, using the amino acid sequence set forth in SEQ ID NO: 4 as a reference. In another embodiment, the free-form crystals or crystals with acids (salt crystals or co-crystals) of the compound (I) of the present invention exhibits inhibitory activity against mutant HER2 comprising A760_G761insYVMA, using the amino acid sequence set forth in SEQ ID NO: 4 as a reference.

In several embodiments, the free-form crystals or crystals with acids (salt crystals or co-crystals) of the compound (I) of the present invention exhibits inhibitory activity against mutant HER2 comprising one or more mutations from G279A, S280F, R648Q, L725S, L725_T729del, D739H, A745_G746insYVMA, V747L, V812I and R866C, using the amino acid sequence set forth in SEQ ID NO: 6 as a reference. In another embodiment, the free-form crystals or crystals with acids (salt crystals or co-crystals) of the compound (I) of the present invention exhibits inhibitory activity against mutant HER2 comprising A745_G746insYVMA, using the amino acid sequence set forth in SEQ ID NO: 6 as a reference.

Further, in several embodiments, with regard to a mutation in a certain HER2 isoform, even when the position of the mutation is different from the position of an amino acid shown in SEQ ID NO: 2 due to deletion or insertion of an amino acid(s), it is understood that the mutation is the same as the mutation at a position corresponding to the position of the amino acid shown in SEQ ID NO: 2. Hence, for example, the glycine at position 309 in the HER2 shown in SEQ ID NO: 2 corresponds to glycine at position 294 in HER2 consisting of the amino acid sequence set forth in SEQ ID NO: 4. For example, the term "G309A" means that the glycine at position 309 in the HER2 shown in SEQ ID NO: 2 is mutated to alanine. Since such "G309" is at a position corresponding to the amino acid at position 294 in HER2 consisting of the amino acid sequence set forth in SEQ ID NO: 4, "G294A" in the HER2 consisting of the amino acid sequence set forth in SEQ ID NO: 4 corresponds to "G309A" in the HER2 shown in SEQ ID NO: 2. Besides, the position of an amino acid in SEQ ID NO: 2 that corresponds to a certain amino acid in a certain HER2 isoform can be confirmed by Multiple Alignment of BLAST.

SEQUENCE LISTING

```
SEQ ID NO: 1
Accession No.: NM_004448
CDS: 262..4029
   1 gcttgctccc aatcacagga gaaggaggag gtggaggagg agggctgctt gaggaagtat

  61 aagaatgaag ttgtgaagct gagattcccc tccattggga ccggagaaac caggggagcc

 121 ccccgggcag ccgcgcgccc cttcccacgg ggccctttac tgcgccgcgc gcccggcccc

 181 cacccctcgc agcaccccgc gccccgcgcc ctcccagccg ggtccagccg gagccatggg

 241 gccggagccg cagtgagcac catggagctg gcggccttgt gccgctgggg gctcctcctc

 301 gccctcttgc cccccggagc cgcgagcacc caagtgtgca ccggcacaga catgaagctg

 361 cggctccctg ccagtcccga gacccacctg gacatgctcc gccacctcta ccagggctgc

 421 caggtggtgc agggaaacct ggaactcacc tacctgccca ccaatgccag cctgtccttc

 481 ctgcaggata tccaggaggt gcagggctac gtgctcatcg ctcacaacca agtgaggcag

 541 gtcccactgc agaggctgcg gattgtgcga ggcacccagc tctttgagga caactatgcc

 601 ctggccgtgc tagacaatgg agacccgctg aacaatacca cccctgtcac aggggcctcc

 661 ccaggaggcc tgcgggagct gcagcttcga agcctcacag agatcttgaa aggaggggtc

 721 ttgatccagc ggaaccccca gctctgctac caggacacga ttttgtggaa ggacatcttc

 781 cacaagaaca accagctggc tctcacactg atagacacca accgctctcg ggcctgccac

 841 ccctgttctc cgatgtgtaa gggctcccgc tgctggggag agagttctga ggattgtcag

 901 agcctgacgc gcactgtctg tgccggtggc tgtgcccgct gcaaggggcc actgcccact

 961 gactgctgcc atgagcagtg tgctgccggc tgcacgggcc ccaagcactc tgactgcctg

1021 gcctgcctcc acttcaacca cagtggcatc tgtgagctgc actgcccagc cctggtcacc

1081 tacaacacag acacgtttga gtccatgccc aatcccgagg gccggtatac attcggcgcc

1141 agctgtgtga ctgcctgtcc ctacaactac ctttctacgg acgtgggatc ctgcaccctc

1201 gtctgccccc tgcacaacca agaggtgaca gcagaggatg gaacacagcg gtgtgagaag

1261 tgcagcaagc cctgtgcccg agtgtgctat ggtctgggca tggagcactt gcgagaggtg

1321 agggcagtta ccagtgccaa tatccaggag tttgctggct gcaagaagat ctttgggagc

1381 ctggcatttc tgccggagag ctttgatggg gacccagcct ccaacactgc cccgctccag

1441 ccagagcagc tccaagtgtt tgagactctg gaagagatca caggttacct atacatctca

1501 gcatggccgg acagcctgcc tgacctcagc gtcttccaga acctgcaagt aatccgggga

1561 cgaattctgc acaatggcgc ctactcgctg accctgcaag ggctgggcat cagctggctg

1621 gggctgcgct cactgaggga actgggcagt ggactggccc tcatccacca taacacccac

1681 ctctgcttcg tgcacacggt gccctgggac cagctctttc ggaacccgca ccaagctctg

1741 ctccacactg ccaaccggcc agaggacgag tgtgtgggcg agggcctggc ctgccaccag

1801 ctgtgcgccc gagggcactg ctggggtcca gggcccaccc agtgtgtcaa ctgcagccag

1861 ttccttcggg gccaggagtg cgtggaggaa tgccgagtac tgcaggggct ccccagggag
```

-continued 1921 tatgtgaatg ccaggcactg tttgccgtgc caccctgagt gtcagcccca gaatggctca 1981 gtgacctgtt ttggaccgga ggctgaccag tgtgtggcct gtgcccacta taaggaccct 2041 cccttctgcg tggcccgctg ccccagcggt gtgaaacctg acctctccta catgcccatc 2101 tggaagtttc cagatgagga gggcgcatgc cagccttgcc ccatcaactg cacccactcc 2161 tgtgtggacc tggatgacaa gggctgcccc gccgagcaga gagccagccc tctgacgtcc 2221 atcatctctg cggtggttgg cattctgctg gtcgtggtct tgggggtggt ctttgggatc 2281 ctcatcaagc gacggcagca gaagatccgg aagtacacga tgcggagact gctgcaggaa 2341 acggagctgg tggagccgct gacacctagc ggagcgatgc ccaaccaggc gcagatgcgg 2401 atcctgaaag agacggagct gaggaaggtg aaggtgcttg gatctggcgc ttttggcaca 2461 gtctacaagg gcatctggat ccctgatggg gagaatgtga aaattccagt ggccatcaaa 2521 gtgttgaggg aaaacacatc ccccaaagcc aacaaagaaa tcttagacga agcatacgtg 2581 atggctggtg tgggctcccc atatgtctcc cgccttctgg gcatctgcct gacatccacg 2641 gtgcagctgg tgacacagct tatgccctat ggctgcctct tagaccatgt ccgggaaaac 2701 cgcggacgcc tgggctccca ggacctgctg aactggtgta tgcagattgc caaggggatg 2761 agctacctgg aggatgtgcg gctcgtacac agggacttgg ccgctcggaa cgtgctggtc 2821 aagagtccca accatgtcaa aattacagac ttcgggctgg ctcggctgct ggacattgac 2881 gagacagagt accatgcaga tgggggcaag gtgcccatca agtggatggc gctggagtcc 2941 attctccgcc ggcggttcac ccaccagagt gatgtgtgga gttatggtgt gactgtgtgg 3001 gagctgatga cttttggggc caaaccttac gatgggatcc cagcccggga gatccctgac 3061 ctgctggaaa agggggagcg gctgccccag cccccca tct gcaccattga tgtctacatg 3121 atcatggtca aatgttggat gattgactct gaatgtcggc caagattccg ggagttggtg 3181 tctgaattct cccgcatggc cagggacccc cagcgctttg tggtcatcca gaatgaggac 3241 ttgggcccag ccagtccctt ggacagcacc ttctaccgct cactgctgga ggacgatgac 3301 atgggggacc tggtggatgc tgaggagtat ctggtacccc agcagggctt cttctgtcca 3361 gaccctgccc cgggcgctgg gggcatggtc caccacaggc accgcagctc atctaccagg 3421 agtggcggtg gggacctgac actagggctg gagccctctg aagaggaggc ccccaggtct 3481 ccactggcac cctccgaagg ggctggctcc gatgtatttg atggtgacct gggaatgggg 3541 gcagccaagg ggctgcaaag cctccccaca catgacccca gccctctaca gcggtacagt 3601 gaggacccca cagtacccct gccctctgag actgatggct acgttgcccc cctgacctgc 3661 agcccccagc ctgaatatgt gaaccagcca gatgttcggc cccagccccc ttcgccccga 3721 gagggccctc tgcctgctgc ccgacctgct ggtgccactc tggaaaggcc caagactctc 3781 tccccaggga agaatggggt cgtcaaagac gtttttgcct ttgggggtgc cgtggagaac 3841 cccgagtact tgacacccca gggaggagct gcccctcagc cccaccctcc tcctgccttc 3901 agcccagcct tcgacaacct ctattactgg gaccaggacc caccagagcg gggggctcca 3961 cccagcacct tcaaagggac acctacggca gagaacccag agtacctggg tctggacgtg 4021 ccagtgtgaa ccagaaggcc aagtccgcag aagccctgat gtgtcctcag ggagcaggga 4081 aggcctgact tctgctggca tcaagaggtg ggagggccct ccgaccactt ccaggggaac 4141 ctgccatgcc aggaacctgt cctaaggaac cttccttcct gcttgagttc ccagatggct 4201 ggaaggggtc cagcctcgtt ggaagaggaa cagcactggg gagtctttgt ggattctgag 4261 gccctgccca atgagactct agggtccagt ggatgccaca gcccagcttg gccctttcct 4321 tccagatcct gggtactgaa agccttaggg aagctggcct gagaggggaa gcggccctaa -continued 4381 gggagtgtct aagaacaaaa gcgacccatt cagagactgt ccctgaaacc tagtactgcc 4441 ccccatgagg aaggaacagc aatggtgtca gtatccaggc tttgtacaga gtgcttttct 4501 gtttagtttt tacttttttt gttttgtttt tttaaagatg aaataaagac ccagggggag 4561 aatgggtgtt gtatggggag gcaagtgtgg ggggtccttc tccacaccca ctttgtccat 4621 ttgcaaatat attttggaaa acagctaaaa aaaaaaaaaa aaaa SEQ ID NO: 2
Accession No.: NM_004448
MELAALCRWG LLLALLPPGA ASTQVCTGTD MKLRLPASPE THLDMLRHLY QGCQVVQGNL 60

ELTYLPTNAS LSFLQDIQEV QGYVLIAHNQ VRQVPLQRLR IVRGTQLFED NYALAVLDNG 120

DPLNNTTPVT GASPGGLREL QLRSLTEILK GGVLIQRNPQ LCYQDTILWK DIFHKNNQLA 180

LTLIDTNRSR ACHPCSPMCK GSRCWGESSE DCQSLTRTVC AGGCARCKGP LPTDCCHEQC 240

AAGCTGPKHS DCLACLHFNH SGICELHCPA LVTYNTDTFE SMPNPEGRYT FGASCVTACP 300

YNYLSTDVGS CTLVCPLHNQ EVTAEDGTQR CEKCSKPCAR VCYGLGMEHL REVRAVTSAN 360

IQEFAGCKKI FGSLAFLPES FDGDPASNTA PLQPEQLQVF ETLEEITGYL YISAWPDSLP 420

DLSVFQNLQV IRGRILHNGA YSLTLQGLGI SWLGLRSLRE LGSGLALIHH NTHLCFVHTV 480

PWDQLFRNPH QALLHTANRP EDECVGEGLA CHQLCARGHC WGPGPTQCVN CSQFLRGQEC 540

VEECRVLQGL PREYVNARHC LPCHPECQPQ NGSVTCFGPE ADQCVACAHY KDPPFCVARC 600

PSGVKPDLSY MPIWKFPDEE GACQPCPINC THSCVDLDDK GCPAEQRASP LTSIISAVVG 660

ILLVVVLGVV FGILIKRRQQ KIRKYTMRRL LQETELVEPL TPSGAMPNQA QMRILKETEL 720

RKVKVLGSGA FGTVYKGIWI PDGENVKIPV AIKVLRENTS PKANKEILDE AYVMAGVGSP 780

YVSRLLGICL TSTVQLVTQL MPYGCLLDHV RENRGRLGSQ DLLNWCMQIA KGMSYLEDVR 840

LVHRDLAARN VLVKSPNHVK ITDFGLARLL DIDETEYHAD GGKVPIKWMA LESILRRRFT 900

HQSDVWSYGV TVWELMTFGA KPYDGIPARE IPDLLEKGER LPQPPICTID VYMIMVKCWM 960

IDSECRPRFR ELVSEFSRMA RDPQRFVVIQ NEDLGPASPL DSTFYRSLLE DDDMGDLVDA 1020

EEYLVPQQGF FCPDPAPGAG GMVHHRHRSS STRSGGGDLT LGLEPSEEEA PRSPLAPSEG 1080

AGSDVEDGDL GMGAAKGLQS LPTHDPSPLQ RYSEDPTVPL PSETDGYVAP LTCSPQPEYV 1140

NQPDVRPQPP SPREGPLPAA RPAGATLERP KTLSPGKNGV VKDVFAFGGA VENPEYLTPQ 1200

GGAAPQPHPP PAFSPAFDNL YYWDQDPPER GAPPSTFKGT PTAENPEYLG LDVPV 1255

SEQ ID NO: 3
Accession No .: NM_001289936
CDS: 583..4305
1 aagttcctgt gttctttatt ctactctccg ctgaagtcca cacagtttaa attaaagttc 61 ccggattttt gtgggcgcct gccccgcccc tcgtccccct gctgtgtcca tatatcgagg 121 cgatagggtt aagggaaggc ggacgcctga tgggttaatg agcaaactga agtgttttcc 181 atgatctttt ttgagtcgca attgaagtac cacctcccga gggtgattgc ttccccatgc 241 ggggtagaac ctttgctgtc ctgttcacca ctctacctcc agcacagaat ttggcttatg 301 cctactcaat gtgaagatga tgaggatgaa aacctttgtg atgatccact tccacttaat 361 gaatggtggc aaagcaaagc tatattcaag accacatgca aagctactcc ctgagcaaag 421 agtcacagat aaaacggggg caccagtaga atggccagga caaacgcagt gcagcacaga 481 gactcagacc ctggcagcca tgcctgcgca ggcagtgatg agagtgacat gtactgttgt 541 ggacatgcac aaaagtgaga tacttcaaag attccagaag atatgccccg ggggtcctgg 601 aagccacaag tgtgcaccgg cacagacatg aagctgcggc tccctgccag tcccgagacc 661 cacctggaca tgctccgcca cctctaccag ggctgccagg tggtgcaggg aaacctggaa -continued

```
721 ctcacctacc tgcccaccaa tgccagcctg tccttcctgc aggatatcca ggaggtgcag
781 ggctacgtgc tcatcgctca caaccaagtg aggcaggtcc cactgcagag gctgcggatt
841 gtgcgaggca cccagctctt tgaggacaac tatgccctgg ccgtgctaga caatggagac
901 ccgctgaaca ataccacccc tgtcacaggg gcctccccag gaggcctggg ggagctgcag
961 cttcgaagcc tcacagagat cttgaaagga ggggtcttga tccagcggaa cccccagctc
1021 tgctaccagg acacgatttt gtggaaggac atcttccaca agaacaacca gctggctctc
1081 acactgatag acaccaaccg ctctcgggcc tgccacccct gttctccgat gtgtaagggc
1141 tcccgctgct ggggagagag ttctgaggat tgtcagagcc tgacgcgcac tgtctgtgcc
1201 ggtggctgtg cccgctgcaa ggggccactg cccactgact gctgccatga gcagtgtgct
1261 gccggctgca cgggccccaa gcactctgac tgcctggcct gcctccactt caaccacagt
1321 ggcatctgtg agctgcactg cccagccctg gtcacctaca acacagacac gtttgagtcc
1381 atgcccaatc ccgagggccg gtatacattc ggcgccagct gtgtgactgc ctgtccctac
1441 aactaccttt ctacggacgt gggatcctgc accctcgtct gccccctgca caaccaagag
1501 gtgacagcag aggatggaac acagcggtgt gagaagtgca gcaagccctg tgcccgagtg
1561 tgctatggtc tgggcatgga gcacttgcga gaggtgaggg cagttaccag tgccaatatc
1621 caggagtttg ctggctgcaa gaagatcttt gggagcctgg catttctgcc ggagagcttt
1681 gatggggacc cagcctccaa cactgccccg ctccagccag agcagctcca agtgtttgag
1741 actctggaag agatcacagg ttacctatac atctcagcat ggccggacag cctgcctgac
1801 ctcagcgtct tccagaacct gcaagtaatc cggggacgaa ttctgcacaa tggcgcctac
1861 tcgctgaccc tgcaagggct gggcatcagc tggctggggc tgcgctcact gagggaactg
1921 ggcagtggac tggccctcat ccaccataac acccacctct gcttcgtgca cacggtgccc
1981 tgggaccagc tctttcggaa cccgcaccaa gctctgctcc acactgccaa ccggccagag
2041 gacgagtgtg tgggcgaggg cctggcctgc caccagctgt gcgcccgagg gcactgctgg
2101 ggtccagggc ccacccagtg tgtcaactgc agccagttcc ttcggggcca ggagtgcgtg
2161 gaggaatgcc gagtactgca ggggctcccc agggagtatg tgaatgccag gcactgtttg
2221 ccgtgccacc ctgagtgtca gccccagaat ggctcagtga cctgttttgg accggaggct
2281 gaccagtgtg tggcctgtgc ccactataag gaccctccct tctgcgtggc ccgctgcccc
2341 agcggtgtga aacctgacct ctcctacatg cccatctgga agtttccaga tgaggagggc
2401 gcatgccagc cttgccccat caactgcacc cactcctgtg tggacctgga tgacaagggc
2461 tgccccgccg agcagagagc cagccctctg acgtccatca tctctgcggt ggttggcatt
2521 ctgctggtcg tggtcttggg ggtggtcttt gggatcctca tcaagcgacg gcagcagaag
2581 atccggaagt acacgatgcg gagactgctg caggaaacgg agctggtgga gccgctgaca
2641 cctagcggag cgatgcccaa ccaggcgcag atgcggatcc tgaaagagac ggagctgagg
2701 aaggtgaagg tgcttggatc tggcgctttt ggcacagtct acaagggcat ctggatccct
2761 gatggggaga atgtgaaaat tccagtggcc atcaaagtgt tgagggaaaa cacatccccc
2821 aaagccaaca aagaaatctt agacgaagca tacgtgatgg ctggtgtggg ctccccatat
2881 gtctcccgcc ttctgggcat ctgcctgaca tccacggtgc agctggtgac acagcttatg
2941 ccctatggct gcctcttaga ccatgtccgg gaaaaccgcg gacgcctggg ctcccaggac
3001 ctgctgaact ggtgtatgca gattgccaag gggatgagct acctggagga tgtgcggctc
3061 gtacacaggg acttggccgc tcggaacgtg ctggtcaaga gtcccaacca tgtcaaaatt
```

-continued 3121 acagacttcg ggctggctcg gctgctggac attgacgaga cagagtacca tgcagatggg 3181 ggcaaggtgc ccatcaagtg gatggcgctg gagtccattc tccgccggcg gttcacccac 3241 cagagtgatg tgtggagtta tggtgtgact gtgtgggagc tgatgacttt tggggccaaa 3301 ccttacgatg ggatcccagc ccgggagatc cctgacctgc tggaaaaggg ggagcggctg 3361 ccccagcccc ccatctgcac cattgatgtc tacatgatca tggtcaaatg ttggatgatt 3421 gactctgaat gtcggccaag attccgggag ttggtgtctg aattctcccg catggccagg 3481 gacccccagc gctttgtggt catccagaat gaggacttgg gcccagccag tcccttggac 3541 agcaccttct accgctcact gctggaggac gatgacatgg gggacctggt ggatgctgag 3601 gagtatctgg taccccagca gggcttcttc tgtccagacc ctgccccggg cgctgggggc 3661 atggtccacc acaggcaccg cagctcatct accaggagtg gcggtgggga cctgacacta 3721 gggctggagc cctctgaaga ggaggccccc aggtctccac tggcaccctc cgaaggggct 3781 ggctccgatg tatttgatgg tgacctggga atgggggcag ccaaggggct gcaaagcctc 3841 cccacacatg accccagccc tctacagcgg tacagtgagg accccacagt acccctgccc 3901 tctgagactg atggctacgt tgcccccctg acctgcagcc cccagcctga atatgtgaac 3961 cagccagatg ttcggcccca gcccccttcg ccccgagagg gccctctgcc tgctgcccga 4021 cctgctggtg ccactctgga aaggcccaag actctctccc cagggaagaa tggggtcgtc 4081 aaagacgttt ttgcctttgg gggtgccgtg gagaaccccg agtacttgac accccaggga 4141 ggagctgccc ctcagcccca ccctcctcct gccttcagcc cagccttcga caacctctat 4201 tactgggacc aggacccacc agaggggggg gctccaccca gcaccttcaa agggacacct 4261 acggcagaga acccagagta cctgggtctg gacgtgccag tgtgaaccag aaggccaagt 4321 ccgcagaagc cctgatgtgt cctcagggag cagggaaggc ctgacttctg ctggcatcaa 4381 gaggtgggag ggccctccga ccacttccag gggaacctgc catgccagga acctgtccta 4441 aggaaccttc cttcctgctt gagttcccag atggctggaa ggggtccagc ctcgttggaa 4501 gaggaacagc actggggagt ctttgtggat tctgaggccc tgcccaatga gactctaggg 4561 tccagtggat gccacagccc agcttggccc tttccttcca gatcctgggt actgaaagcc 4621 ttagggaagc tggcctgaga ggggaagcgg ccctaaggga gtgtctaaga acaaaagcga 4681 cccattcaga gactgtccct gaaacctagt actgcccccc atgaggaagg aacagcaatg 4741 gtgtcagtat ccaggctttg tacagagtgc ttttctgttt agtttttact tttttttgttt 4801 tgtttttttta aagatgaaat aaagacccag gggagaatg ggtgttgtat ggggaggcaa 4861 gtgtgggggg tccttctcca cacccacttt gtccatttgc aaatatattt tggaaaacag 4921 ctaaaaaaaa aaaaaaaaaa SEQ ID NO: 4
Accession No.: NM_001289936
MPRGSWKPQV CTGTDMKLRL PASPETHLDM LRHLYQGCQV VQGNLELTYL PTNASLSFLQ 60

DIQEVQGYVL IAHNQVRQVP LQRLRIVRGT QLFEDNYALA VLDNGDPLNN TTPVTGASPG 120

GLRELQLRSL TEILKGGVLI QRNPQLCYQD TILWKDIFHK NNQLALTLID TNRSRACHPC 180

SPMCKGSRCW GESSEDCQSL TRTVCAGGCA RCKGPLPTDC CHEQCAAGCT GPKHSDCLAC 240

LHFNHSGICE LHCPALVTYN TDTFESMPNP EGRYTFGASC VTACPYNYLS TDVGSCTLVC 300

PLHNQEVTAE DGTQRCEKCS KPCARVCYGL GMEHLREVRA VTSANIQEFA GCKKIFGSLA 360

FLPESFDGDP ASNTAPLQPE QLQVFETLEE ITGYLYISAW PDSLPDLSVF QNLQVIRGRI 420

LHNGAYSLTL QGLGISWLGL RSLRELGSGL ALIHHNTHLC FVHTVPWDQL FRNPHQALLH 480

TANRPEDECV GEGLACHQLC ARGHCWGPGP TQCVNCSQFL RGQECVEECR VLQGLPREYV 540

-continued

```
NARHCLPCHP ECQPQNGSVT CFGPEADQCV ACAHYKDPPF CVARCPSGVK PDLSYMPIWK  600

FPDEEGACQP CPINCTHSCV DLDDKGCPAE QRASPLTSII SAVVGILLVV VLGVVFGILI  660

KRRQQKIRKY TMRRLLQETE LVEPLTPSGA MPNQAQMRIL KETELRKVKV LGSGAFGTVY  720

KGIWIPDGEN VKIPVAIKVL RENTSPKANK EILDEAYVMA GVGSPYVSRL LGICLTSTVQ  780

LVTQLMPYGC LLDHVRENRG RLGSQDLLNW CMQIAKGMSY LEDVRLVHRD LAARNVLVKS  840

PNHVKITDFG LARLLDIDET EYHADGGKVP IKWMALESIL RRRFTHQSDV WSYGVTVWEL  900

MTFGAKPYDG IPAREIPDLL EKGERLPQPP ICTIDVYMIM VKCWMIDSEC RPRFRELVSE  960

FSRMARDPQR FVVIQNEDLG PASPLDSTFY RSLLEDDDMG DLVDAEEYLV PQQGFFCPDP 1020

APGAGGMVHH RHRSSSTRSG GGDLTLGLEP SEEEAPRSPL APSEGAGSDV FDGDLGMGAA 1080

KGLQSLPTHD PSPLQRYSED PTVPLPSETD GYVAPLTCSP QPEYVNQPDV RPQPPSPREG 1140

PLPAARPAGA TLERPKTLSP GKNGVVKDVF AFGGAVENPE YLTPQGGAAP QPHPPPAFSP 1200

AFDNLYYWDQ DPPERGAPPS TFKGTPTAEN PEYLGLDVPV                       1240

SEQ ID NO:5
Accession No.: NM_001005862
CDS: 577..4254
   1 aagttcctgt gttctttatt ctactctccg ctgaagtcca cacagtttaa attaaagttc

  61 ccggattttt gtgggcgcct gccccgcccc tcgtccccct gctgtgtcca tatatcgagg

 121 cgatagggtt aagggaaggc ggacgcctga tgggttaatg agcaaactga agtgttttcc

 181 atgatctttt ttgagtcgca attgaagtac cacctcccga gggtgattgc ttccccatgc

 241 ggggtagaac ctttgctgtc ctgttcacca ctctacctcc agcacagaat ttggcttatg

 301 cctactcaat gtgaagatga tgaggatgaa aacctttgtg atgatccact tccacttaat

 361 gaatggtggc aaagcaaagc tatattcaag accacatgca aagctactcc ctgagcaaag

 421 agtcacagat aaaacggggg caccagtaga atggccagga caaacgcagt gcagcacaga

 481 gactcagacc ctggcagcca tgcctgcgca ggcagtgatg agagtgacat gtactgttgt

 541 ggacatgcac aaaagtgagt gtgcaccggc acagacatga agctgcggct ccctgccagt

 601 cccgagaccc acctggacat gctccgccac ctctaccagg gctgccaggt ggtgcaggga

 661 aacctggaac tcacctacct gcccaccaat gccagcctgt ccttcctgca ggatatccag

 721 gaggtgcagg gctacgtgct catcgctcac aaccaagtga ggcaggtccc actgcagagg

 781 ctgcggattg tgcgaggcac ccagctcttt gaggacaact atgccctggc cgtgctagac

 841 aatggagacc cgctgaacaa taccacccct gtcacagggg cctccccagg aggcctgcgg

 901 gagctgcagc ttcgaagcct cacagagatc ttgaaaggag gggtcttgat ccagcggaac

 961 ccccagctct gctaccagga cacgattttg tggaaggaca tcttccacaa gaacaaccag

1021 ctggctctca cactgataga caccaaccgc tctcgggcct gccacccctg ttctccgatg

1081 tgtaagggct cccgctgctg gggagagagt tctgaggatt gtcagagcct gacgcgcact

1141 gtctgtgccg gtggctgtgc ccgctgcaag gggccactgc ccactgactg ctgccatgag

1201 cagtgtgctg ccggctgcac gggccccaag cactctgact gcctggcctg cctccacttc

1261 aaccacagtg gcatctgtga gctgcactgc ccagccctgg tcacctacaa cacagacacg

1321 tttgagtcca tgcccaatcc cgagggccgg tatacattcg gcgccagctg tgtgactgcc

1381 tgtccctaca actacctttc tacggacgtg ggatcctgca ccctcgtctg ccccctgcac

1441 aaccaagagg tgacagcaga ggatggaaca cagcggtgtg agaagtgcag caagccctgt

1501 gcccgagtgt gctatggtct gggcatggag cacttgcgag aggtgagggc agttaccagt

1561 gccaatatcc aggagtttgc tggctgcaag aagatctttg ggagcctggc atttctgccg
```

-continued 1621 gagagctttg atggggaccc agcctccaac actgccccgc tccagccaga gcagctccaa
1681 gtgtttgaga ctctggaaga gatcacaggt tacctataca tctcagcatg gccggacagc
1741 ctgcctgacc tcagcgtctt ccagaacctg caagtaatcc ggggacgaat tctgcacaat
1801 ggcgcctact cgctgaccct gcaagggctg ggcatcagct ggctggggct gcgctcactg
1861 agggaactgg gcagtggact ggccctcatc caccataaca cccacctctg cttcgtgcac
1921 acggtgccct gggaccagct ctttcggaac ccgcaccaag ctctgctcca cactgccaac
1981 cggccagagg acgagtgtgt gggcgagggc ctggcctgcc accagctgtg cgcccgaggg
2041 cactgctggg gtccagggcc cacccagtgt gtcaactgca gccagttcct tcggggccag
2101 gagtgcgtgg aggaatgccg agtactgcag gggctcccca gggagtatgt gaatgccagg
2161 cactgtttgc cgtgccaccc tgagtgtcag ccccagaatg gctcagtgac ctgttttgga
2221 ccggaggctg accagtgtgt ggcctgtgcc cactataagg accctccctt ctgcgtggcc
2281 cgctgcccca gcggtgtgaa acctgacctc tcctacatgc ccatctggaa gtttccagat
2341 gaggagggcg catgccagcc ttgccccatc aactgcaccc actcctgtgt ggacctggat
2401 gacaagggct gccccgccga gcagagagcc agccctctga cgtccatcat ctctgcggtg
2461 gttggcattc tgctggtcgt ggtcttgggg gtggtctttg ggatcctcat caagcgacgg
2521 cagcagaaga tccggaagta cacgatgcgg agactgctgc aggaaacgga gctggtggag
2581 ccgctgacac ctagcggagc gatgcccaac caggcgcaga tgcggatcct gaaagagacg
2641 gagctgagga aggtgaaggt gcttggatct ggcgcttttg gcacagtcta caagggcatc
2701 tggatccctg atggggagaa tgtgaaaatt ccagtggcca tcaaagtgtt gagggaaaac
2761 acatccccca aagccaacaa agaaatctta gacgaagcat acgtgatggc tggtgtgggc
2821 tccccatatg tctcccgcct tctgggcatc tgcctgacat ccacggtgca gctggtgaca
2881 cagcttatgc cctatggctg cctcttagac catgtccggg aaaaccgcgg acgcctgggc
2941 tcccaggacc tgctgaactg gtgtatgcag attgccaagg ggatgagcta cctggaggat
3001 gtgcggctcg tacacaggga cttggccgct cggaacgtgc tggtcaagag tcccaaccat
3061 gtcaaaatta cagacttcgg gctggctcgg ctgctggaca ttgacgagac agagtaccat
3121 gcagatgggg gcaaggtgcc catcaagtgg atggcgctgg agtccattct ccgccggcgg
3181 ttcacccacc agagtgatgt gtggagttat ggtgtgactg tgtgggagct gatgactttt
3241 ggggccaaac cttacgatgg gatcccagcc cgggagatcc ctgacctgct ggaaaagggg
3301 gagcggctgc cccagccccc catctgcacc attgatgtct acatgatcat ggtcaaatgt
3361 tggatgattg actctgaatg tcggccaaga ttccgggagt tggtgtctga attctcccgc
3421 atggccaggg acccccagcg ctttgtggtc atccagaatg aggacttggg cccagccagt
3481 cccttggaca gcaccttcta ccgctcactg ctggaggacg atgacatggg ggacctggtg
3541 gatgctgagg agtatctggt accccagcag ggcttcttct gtccagaccc tgccccgggc
3601 gctgggggca tggtccacca caggcaccgc agctcatcta ccaggagtgg cgggggggac
3661 ctgacactag ggctggagcc ctctgaagag gaggccccca ggtctccact ggcaccctcc
3721 gaaggggctg gctccgatgt atttgatggt gacctgggaa tgggggcagc caaggggctg
3781 caaagcctcc ccacacatga ccccagccct ctacagcggt acagtgagga ccccacagta
3841 cccctgccct ctgagactga tggctacgtt gcccccctga cctgcagccc ccagcctgaa
3901 tatgtgaacc agccagatgt tcggccccag ccccccttcgc cccgagaggg ccctctgcct
3961 gctgcccgac ctgctggtgc cactctggaa aggcccaaga ctctctcccc agggaagaat -continued

```
4021 ggggtcgtca aagacgtttt tgcctttggg ggtgccgtgg agaaccccga gtacttgaca

4081 ccccagggag gagctgcccc tcagccccac cctcctcctg ccttcagccc agccttcgac

4141 aacctctatt actgggacca ggacccacca gagcgggggg ctccacccag caccttcaaa

4201 gggacaccta cggcagagaa cccagagtac ctgggtctgg acgtgccagt gtgaaccaga

4261 aggccaagtc cgcagaagcc ctgatgtgtc ctcagggagc agggaaggcc tgacttctgc

4321 tggcatcaag aggtgggagg gccctccgac cacttccagg ggaacctgcc atgccaggaa

4381 cctgtcctaa ggaaccttcc ttcctgcttg agttcccaga tggctggaag gggtccagcc

4441 tcgttggaag aggaacagca ctggggagtc tttgtggatt ctgaggccct gcccaatgag

4501 actctagggt ccagtggatg ccacagccca gcttggccct ttccttccag atcctgggta

4561 ctgaaagcct tagggaagct ggcctgagag gggaagcggc cctaagggag tgtctaagaa

4621 caaaagcgac ccattcagag actgtccctg aaacctagta ctgcccccca tgaggaagga

4681 acagcaatgg tgtcagtatc caggctttgt acagagtgct tttctgttta gtttttactt

4741 tttttgtttt gtttttttaa agatgaaata aagacccagg gggagaatgg gtgttgtatg

4801 gggaggcaag tgtggggggt ccttctccac acccactttg tccatttgca aatatatttt

4861 ggaaaacagc taaaaaaaaa aaaaaaaaa
```

SEQ ID NO: 6
Accession No.: NM_001005862

```
MKLRLPASPE THLDMLRHLY QGCQVVQGNL ELTYLPTNAS LSFLQDIQEV QGYVLIAHNQ   60

VRQVPLQRLR IVRGTQLFED NYALAVLDNG DPLNNTTPVT GASPGGLREL QLRSLTEILK  120

GGVLIQRNPQ LCYQDTILWK DIFHKNNQLA LTLIDTNRSR ACHPCSPMCK GSRCWGESSE  180

DCQSLTRTVC AGGCARCKGP LPTDCCHEQC AAGCTGPKHS DCLACLHENH SGICELHCPA  240

LVTYNTDTFE SMPNPEGRYT FGASCVTACP YNYLSTDVGS CTLVCPLHNQ EVTAEDGTQR  300

CEKCSKPCAR VCYGLGMEHL REVRAVTSAN IQEFAGCKKI FGSLAFLPES FDGDPASNTA  360

PLQPEQLQVF ETLEEITGYL YISAWPDSLP DLSVFQNLQV IRGRILHNGA YSLTLQGLGI  420

SWLGLRSLRE LGSGLALIHH NTHLCFVHTV PWDQLFRNPH QALLHTANRP EDECVGEGLA  480

CHQLCARGHC WGPGPTQCVN CSQFLRGQEC VEECRVLQGL PREYVNARHC LPCHPECQPQ  540

NGSVTCFGPE ADQCVACAHY KDPPFCVARC PSGVKPDLSY MPIWKFPDEE GACQPCPINC  600

THSCVDLDDK GCPAEQRASP LTSIISAVVG ILLVVVLGVV FGILIKRRQQ KIRKYTMRRL  660

LQETELVEPL TPSGAMPNQA QMRILKETEL RKVKVLGSGA FGTVYKGIWI PDGENVKIPV  720

AIKVLRENTS PKANKEILDE AYVMAGVGSP YVSRLLGICL TSTVQLVTQL MPYGCLLDHV  780

RENRGRLGSQ DLLNWCMQIA KGMSYLEDVR LVHRDLAARN VLVKSPNHVK ITDFGLARLL  840

DIDETEYHAD GGKVPIKWMA LESILRRRFT HQSDVWSYGV TVWELMTFGA KPYDGIPARE  900

IPDLLEKGER LPQPPICTID VYMIMVKCWM IDSECRPRER ELVSEFSRMA RDPQRFVVIQ  960

NEDLGPASPL DSTFYRSLLE DDDMGDLVDA EEYLVPQQGF FCPDPAPGAG GMVHHRHRSS 1020

STRSGGGDLT LGLEPSEEEA PRSPLAPSEG AGSDVEDGDL GMGAAKGLQS LPTHDPSPLQ 1080

RYSEDPTVPL PSETDGYVAP LTCSPQPEYV NQPDVRPQPP SPREGPLPAA RPAGATLERP 1140

KTLSPGKNGV VKDVFAFGGA VENPEYLTPQ GGAAPQPHPP PAFSPAFDNL YYWDQDPPER 1200

GAPPSTFKGT PTAENPEYLG LDVPV                                     1225
```

One embodiment of the present invention provides an antitumor agent, comprising the above-described crystal of compound (I) (i.e., a free-form crystal of compound (I) or a crystal of compound (I) with an acid (salt crystal or co-crystal)). In addition, one embodiment of the present invention provides a method for treating tumor, comprising administering an effective amount of the above-described crystal of compound (I) (i.e., a free-form crystal of compound (I) or a crystal of compound (I) with an acid (salt crystal or co-crystal)) to a subject in need thereof. Moreover, one embodiment of the present invention provides use of the above-described crystal of compound (I) (i.e., a free-form crystal of compound (I) or a crystal of compound (I) with an acid (salt crystal or co-crystal)) for the production of an antitumor agent. Furthermore, one embodiment of the present invention provides the above-described crystal of compound (I) (i.e., a free-form crystal of compound (I) or a crystal of compound (I) with an acid (salt crystal or co-crystal)) for use in the treatment of tumor.

The crystals of the present invention may be used in postoperative adjuvant chemotherapy performed to prevent recurrence after surgical removal of a tumor, or may be used in neoadjuvant chemotherapy performed in advance before surgical removal of a tumor.

The tumor that is the target of the present invention is not particularly limited. Examples of the tumor may include brain tumor, head and neck cancer, digestive cancer (esophageal cancer, stomach cancer, duodenal cancer, liver cancer, biliary tract cancer (gallbladder and/or bile duct cancer, etc.), pancreatic cancer, colorectal cancer (colon cancer, rectal cancer, etc.), etc.), lung cancer (non-small cell lung cancer, small cell lung cancer, mesothelioma, etc.), breast cancer, genital cancer (ovarian cancer, uterine cancer (cervical cancer, endometrial cancer, etc.), etc.), urinary organ cancer (kidney cancer, bladder cancer, prostate cancer, testicular tumor, etc.), hematopoietic tumor (leukemia, malignant lymphoma, multiple myeloma, etc.), bone and/or soft tissue tumor, and skin cancer. Among these, preferable is lung cancer, breast cancer, stomach cancer, colorectal cancer, bladder cancer, biliary tract cancer or uterine cancer, and more preferable is lung cancer, breast cancer, stomach cancer, bladder cancer, or biliary tract cancer.

In one embodiment, the tumor is a brain tumor. The compound of the present invention may be useful for the treatment of the symptoms of brain that is required to pass through the blood-brain barrier. The compound of one embodiment has favorable permeability through the blood-brain barrier for the delivery thereof into the brain, namely, excellent brain penetration properties. As an indicator of the penetration properties of the compound into the brain, the concentration of the compound in the brain or a Kp value (brain-to-plasma drug concentration ratio) is applied.

The brain tumor treated with the compound of the present invention includes metastatic brain tumor and primary brain tumor.

Examples of the brain tumor may include, but are not particularly limited to, metastatic brain tumor (e.g., brain metastasis of lung cancer, breast cancer, stomach cancer, colorectal cancer, bladder cancer, biliary tract cancer, uterine cancer, etc. (preferably, lung cancer, breast cancer, or stomach cancer)), piliocytic astrocytoma, diffuse astrocytoma, oligodendroma and/or oligodendroastrocytoma, anaplastic astrocytoma and/or anaplastic oligodendroglioma, anaplastic oligodendroastrocytoma, glioblastoma, ependymoma, anaplastic ependymoma, ganglioglioma, central neurocytoma, medulloblastoma, germinoma, central nervous system malignant lymphoma, meningioma, neurilemmoma, GH secreting pituitary adenoma, PRL-secreting pituitary adenoma, ACTH-secreting pituitary adenoma, nonfunctional pituitary adenoma, craniopharyngioma, chordoma, hemangioblastoma, and epidermoid tumor.

In the present description, the term "effective amount" of the compound means the amount of the compound of the present invention that induces the biological or medical response of a subject, such as, for example, reduction or inhibition of enzyme or protein activity; or ameliorates symptoms, alleviates conditions, and retards or delays the progression of disease; and the like (therapeutically effective amount). In the present description, the term "subject" includes mammals and non-mammals. Examples of the mammal may include, but are not limited to, a human, a chimpanzee, an ape, a monkey, a bovine, a horse, sheep, a goat, a swine, a rabbit, a dog, a cat, a rat, a mouse, a guinea pig, a hedgehog, a kangaroo, a mole, a wild pig, a bear, a tiger, and a lion. Examples of the non-mammal may include, but are not limited to, birds, fish, and reptiles. In one embodiment, the subject is a human, and may be a human who has been diagnosed to need the treatment for the symptoms, conditions or disease disclosed in the present description.

Upon the use of the compound (I) or a salt crystal or co-crystal thereof as a medicament, various types of dosage forms can be adopted depending on the therapeutic purpose with or without crushing the crystal. Examples of the dosage form may include all of oral agents such as tablets, capsules, granules, fine granules, powders, and dry syrups, suppositories, inhalants, nasal drops, ointments, patches, and injections. Pharmaceutical compositions suitable for these dosage forms can be prepared by commonly used production methods that are known to skilled persons using pharmaceutically acceptable carriers.

One embodiment of the present invention provides an antitumor agent comprising the above-described crystal of compound (I) (i.e., a free-form crystal of compound (I) or a crystal of compound (I) with an acid (salt crystal or co-crystal)). One embodiment of the present invention also provides a method for treating tumor, comprising administering an effective amount of the crystal of compound (I) (i.e., a free-form crystal of compound (I) or a crystal of compound (I) with an acid (salt crystal or co-crystal)) to a subject in need thereof. One embodiment of the present invention also provides the use of the crystal of compound (I) (i.e., a free-form crystal of compound (I) or a crystal of compound (I) with an acid (salt crystal or co-crystal)) for the production of an antitumor agent. One embodiment of the present invention also provides the crystal of compound (I) (i.e., a free-form crystal of compound (I) or a crystal of compound (I) with an acid (salt crystal or co-crystal)) for use in the treatment of tumor by administration thereof.

One embodiment of the present invention provides an antitumor agent for oral administration comprising the above-described crystal of compound (I) (i.e., a free-form crystal of compound (I) or a crystal of compound (I) with an acid (salt crystal or co-crystal)). One embodiment of the present invention also provides a method for treating tumor, comprising orally administering an effective amount of the crystal of compound (I) (i.e., a free-form crystal of compound (I) or a crystal of compound (I) with an acid (salt crystal or co-crystal)) to a subject in need thereof. One embodiment of the present invention also provides the use of the crystal of compound (I) (i.e., a free-form crystal of compound (I) or a crystal of compound (I) with an acid (salt crystal or co-crystal)) for the production of an antitumor agent for oral administration. One embodiment of the present invention also provides the crystal of compound (I) (i.e., a free-form crystal of compound (I) or a crystal of compound (I) with an acid (salt crystal or co-crystal)) for use in the treatment of tumor by oral administration thereof.

One embodiment of the present invention provides a pharmaceutical composition comprising the crystal of compound (I) (i.e., a free-form crystal of compound (I) or a crystal of compound (I) with an acid (salt crystal or co-crystal)). The pharmaceutical composition in one embodiment of the present invention comprises the crystal of compound (I) (i.e., a free-form crystal of compound (I) or a crystal of compound (I) with an acid (salt crystal or co-crystal)) and a pharmaceutically acceptable carrier. One embodiment of the present invention also provides the use of the crystal of compound (I) (i.e., a free-form crystal of compound (I) or a crystal of compound (I) with an acid (salt crystal or co-crystal)) for the production of a pharmaceutical composition. One embodiment of the present invention provides the crystal of compound (I) (i.e., a free-form crystal of compound (I) or a crystal of compound (I) with an acid (salt crystal or co-crystal)) for use as a medicament. One embodiment of the present invention provides a kit comprising (i) a pharmaceutical composition comprising the crystal of compound (I) (i.e., a free-form crystal of compound (I) or a crystal of compound (I) with an acid (salt crystal or co-crystal)) and (ii) an instruction for use of the pharmaceutical composition.

As pharmaceutically acceptable carriers, various types of organic or inorganic carrier substances, which are commonly used as preparation materials, are used. When the compound of the present invention is processed into a solid preparation, examples of the pharmaceutically acceptable carrier mixed into the compound of the present invention may include an excipient, a binder, a disintegrator, a lubricant, and a coating agent. When the compound of the present invention is processed into a liquid preparation, examples of the pharmaceutically acceptable carrier mixed into the compound of the present invention may include a solvent, a solubilizer, a suspending agent, a tonicity agent, a buffer, and a soothing agent. In addition, preparation additives such as an antiseptic, an antioxidant, a coloring agent, a sweetener, and a stabilizer can also be used, as necessary.

Examples of the excipient may include lactose, sucrose, D-mannitol, starch, crystalline cellulose, and calcium silicate.

Examples of the binder may include hydroxypropyl cellulose, methyl cellulose, polyvinylpyrrolidone, candy powder, and hypromellose.

Examples of the disintegrator may include sodium starch glycolate, carmellose calcium, croscarmellose sodium, crospovidone, low-substituted hydroxypropyl cellulose, and partially pregelatinized starch.

Examples of the lubricant may include talc, magnesium stearate, sucrose fatty acid ester, stearic acid, and sodium stearyl fumarate.

Examples of the coating agent may include ethyl cellulose, aminoalkyl methacrylate copolymer RS, hypromellose, and sucrose.

Examples of the solvent may include water, propylene glycol, and physiological saline.

Examples of the solubilizer may include polyethylene glycol, ethanol, a-cyclodextrin, macrogol 400, and polysorbate 80.

Examples of the suspending agent may include carrageenan, crystalline cellulose/carmellose sodium, and polyoxyethylene hydrogenated castor oil.

Examples of the tonicity agent may include sodium chloride, glycerin, and potassium chloride.

Examples of the pH adjuster/buffer may include sodium citrate, hydrochloric acid, lactic acid, phosphoric acid, and sodium dihydrogen phosphate.

Examples of the soothing agent may include procaine hydrochloride and lidocaine.

Examples of the antiseptic may include ethyl paraoxybenzoate, cresol, and benzalkonium chloride.

Examples of the antioxidant may include sodium sulfite, ascorbic acid, and natural vitamin E.

Examples of the coloring agent may include titanium oxide, iron sesquioxide, edible blue No. 1, and copper chlorophyll.

Examples of the corrigent may include aspartame, saccharin, sucralose, 1-menthol, and mint flavor.

Examples of the stabilizer may include sodium pyrosulfite, sodium edetate, erythorbic acid, magnesium oxide, and dibutylhydroxytoluene.

In the case of preparing a solid preparation for oral administration, an excipient, and as necessary, a binder, a disintegrator, a lubricant, a coloring agent, a corrigent, and the like are added to a crystal of compound (I) (i.e., a free-form crystal of compound (I) or a crystal of compound (I) with an acid (salt crystal or co-crystal)), and thereafter, a tablet, a coated tablet, a granule, a powder agent, a capsule, and the like can be produced according to ordinary methods.

In the case of preparing an injection, a pH adjuster, a buffer, a stabilizer, a tonicity agent, a local anesthetic, and the like are added to a crystal of compound (I) (i.e., a free-form crystal of compound (I) or a crystal of compound (I) with an acid (salt crystal or co-crystal)), and thereafter, subcutaneous, intramuscular, and intravenous injections can be produced according to ordinary methods.

The amount of a crystal of compound (I) (i.e., a free-form crystal of compound (I) or a crystal of compound (I) with an acid (salt crystal or co-crystal)) to be mixed into the above-described each dosage unit form depends on the symptoms of a patient to whom the crystal should be applied, the dosage form, or the like, and thus, the amount of the compound of the present invention is not constant. In general, it is preferable that the applied dose is set to be approximately 0.05 to 1000 mg per dosage unit form in the case of an oral agent, it is set to be approximately 0.1 to 500 mg per dosage unit form in the case of an injection, and it is set to be approximately 1 to 1000 mg per dosage unit form in the case of a suppository or a topical agent in terms of the free-form compound (I).

The daily dose of a crystal of compound (I) (i.e., a free-form crystal of compound (I) or a crystal of compound (I) with an acid (salt crystal or co-crystal)) in a drug having the above-described dosage form is different depending on the symptoms, body weight, age, sex and the like of a patient, and thus, it cannot be generally determined. However, the crystal may be administered to an adult (body weight: 50 kg) at a daily dose of generally approximately 0.05 to 5000 mg, and preferably 0.1 to 1000 mg in terms of the free-form compound (I), and it is preferably administered once a day or in 2 to 3 divided doses.

EXAMPLES

Hereinafter, the present invention will be further described specifically with reference to the Examples below. However, these Examples are not intended to limit the scope of the present invention. Although the present invention has been fully described by way of the Examples, it will be appreciated that various changes and/or modifications may be made by skilled persons. Therefore, such changes and/or modifications are included in the invention unless they are outside the scope of the present invention.

In the following Examples regarding compounds, "%" indicates weight percent, unless otherwise specified.

Various types of reagents used in the Examples were commercially available products, unless otherwise specified. Silica gel chromatography was carried out using Purif-Pack (registered trademark) SI manufactured by MORITEX Corporation, KP-Sil (registered trademark) Silica Prepacked Column manufactured by Biotage Japan Ltd., or HP-Sil (registered trademark) Silica Prepacked Column manufactured by Biotage Japan Ltd. Basic silica gel column chromatography was carried out using Purif-Pack (registered trademark) NH manufactured by MORITEX Corporation or KP-NH (registered trademark) Prepacked Column manufactured by Biotage Japan Ltd. Preparative thin-layer chromatography was carried out using Kieselgel TM60F254, Art. 5744, manufactured by Merck, or NH2 Silica Gel 60F254 Plate, manufactured by Wako Pure Chemical Industries, Ltd. For NMR spectral measurement, AL400 (400 MHZ; JEOL Ltd. (JEOL)), a Mercury400 (400 MHz; Agilent Technologies) type spectrometer or an Inova400 (400 MHz; Agilent Technologies) type spectrometer equipped with a 400 MNMR probe (Protasis) was used. When tetramethylsilane was contained in a heavy solvent, tetramethylsilane was used as an internal reference, and in other cases, an NMR solvent was used as an internal reference for measurement, and the total 8 value was shown in ppm.

In addition, LCMS spectral measurement was carried out using ACQUITY SQD (quadrupole type) manufactured by Waters under the following conditions.

Column: XSelect CSH C18 (4.6×150 mm, 3.5 μm) manufactured by Waters MS detection: ESI positive
UV detection: 246 nm
Column temperature: 40° C.
Column flow rate: 1.0 mL/min
Mobile phase: water/acetonitrile (0.1% formic acid)
Injection amount: 5 μL
Sample cooler: 5° C.
Sample concentration: 1 mg/mL
Gradient (Table 1)

TABLE 1

| Time (min) | Water | Acetonitrile |
|---|---|---|
| 0-0.1 | 95% | 5% |
| 0.1-2.1 | 95%→5% | 5%→95% |
| 2.1-3.1 | 5% | 95% |

Reverse phase preparative HPLC purification was carried out under the following conditions using a preparative system manufactured by WATERS.

Column: A column prepared by connecting YMC-Actus Triart C18 (20×50 mm, 5 μm) manufactured by YMC and YMC-Actus Triart C18 (20×10 mm, 5 μm) manufactured by YMC was used.
UV detection: 254 nm
MS detection: ESI positive
Column flow rate: 25 mL/min
Mobile phase: water/acetonitrile (0.1% formic acid)
Injection amount: 0.1-0.5 mL
Abbreviations have the following meanings.
s: Singlet
d: Doublet
t: Triplet
dt: Double triplet
m: Multiplet
DMSO-d6: Deuterated dimethyl sulfoxide
$CDCl_3$: Deuterated chloroform
THF: Tetrahydrofuran
DMA: N,N-dimethylacetamide
NMP: 1-Methyl-2-pyrrolidinone
DMSO: Dimethyl sulfoxide Powder X-Ray Diffraction Analysis Powder X-ray diffraction analysis was carried out according to any of the following test conditions after lightly pulverizing an appropriate amount of a test substance in an agate mortar as needed.

Apparatus: EMPYREAN (Method A) manufactured by PANalytical
Reflection Method (Concentration Method)
Target: Cu
X-ray tube current: 40 mA
X-ray tube voltage: 45 kV
Scanning range: 2θ=5.0° to 40.0°
Step: 2θ=0.0131°
Average time/step 8.670 s
Scan speed: 0.0015°/s
Divergence slit: 1°
Scattering slit: 2.0 mm
Light receiving slit: 8.0 mm
Apparatus: EMPYREAN (Method B) manufactured by PANalytical
Permeation Method
Target: Cu
X-ray tube current: 40 mA
X-ray tube voltage: 45 kV
Scanning range: 2θ=2.0° to 40.0°
Step: 2θ=0.0066°
Average time/step 8.670 s
Scan speed: 0.0008°/s
Divergence slit: 1/2°
Scattering slit: 2.0 mm
Light receiving slit: None Handling of the apparatuses, including data processing, was in accordance with the methods and procedures instructed for each apparatus. Numerical values obtained from various spectra may vary slightly depending on the direction of crystal growth, particle size, analysis conditions, and the like. Therefore, those numerical values should not be understood exactly as they are.

For simultaneous thermogravimetry-differential thermal analysis (TG-DTA), analysis was carried out using 2 to 3 mg of a test substance according to the following test conditions.

Apparatus: TG/DTA7200
Manuractured by Hitachi High-Tech Science Corporation
Sample container: Made of aluminum
Temperature increase rate: Temperature was increased from 25° C. to 290° C. at 10° C./min.
Atmospheric gas: Air (200 mL/min)
Control substance: Empty container Handling of the apparatuses, including data processing, was in accordance with the methods and procedures instructed for each apparatus.

Synthesis Example 1

Synthesis of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I))

Synthesis Example 1 (1)

Synthesis of tert-Butyl (2S,4R)-4-(4-amino-5-iodo-7H-pyrrolo[2,3-d]pyrimidin-7-yl)-2-methylpyrrolidine-1-carboxylate tert-Butyl (2S,4S)-4-hydroxy-2-methylpyrrolidine-1-carboxylate (19.0 g) and 4-chloro-5-iodo-7H-pyrrolo[2,3-d]pyrimidine (13.1 g) were dissolved in THF (190 mL), and the obtained solution was then cooled to 0° C. Thereafter, triphenylphosphine (37.2 g) and diisopropyl azodicarboxylate (28.1 mL) were added to the reaction solution, and the temperature of the mixture was then increased to room temperature, followed by stirring for 1 hour. Thereafter, the reaction mixture was concentrated under reduced pressure, and the obtained residue was then purified by silica gel chromatography (hexane:ethyl acetate) to obtain the corresponding coupling body. The obtained compound was used in the subsequent reaction without being further purified.

The obtained coupling body, THF (114 mL) and ammonia water (114 mL) were added into a pressure resistant tube, and the obtained mixture was then stirred at 100° C. for 14 hours. Thereafter, the reaction mixture was cooled to room temperature, and was then poured into water (285 mL). The thus obtained mixture was stirred at room temperature for 5 hours. Thereafter, the precipitated solid was collected by filtration, was then washed with water, and was then dried to obtain a product of interest (34.5 g).

$^1$HNMR ($CDCl_3$) δ: 8.27 (s, 1H) 7.15 (s, 1H) 5.55-5.73 (m, 2H) 5.12-5.25 (m, 1H) 3.86-4.18 (m, 2H) 3.43-3.57 (m, 1H) 2.59-2.69 (m, 1H) 1.92-2.03 (m, 1H) 1.48 (s, 9H) 1.30-1.40 (m, 3H) ESI-MS m/z 444 ($MH^+$)

Synthesis Example 1 (2)

Synthesis of 4-Amino-7-((3R,5S)-1-(tert-butoxycarbonyl)-5-methylpyrrolidin-3-yl)-7H-pyrrolo[2,3-d]pyrimidine-5-carboxylic acid The compound of Synthesis Example 1 (1) (28.0 g), 10% palladium carbon catalyst (720 mg), NMP (84 mL), methanol (26 mL), and triethylamine (17.6 mL) were added into a pressure resistant tube, followed by carbon monoxide substitution, and the obtained mixture was stirred at 100° C. for 2 hours. Thereafter, the reaction mixture was cooled to room temperature, a 2 M sodium hydroxide aqueous solution (79 mL) was then added thereto, and the obtained mixture was then stirred at 80° C. for 2 hours. Thereafter, the reaction mixture was cooled to room temperature, was then filtrated through Celite, and was then washed with methanol. Subsequently, methanol in the filtrate was concentrated under reduced pressure. Water was further added, and the water layer was then washed with tert-butyl methyl ether. A 1 M potassium hydrogen sulfate aqueous solution was added to the water layer to adjust the pH to approximately 3. The precipitated solid was collected by filtration, was then washed with water, and was then dried to obtain a product of interest (23.4 g).

$^1$HNMR (400 MHz, DMSO-d6) δ: 8.14 (s, 1H) 8.08 (s, 1H) 5.16-4.93 (m, 1H) 4.07-3.79 (m, 2H) 3.61-3.45 (m, 1H) 2.53 (m, 1H) 2.33-2.02 (m, 1H) 1.42 (s, 9H) 1.29 (d, J=6.1 Hz, 3H) ESI-MS m/z 362 ($MH^+$)

Synthesis Example 1 (3)

Synthesis of tert-Butyl (2S,4R)-4-(4-amino-6-bromo-5-(((R)-1-phenylethyl) carbamoyl)-7H-pyrrolo[2,3-d]pyrimidin-7-yl)-2-methylpyrrolidine-1-carboxylate The compound of Synthesis Example 1 (2) (1.00 g), (R)-(+)-1-phenylethylamine (0.503 g), diisopropylethylamine (1.79 g), and N,N-dimethylformamide (10 mL) were added, and subsequently, HATU (1.58 g) was added. The obtained mixture was stirred at room temperature overnight. Thereafter, to the reaction mixture, ethyl acetate and a saturated sodium hydrogen carbonate aqueous solution were added, and the obtained mixture was then extracted with ethyl acetate. The gathered organic layer was washed with water, and then with saturated saline. The resultant was dried over anhydrous sodium sulfate, and was then concentrated under reduced pressure. The obtained residue was purified by silica gel chromatography (hexane: acetone) to obtain an amide form (1.53 g). The obtained compound was used in the subsequent reaction without being further purified.

To the amide form (1.53 g), chloroform (15 mL) was added, and the obtained mixture was then cooled to 0° C. Thereafter, N-bromosuccinimide (0.88 g) was added to the reaction mixture, and the obtained mixture was then stirred at 0° C. for 1 hour. Thereafter, the reaction mixture was concentrated under reduced pressure, and the obtained residue was purified by silica gel chromatography (hexane:ethyl acetate) to obtain a product of interest (1.39 g).

$^1$HNMR ($CDCl_3$) δ: 8.21 (s, 1H) 7.42-7.28 (m, 5H) 6.97 (d, J]=7.3 Hz, 1H) 5.36-5.29 (m, 1H) 5.20-5.07 (m, 1H) 4.30 (t, J=10.3 Hz, 1H) 4.04-3.72 (m, 2H) 3.00-2.86 (m, 1H) 2.38 (dt, J=14.3, 6.0 Hz, 1H) 1.63 (d, J=7.0 Hz, 3H) 1.53-1.43 (m, 12H)

ESI-MS m/z 543,545 ($MH^+$)

Synthesis Example 1 (4)

7-((3R,5S)-1-acryloyl-5-methylpyrrolidin-3-yl)-4-amino-6-bromo-N-((R)-1-phenylethyl)-7H-pyrrolo[2,3-d]pyrimidine-5-carboxamide To the compound of Synthesis Example 1 (3) (600 mg), chloroform (3 mL) was added, and the obtained mixture was then cooled to 0° C. Thereafter, trifluoroacetic acid (4.44 g) was added to the reaction mixture, and the thus obtained mixture was then stirred at room temperature for 1 hour. Thereafter, the reaction mixture was concentrated under reduced pressure, and acetonitrile (5 mL) was then added to the residue. The obtained mixture was concentrated under reduced pressure again to obtain an amine form. The obtained compound was used in the subsequent reaction without being further purified.

To the obtained amine form, acetonitrile (3 mL) was added, and the obtained mixture was then cooled to 0° C. Thereafter, acryloyl chloride (99.9 mg) and diisopropylethylamine (713 mg) were added, and the obtained mixture was then stirred at 0° C. for 1 hour. Thereafter, the reaction mixture was concentrated under reduced pressure, and the obtained residue was purified by silica gel chromatography (ethyl acetate: methanol) to obtain a product of interest (281 mg).

$^1$HNMR ($CDCl_3$) δ: 8.20 (d, J=7.3 Hz, 1H) 7.42-7.36 (m, 4H) 7.32-7.28 (m, 1H) 7.00-6.94 (m, 1H) 6.57-6.33 (m, 2H) 5.76-5.66 (m, 1H) 5.36-5.29 (m, 1H) 5.14-5.08 (m, 1H) 4.71 (t, J=9.9 Hz, 0.7H) 4.42-4.23 (m, 1.6H) 3.83 (t, J=8.6 Hz, 0.7H) 3.03-2.92 (m, 1H) 2.60-2.57 (m, 0.3H) 2.44-2.40 (m, 0.7H) 1.64 (d, J=6.6 Hz, 3H) 1.56 (dd, J=11.7, 6.2 Hz, 3H) ESI-MS m/z 497,499 ($MH^+$)

Synthesis Example 1 (5)

Synthesis of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I))

The compound of Synthesis Example 1 (4) (65 mg), dichlorobis(triphenylphosphine)dipalladium (9.2 mg), copper (I) iodide (5.0 mg), cyclopropylacetylene (13.0 mg), triethylamine (39.7 mg), and N,N-dimethylformamide (1.3 mL) were added, and the inside of the reaction system was then substituted with nitrogen. After that, the mixture was stirred at 70° C. for 2.5 hours. Thereafter, to the reaction mixture, ethyl acetate and a saturated ammonium chloride aqueous solution were added, and the obtained mixture was then extracted with ethyl acetate. The gathered organic layer was washed with water, and then with saturated saline. The resultant was dried over anhydrous sodium sulfate, and was then concentrated under reduced pressure. The obtained residue was purified by silica gel chromatography (chloroform:methanol) to obtain a product of interest (50 mg).

$^1$HNMR ($CDCl_3$) δ: 8.22 (d, J=5.1 Hz, 1H) 7.82 (d, J=7.3 Hz, 1H) 7.43-7.35 (m, 4H) 7.30 (t, J=6.8 Hz, 1H) 6.58-6.34 (m, 2H) 5.77-5.66 (m, 1H) 5.35-5.20 (m, 2H) 4.54 (t, J=10.1 Hz, 0.7H) 4.35-4.25 (m, 1.6H) 3.88 (t, J=8.8 Hz, 0.7H) 2.90-2.78 (m, 1H) 2.65-2.56 (m, 0.3H) 2.49-2.40 (m, 0.7H) 1.63 (d, J=7.0 Hz, 3H) 1.56-1.45 (m, 4H) 1.03-0.91 (m, 2H) 0.84-0.69 (m, 2H)

ESI-MS m/z 483 ($MH^+$)

Example 1

Production of Type II Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 1 Equivalent of Fumaric Acid Type II crystals of the compound (I) with fumaric acid were produced by the two methods described below in Production Method 1 and Production Method 2. A free-form type I crystal of compound (I) was synthesized by the same method as in Example 3 described later.

(i) Production Method 1

Fumaric acid (3 equivalents) was added to 30 mg of a free-form type I crystal of compound (I), 0.3 mL of tert-butanol was added, the suspension was stirred at 25° C. for approximately 124 hours, and then the solid was collected by filtration, recovered, and dried to obtain a crystal of interest.

(ii) Production Method 2

Fumaric acid (1.06 g) and 22 mL of acetone were added to 2.20 g of a free-form type I crystal of compound (I), the suspension was stirred at 50° C. for approximately 62 hours, naturally cooled for 30 minutes, and then the solid was collected by filtration and recovered. This was washed with 2-propanol, and then the solid was collected by filtration, recovered, and dried to obtain 2.27 g of a crystal of interest.

Powder X-ray diffraction spectrum (Method A): See FIG. 1. The powder X-ray diffraction spectral data are shown in Table 2.

TABLE 2

Powder X-ray diffraction spectral data of type II crystal of compound (I) with 1 equivalent of fumaric acid

| Peak position [° 2θ] | Net intensity [cts] |
|---|---|
| 5.5 | 1065 |
| 6.8 | 489 |
| 8.1 | 187 |
| 9.3 | 370 |
| 10.8 | 54 |
| 12.1 | 107 |
| 13.4 | 564 |
| 14.0 | 319 |
| 14.6 | 171 |
| 15.3 | 771 |
| 16.3 | 602 |
| 17.1 | 101 |
| 18.5 | 1706 |
| 19.8 | 516 |
| 20.5 | 236 |
| 22.0 | 1123 |
| 22.6 | 101 |
| 23.3 | 129 |
| 23.8 | 151 |
| 24.5 | 929 |
| 25.1 | 676 |
| 25.5 | 774 |
| 26.2 | 432 |
| 27.2 | 455 |
| 27.3 | 358 |
| 27.9 | 144 |
| 28.1 | 137 |
| 29.0 | 154 |
| 29.9 | 183 |
| 30.9 | 106 |
| 32.0 | 73 |
| 32.9 | 104 |
| 34.3 | 174 |
| 35.1 | 125 |
| 38.2 | 105 |
| 39.1 | 114 |

In addition, the characteristic diffraction angles are as follows.

Characteristic diffraction angle (2θ±0.2°):

5.5°, 6.8°, 9.3°, 13.4°, 15.3°, 16.3°, 18.5°, 19.8°, 22.0°, and 24.5°

Simultaneous thermogravimetry-differential thermal analysis curve: See FIG. 2.

Endothermic peak (peak top value) in the simultaneous thermogravimetry-differential thermal analysis curve: Around 182° C.

Example 2

Production of free-form type II crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I))

Free-form type II crystals were produced by the four methods described below in Production Methods 1 to 4.

(i) Production Method 1

Succinic acid (1 equivalent) and 0.3 mL of 1-propanol/water (1:3 v/v) were added to 15 mg of the compound (I) obtained according to the method in Synthesis Example 1, the mixture was suspended and stirred at 50° C. for 4 days, and then the solid was collected by filtration, recovered, and dried to obtain a crystal of interest.

(ii) Production Method 2

Succinic acid (1 equivalent) and 1.5 mL of 1-propanol/water (1:3 v/v) were added to 300 mg of the compound (I)

obtained according to the method in Synthesis Example 1, a small amount of the crystals obtained in (i) was added as a seed crystal, the mixture was suspended and stirred at 50° C. for 5 hours, and then 0.3 mL of 1-propanol was added, the mixture was further suspended and stirred at 50° C. for 2 hours, and then 0.3 mL of 1-propanol was added, the mixture was suspended and stirred at 50° C. for 17 hours, and then the solid was collected by filtration, recovered, and dried to obtain 84.5 mg of a crystal of interest.

(iii) Production Method 3

Succinic acid (1 equivalent) and 3 mL of 1-propanol/water (1:1 v/v) were added to 1000 mg of the compound (I) obtained according to the method in Synthesis Example 1, a small amount of the crystals obtained in (ii) was added as a seed crystal, the mixture was suspended and stirred at 50° C. for 17.5 hours, and then the solid was collected by filtration (washing with water during filtration), recovered, and dried to obtain 487.6 mg of a crystal of interest.

(iv) Production Method 4

Diisopropyl ether (5 mL) was added to 1000 mg of the compound (I) obtained according to the method in Synthesis Example 1, a small amount of the crystals obtained in (iii) was added as a seed crystal, and the mixture was suspended and stirred at 50° C. After 42.5 hours, as the solvent had evaporated, 5 mL of diisopropyl ether was added. The mixture was suspended and stirred at 50° C. for 2 hours, and then 0.5 mL of ethanol was added. The mixture was further suspended and stirred at 50° C. for 2 hours, and then 0.5 mL of ethanol was added. The mixture was further suspended and stirred at 50° C. for 19 hours, and naturally cooled for 30 minutes, and then the solid was collected by filtration, recovered, and dried to obtain 798.8 mg of a crystal of interest.

Powder X-ray diffraction spectrum (Method A): See FIG. 3. The powder X-ray diffraction spectral data are shown in Table 3.

TABLE 3

Powder X-ray diffraction spectral data of free-form type II crystal of compound (I)

| Peak position [° 2θ] | Net intensity [cts] |
|---|---|
| 8.3 | 1844 |
| 9.7 | 179 |
| 10.2 | 531 |
| 11.5 | 248 |
| 12.5 | 660 |
| 13.6 | 440 |
| 14.8 | 2512 |
| 15.8 | 530 |
| 16.0 | 105 |
| 16.5 | 641 |
| 16.9 | 117 |
| 17.3 | 2130 |
| 18.0 | 945 |
| 18.3 | 269 |
| 19.1 | 844 |
| 19.4 | 154 |
| 20.3 | 852 |
| 21.0 | 963 |
| 21.6 | 271 |
| 21.9 | 520 |
| 22.5 | 957 |
| 23.0 | 1442 |
| 23.8 | 559 |
| 23.9 | 980 |
| 24.7 | 418 |
| 25.0 | 367 |
| 25.5 | 208 |
| 26.2 | 1551 |
| 26.8 | 323 |
| 27.2 | 771 |
| 27.6 | 218 |
| 28.3 | 100 |
| 28.6 | 101 |
| 29.7 | 374 |
| 30.9 | 113 |
| 31.7 | 261 |
| 32.3 | 148 |
| 34.0 | 229 |
| 34.6 | 159 |
| 35.3 | 87 |
| 36.4 | 59 |
| 37.0 | 123 |
| 37.7 | 60 |
| 38.6 | 53 |
| 39.0 | 55 |

In addition, the characteristic diffraction angles are as follows.

Characteristic diffraction angle (2θ±0.2°):

8.3°, 14.8°, 17.3°, 18.0°, 19.1°, 20.3°, 21.0°, 22.5°, 23.0°, and 26.2°

Simultaneous thermogravimetry-differential thermal analysis curve: See FIG. 4.

Endothermic peak (peak top value) in the simultaneous thermogravimetry-differential thermal analysis curve: Around 182° C.

Example 3

Production of free-form type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I))

A crude product (100 mg) of the compound (I) was suspended in ethanol (500 μL) and stirred at 50° C. overnight. The solution was cooled to 25° C. and the obtained suspension was filtrated to obtain a free-form type I crystal of compound (I) (31 mg).

Powder X-ray diffraction spectrum (Method A): See FIG. 5. The powder X-ray diffraction spectral data are shown in Table 4.

TABLE 4

Powder X-ray diffraction spectral data of free-form type I crystal of compound (I)

| Peak position [° 2θ] | Net intensity [cts] |
|---|---|
| 9.9 | 623 |
| 10.4 | 278 |
| 11.7 | 1459 |
| 12.0 | 457 |
| 13.2 | 618 |
| 14.8 | 74 |
| 15.7 | 588 |
| 16.0 | 558 |
| 17.7 | 730 |

TABLE 4-continued

| Powder X-ray diffraction spectral data of free-form type I crystal of compound (I) | |
|---|---|
| Peak position [° 2θ] | Net intensity [cts] |
| 18.1 | 1070 |
| 18.8 | 1539 |
| 19.7 | 120 |
| 20.1 | 382 |
| 20.8 | 2893 |
| 21.5 | 481 |
| 22.4 | 437 |
| 23.3 | 198 |
| 23.9 | 297 |
| 24.3 | 230 |
| 24.9 | 293 |
| 25.5 | 379 |
| 26.1 | 321 |
| 27.1 | 99 |
| 28.0 | 183 |
| 28.3 | 545 |
| 28.9 | 391 |
| 29.5 | 168 |
| 29.8 | 105 |
| 30.3 | 208 |
| 31.0 | 72 |
| 31.8 | 113 |
| 32.2 | 114 |
| 32.5 | 108 |
| 33.0 | 126 |
| 33.6 | 171 |
| 34.7 | 68 |
| 35.5 | 82 |
| 36.9 | 80 |
| 37.2 | 55 |
| 38.0 | 50 |

In addition, the characteristic diffraction angles are as follows.

Characteristic diffraction angle (2θ±0.2°): 9.9°, 11.7°, 13.2°, 17.7°, 18.1°, 18.8°, and 20.8°

Simultaneous thermogravimetry-differential thermal analysis curve: See FIG. 6.

Endothermic peak (peak top value) in the simultaneous thermogravimetry-differential thermal analysis curve: Around 183° C.

Example 4

Production of Type V Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 1 Equivalent of Fumaric Acid Fumaric acid (481 mg) and 50 mL of acetone were added to 1000 mg of the compound (I) obtained according to the method in Synthesis Example 1, the mixture was suspended and stirred at 25° C. for 71 hours, and then the solid was collected by filtration and recovered. This was dried under room temperature and reduced pressure conditions for 7.5 hours to obtain695.0 mg of a crystal of interest.

Powder X-ray diffraction spectrum (Method A): See FIG. 7. The powder X-ray diffraction spectral data are shown in Table 5.

TABLE 5

| Powder X-ray diffraction spectral data of type V crystal of compound (I) with 1 equivalent of fumaric acid | |
|---|---|
| Peak position [° 2θ] | Net intensity [cts] |
| 6.9 | 180 |
| 8.7 | 184 |
| 9.4 | 470 |
| 10.2 | 450 |
| 11.9 | 197 |
| 13.7 | 219 |
| 14.5 | 199 |
| 15.9 | 350 |
| 17.5 | 356 |
| 18.1 | 201 |
| 18.7 | 278 |
| 20.1 | 319 |
| 21.1 | 481 |
| 21.7 | 215 |
| 23.1 | 343 |
| 23.8 | 573 |
| 24.6 | 206 |
| 26.5 | 519 |
| 27.5 | 235 |
| 28.2 | 140 |
| 29.0 | 103 |
| 31.0 | 92 |
| 32.4 | 65 |
| 33.0 | 54 |
| 34.4 | 74 |

In addition, the characteristic diffraction angles are as follows.

Characteristic diffraction angle (2θ±0.2°): 6.9°, 9.4°, 10.2°, 13.7°, 21.1°, 23.6°, and 26.5°

Simultaneous thermogravimetry-differential thermal analysis curve: See FIG. 8.

Endothermic peak (peak top value) in the simultaneous thermogravimetry-differential thermal analysis curve: Around 151° C.

Example 5

Production of Type I Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 1 Equivalent of Fumaric Acid Fumaric acid (481 mg) and 50 mL of acetone were added to 1000 mg of the compound (I) obtained according to the method in Synthesis Example 1, the mixture was suspended and stirred at 25° C. for 19.5 hours, and then the solid was collected by filtration and recovered to obtain 868.8 mg of a crystal of interest.

Powder X-ray diffraction spectrum (Method A): See FIG. 9. The powder X-ray diffraction spectral data are shown in Table 6.

TABLE 6

| Powder X-ray diffraction spectral data of type I crystal of compound (I) with 1 equivalent of fumaric acid | |
|---|---|
| Peak position [° 2θ] | Net intensity [cts] |
| 6.4 | 637 |
| 8.5 | 145 |

TABLE 6-continued

| Powder X-ray diffraction spectral data of type I crystal of compound (I) with 1 equivalent of fumaric acid | |
|---|---|
| Peak position [° 2θ] | Net intensity [cts] |
| 8.8 | 115 |
| 10.3 | 461 |
| 11.4 | 321 |
| 12.8 | 279 |
| 14.4 | 172 |
| 15.0 | 393 |
| 15.7 | 326 |
| 16.0 | 422 |
| 16.9 | 206 |
| 17.8 | 129 |
| 18.4 | 290 |
| 19.2 | 145 |
| 19.4 | 151 |
| 20.7 | 938 |
| 21.4 | 195 |
| 22.1 | 146 |
| 22.9 | 451 |
| 23.4 | 690 |
| 24.2 | 157 |
| 24.8 | 146 |
| 26.6 | 931 |
| 28.1 | 112 |
| 28.9 | 164 |
| 30.3 | 70 |
| 30.8 | 75 |
| 31.6 | 77 |
| 32.9 | 138 |
| 33.4 | 81 |
| 34.6 | 57 |

In addition, the characteristic diffraction angles are as follows.

Characteristic diffraction angle (2θ±0.2°): 6.4°, 10.3°, 12.8°, 15.0°, 20.7°, 23.4°, and 26.6°

Simultaneous thermogravimetry-differential thermal analysis curve: See FIG. 10.

Endothermic peak (peak top value) in the simultaneous thermogravimetry-differential thermal analysis curve: Around 153° C.

Example 6

Production of Type I Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 0.5 Equivalent of Fumaric Acid Fumaric acid (0.5 equivalents) and 0.3 mL of water were added to 15 mg of the compound (I) obtained according to the method in Synthesis Example 1, the mixture was suspended and stirred at 50° C. for 93.5 hours, and then the solid was collected by filtration, recovered, and dried to obtain a crystal of interest.

Powder X-ray diffraction spectrum (Method B): See FIG. 11.

Characteristic diffraction angle (2θ±0.2°): 6.4°, 7.5°, 9.7°, 11.7°, 15.1°, 19.6°, and 23.9°

Simultaneous thermogravimetry-differential thermal analysis curve: See FIG. 12.

Endothermic peak (peak top value) in the simultaneous thermogravimetry-differential thermal analysis curve: Around 161° C.

Example 7

Production of Type II Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 0.5 Equivalents of Fumaric Acid Fumaric acid (1 equivalent) and 6 mL of ethanol were added to 300 mg of the compound (I) obtained according to the method in Synthesis Example 1, the mixture was suspended and stirred at 50° C. for 19.5 hours and naturally cooled for 3 hours, and then the solid was collected by filtration and recovered. This was washed with water, and then the solid was collected by filtration, recovered, and dried to obtain 224.6 mg of a crystal of interest.

Powder X-ray diffraction spectrum: See FIG. 13.

Characteristic diffraction angle (2θ±0.2°): 5.4°, 6.4°, 7.3°, 12.8°, 13.4°, 14.7°, and 15.4°

Simultaneous thermogravimetry-differential thermal analysis curve: See FIG. 14.

Endothermic peak (peak top value) in the simultaneous thermogravimetry-differential thermal analysis curve: Around 162° C.

Example 8 Analysis of Molar Ratio of Compound (I) and Fumaric Acid

The molar ratio of compound (I) and fumaric acid and the molar ratio of compound (I) and L-tartaric acid were confirmed by 1H-NMR. The measurement results of the NMR spectrum of the type I crystal of compound (I) with 1 equivalent of fumaric acid, the type II crystal of compound (I) with 1 equivalent of fumaric acid, and the type V crystal of compound (I) with 1 equivalent of fumaric acid are shown below. The measurement results of the NMR spectra of the free form I crystal of compound (I) and the free form II crystal of compound (I) are also shown below.

(Free Form I Crystal of Compound (I))

$^1$HNMR (400 MHz, DMSO-d6) δ: 8.32 (brd, J=7.38 Hz, 1H) 8.14 (s, 1H) 7.25-7.50 (m, 5H) 6.54-6.72 (m, 1H) 6.13-6.23 (m, 1H) 5.65-5.76 (m, 1H) 5.12-5.39 (m, 2H) 4.33-4.40 (m, 1H) 4.00-4.22 (m, 2H) 2.44-2.70 (m, 2H) 1.73 (tt, J=4.99, 8.27 Hz, 1H) 1.51 (d, J=6.88 Hz, 3H) 1.36-1.43 (m, 3H) 0.78-1.03 (m, 4H)

(Free Form II Crystal of Compound (I))

$^1$HNMR (400 MHz, DMSO-d6) δ: 8.32 (brd, J=7.38 Hz, 1H) 8.14 (s, 1H) 7.27-7.46 (m, 5H) 6.54-6.72 (m, 1H) 6.13-6.23 (m, 1H) 5.65-5.76 (m, 1H) 5.12-5.39 (m, 2H) 4.32-4.40 (m, 1H) 4.00-4.22 (m, 2H) 2.44-2.69 (m, 2H) 1.73 (tt, J=4.99, 8.27 Hz, 1H) 1.51 (d, J=6.88 Hz, 3H) 1.40-1.43 (m, 3H) 0.78-1.03 (m, 4H)

(Type I Crystal of Compound (I) with 1 Equivalent of Fumaric Acid)

$^1$HNMR (400 MHz, DMSO-d6) δ: 13.13 (brs, 2H) 8.32 (brd, J=7.38 Hz, 1H) 8.14 (s, 1H) 7.24-7.48 (m, 5H) 6.46-6.78 (m, 3H) 6.06-6.30 (m, 1H) 5.63-5.77 (m, 1H) 5.11-5.38 (m, 2H) 4.27-4.44 (m, 1H) 3.98-4.23 (m, 2H) 2.42-2.73 (m, 2H) 1.73 (tt, J=5.02, 8.30 Hz, 1H) 1.51 (d, J-6.88 Hz, 3H) 1.32-1.45 (m, 3H) 0.77-1.02 (m, 4H)

(Type II Crystal of Compound (I) with 1 Equivalent of Fumaric Acid)

$^1$HNMR (400 MHz, DMSO-d6) δ: 13.14 (brs, 2H) 8.32 (brd, J=7.38 Hz, 1H) 8.14 (s, 1H) 7.25-7.49 (m, 5H) 6.39-6.89 (m, 3H) 6.07-6.28 (m, 1H) 5.62-5.77 (m, 1H) 5.12-5.39 (m, 2H) 4.27-4.45 (m, 1H) 3.99-4.24 (m, 2H)

2.42-2.75 (m, 2H) 1.74 (tt, J=5.02, 8.30 Hz, 1H) 1.51 (d, J=6.88 Hz, 3H) 1.37-1.46 (m, 3H) 0.78-1.03 (m, 4H)

(Type V Crystal of Compound (I) with 1 Equivalent of Fumaric Acid)

$^1$HNMR (400 MHz, DMSO-d6) δ: 13.13 (brs, 2H) 8.32 (brd, J=7.38 Hz, 1H) 8.14 (s, 1H) 7.21-7.49 (m, 5H) 6.47-6.80 (m, 3H) 6.09-6.26 (m, 1H) 5.63-5.77 (m, 1H) 5.11-5.38 (m, 2H) 4.27-4.44 (m, 1H) 3.98-4.23 (m, 2H) 2.42-2.72 (m, 2H) 1.73 (tt, J=4.99, 8.27 Hz, 1H) 1.51 (d, J=6.88 Hz, 3H) 1.34-1.46 (m, 3H) 0.77-1.02 (m, 4H)

Reference Example 1

Production of Type III Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 1 Equivalent of Fumaric Acid Fumaric acid (3 equivalents) and 9 mL of acetonitrile were added to 300 mg of the compound (I) obtained according to the method in Synthesis Example 1, the mixture was suspended and stirred at 50° C. for 1 hour and naturally cooled, and then the solid was collected by filtration and recovered. This was dried to obtain 303.7 mg of a crystal of interest.

Powder X-ray diffraction spectrum (Method B): See FIG. 15.

Characteristic diffraction angle (2θ±0.2°): 8.1°, 13.2°, 20.4°, 23.1°, 24.7°, and 26.1°

Simultaneous thermogravimetry-differential thermal analysis curve: See FIG. 16.

Exothermic peak (peak top value) in the simultaneous thermogravimetry-differential thermal analysis curve: Around 153° C.

Reference Example 2

Production of Type IV Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 1 Equivalent of Fumaric Acid Fumaric acid (3 equivalents) and 6 mL of water were added to 300 mg of the compound (I) obtained according to the method in Synthesis Example 1, the mixture was suspended and stirred at 50° C. for 1.5 hours and naturally cooled for 3 hours, and then the solid was collected by filtration and recovered. This was washed with water, and then the solid was collected by filtration, recovered, and dried to obtain 311.2 mg of a crystal of interest.

Powder X-ray diffraction spectrum (Method B): See FIG. 17.

Characteristic diffraction angle (2θ±0.2°): 6.0°, 15.7°, and 18.8°

Simultaneous thermogravimetry-differential thermal analysis curve: See FIG. 18.

Exothermic peak (peak top value) in the simultaneous thermogravimetry-differential thermal analysis curve: Around 130° C.

Reference Example 3

Production of Type I Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with Hydrochloric Acid A 2M hydrochloric acid/ethanol solution (15 μL) and 0.3 mL of a liquid mixture of 2-propanol/heptane (1:3 v/v) were added to 15 mg of the compound (I) obtained according to the method in Synthesis Example 1, the mixture was suspended and stirred for 4 days and naturally cooled, and then the solid was collected by filtration and recovered. This was dried to obtain a crystal of interest.

Powder X-ray diffraction spectrum (Method B): See FIG. 19.

Characteristic diffraction angle (2θ±0.2°): 7.0°, 7.4°, 12.6°, 19.0°, and 25.4°

Simultaneous thermogravimetry-differential thermal analysis curve: See FIG. 20.

Endothermic peak (peak top value) in the simultaneous thermogravimetry-differential thermal analysis curve: Around 51° C. and 179° C.

Reference Example 4

Production of Type II Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with Hydrochloric Acid A 2M hydrochloric acid/ethanol solution (15 μL) and 0.3 mL of a liquid mixture of acetone/heptane (1:3 v/v) were added to 15 mg of the compound (I) obtained according to the method in Synthesis Example 1, the mixture was suspended and stirred for 4 days and naturally cooled, and then the solid was collected by filtration and recovered. This was dried to obtain a crystal of interest.

Powder X-ray diffraction spectrum (Method B): See FIG. 21.

Characteristic diffraction angle (2θ±0.2°): 6.3°, 7.4°, 8.0°, 17.6°, 22.0°, and 23.6°

Simultaneous thermogravimetry-differential thermal analysis curve: See FIG. 22.

Endothermic peak (peak top value) in the simultaneous thermogravimetry-differential thermal analysis curve: Around 147° C.

Reference Example 5

Production of Type III Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with Hydrochloric Acid A 2M hydrochloric acid/ethanol solution (15 μL) and 0.3 mL of ethyl acetate were added to 15 mg of the compound (I) obtained according to the method in Synthesis Example 1, the mixture was suspended and stirred for 4 days and naturally cooled, and then the solid was collected by filtration and recovered. This was dried to obtain a crystal of interest.

Powder X-ray diffraction spectrum (Method B): See FIG. 23.

Characteristic diffraction angle (2θ±0.2°): 5.3°, 6.5°, 8.1°, 15.3°, and 24.2°

Simultaneous thermogravimetry-differential thermal analysis curve: See FIG. 24.

Endothermic peak (peak top value) in the simultaneous thermogravimetry-differential thermal analysis curve: Around 156° C.

Reference Example 6

Production of Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with Hydrobromic Acid Hydrobromic acid (1 equivalent) and 0.3 mL of a liquid mixture of 2-propanol/heptane (1:3 v/v) were added to 15 mg of the compound (I) obtained according to the method in Synthesis Example 1, the mixture was suspended and stirred for 5 days and naturally cooled, and then the solid was collected by filtration and recovered. This was dried to obtain a crystal of interest.

Powder X-ray diffraction spectrum (Method B): See FIG. 25.

Characteristic diffraction angle (2θ±0.2°): 7.0°, 7.4°, 13.4°, 15.6°, 19.2°, and 25.6°

Simultaneous thermogravimetry-differential thermal analysis curve: See FIG. 26.

Endothermic peak (peak top value) in the simultaneous thermogravimetry-differential thermal analysis curve: Around 204° C.

Reference Example 7

Production of Type IV Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with 1 Equivalent of L-Tartaric Acid L-tartaric acid (466 mg) and 10 mL of acetone were added to 500 mg of the compound (I) obtained according to the method in Synthesis Example 1, the mixture was stirred at 50° C. for 40 minutes for dissolution. Thereafter, the dissolved mixture was stirred at room temperature for 17 hours, the suspension was filtrated, and the resulting solid was recovered. This was dried to obtain 506.3 mg of a crystal of interest.

Powder X-ray diffraction spectrum (Method A): See FIG. 27.

Characteristic diffraction angle (2θ—+0.2°): 7.2°, 12.6°, 17.3°, and 23.4°

Simultaneous thermogravimetry-differential thermal analysis curve: See FIG. 28.

Endothermic peak (peak top value) in the simultaneous thermogravimetry-differential thermal analysis curve: Around 121° C.

Reference Example 8

Production of Crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide (Compound (I)) with Succinic Acid Succinic acid (3 equivalents) and 0.3 mL of acetonitrile were added to 15 mg of the compound (I) obtained according to the method in Synthesis Example 1, the mixture was suspended and stirred at 50° C. for 3 days and naturally cooled, and then the solid was collected by filtration and recovered. This was dried to obtain a crystal of interest.

Powder X-ray diffraction spectrum (Method B): See FIG. 29.

Characteristic diffraction angle (2θ±0.2°): 6.5°, 10.7°, 13.2°, 14.6°, 18.7°, and 23.9°

Simultaneous thermogravimetry-differential thermal analysis curve: See FIG. 30.

Endothermic peak (peak top value) in the simultaneous thermogravimetry-differential thermal analysis curve: Around 148° C. and 159° C.

Test Example 1 Measurement of Inhibitory Effect (In Vitro) on HER2 Phosphorylation Activity In order to determine conditions for a method of measuring the in vitro inhibitory activity of a compound against HER2 phosphorylation activity, based on the report regarding a HER2 kinase reaction using, as a substrate, a peptide having the same sequence (5-FAM-EEPLYWSFPAKKK-$CONH_2$) as that of ProfilerPro Peptide 22 of PerkinElmer (Xie H et al., PLOS One. 2011; 6 (7): e21487), ProfilerPro Peptide 22 was used as a substrate. A purified recombinant human HER2 protein used in the present test was purchased from Carna Biosciences, Inc. Upon the measurement of the inhibitory activity of the compound, first, the compound (I) obtained according to the method in Synthesis Example 1 was diluted stepwise with dimethyl sulfoxide (DMSO). Subsequently, the HER2 protein, the substrate peptide (final concentration: 1 μM), manganese chloride (final concentration: 10 mM), ATP (final concentration: 5 μM), and the compound (I) in DMSO solution (final concentration of DMSO: 5%) were added to a buffer for the kinase reaction (13.5 mM Tris (pH 7.5), 2 mM dithiothreitol, and 0.009% Tween 20), and the obtained mixture was then incubated at 25° C. for 30 minutes, so that the kinase reaction was carried out. To the reaction solution, EDTA was added to a final concentration of 30 mM, so as to terminate the reaction. Finally, using LabChip (registered trademark) EZ Reader II (PerkinElmer), an unphosphorylated substrate peptide(S) and a phosphorylated peptide (P) were separated and detected according to microchannel capillary electrophoresis. From the peak heights of S and P, the amount of the phosphorylation reaction was obtained, and the concentration of the compound capable of inhibiting the phosphorylation reaction by 50% was defined as an IC50 value (nM). The results are shown in Table 1.

Test Example 2 Measurement of Inhibitory Action (In Vitro) Against HER2 Exon 20 Insertion Mutant (HER2Ex20insYVMA) Phosphorylation Activity In order to determine conditions for a method of measuring the in vitro inhibitory activity of a compound against HER2 exon 20 insertion mutant phosphorylation activity, as in the case of HER2, ProfilerPro Peptide 22 was used as a substrate. A purified recombinant human HER2 exon 20 insertion mutant (A775_G776insYVMA) protein was purchased from SignalChem. Upon the measurement of the inhibitory activity of the compound, first, the compound (I) obtained according to the method in Synthesis Example 1 was diluted stepwise with dimethyl sulfoxide (DMSO). Subsequently, the HER2 exon 20 insertion mutant protein and the compound (I) in DMSO solution (final concentration of DMSO: 5%) were added into a buffer for the kinase reaction (13.5 mM Tris (pH 7.5), 2 mM dithiothreitol, and 0.009% Tween 20), and the obtained mixture was then pre-incubated at 25° C. for 30 minutes. Thereafter, the substrate peptide (final concentration: 1 μM), manganese chloride (final concentration: 25 mM), magnesium chloride (final concentration: 20 mM), and ATP (final concentration: 200 μM) were added into the reaction mixture, and the thus obtained mixture was then incubated at 25° C. for 220 minutes, so that the kinase reaction was carried out. To the reaction solution, EDTA was added to a final concentration of 30 mM, so as to terminate the reaction. Finally, using LabChip (registered trademark) EZ Reader II (PerkinElmer), an unphosphorylated substrate peptide(S) and a phosphorylated peptide (P) were separated and detected according to microchannel capillary electrophoresis. From the peak heights of S and P, the amount of the phosphorylation reaction was obtained, and the concentration of the compound capable of inhibiting the phosphorylation reaction by 50% was defined as an IC50 value (nM). The results are shown in Table 7.

TABLE 7

| HER2 inhibitory activity IC50 value (nM) | HER2ex20insYVMA inhibitory activity IC50 value (nM) |
|---|---|
| 3.2 | <0.30 |

From the above results, it was found that the compound (I) has excellent inhibitory activity against phosphorylation of HER2 and against phosphorylation of HER2 exon 20 insertion mutant.

Test Example 3 Measurement of Growth Inhibitory Activity Against HER2 Expressing Cell Line SK-BR-3 cells as a HER2 overexpressing human breast cancer cell line were suspended in a McCoy's 5a medium (manufactured by Life Technologies) supplemented with 10% fetal bovine serum. The cell suspension was seeded in each well of a 384-well flat-bottom microplate, and was then cultured in a 5% carbon dioxide gas-containing culture vessel at 37° C. for 1 day. Thereafter, the compound (I) obtained according to the method in Synthesis Example 1 was dissolved in DMSO, and the compound was diluted to 500 times the final concentration in DMSO. The compound in the DMSO solution was diluted with DMSO solution or the medium used in the suspension of the cells, and the obtained solution was then added to each well of the culture plate so that the final concentration of DMSO was 0.2%. The obtained mixture was further cultured in the 5% carbon dioxide gas-containing culture vessel at 37° C. for 3 days. After completion of the culture for 3 days in the presence of the compound, the cells were counted using CellTiter-Glo 2.0 (manufactured by Promega), and the growth inhibition percentage was then calculated according to the following equation. The concentration of the compound, in which the growth of the cells can be inhibited by 50%, was defined as IC50 (nM).

$$\text{Growth inhibitory percentage (\%)}=(C-T)/(C)\times 100$$

T: Emission intensity from the well to which the test compound was added

C: Emission intensity from the well to which the test compound was not added

The results are shown in the following Table 8.

Test Example 4 Measurement of Growth Inhibitory Activity Against HER2 Exon 20 Insertion Mutant Expressing Cell Line Growth inhibitory activity against the HER2 exon 20 insertion mutant was measured using Ba/F3 cells that were a mouse B lymphocyte precursor cell line, into which a human HER2 exon 20 insertion mutant gene had been introduced. The Ba/F3 cells were maintained in an RPMI-1640 medium (Thermo Fisher Scientific) supplemented with 10% fetal bovine serum (FBS), 100 U/mL penicillin, 100 μg/mL streptomycin (Thermo Fisher Scientific) and 1 ng/mL mouse interleukin-3 (mIL-3) (CST). Thereafter, a pCDNA3.1-hyg(+) vector, into which a human HER2 exon 20 insertion mutant gene (A775_G776insYVMA (HER2ex20insYVMA)), Internal Ribosome Binding Sequence (IRES), and a Kusabira orange gene had been incorporated, was introduced into the Ba/F3 cells according to an electroporation method using Amaxa (registered trademark) Cell Line Nucleofector (registered trademark) Kit V. The Ba/F3 cells expressing the HER2 exon 20 insertion mutant (Ba/F3-HER2insYVMA), which were selected with hygromycin B (Nacalai Tesque), exhibited mIL-3-independent growth.

Upon evaluation of cell growth inhibitory activity, the Ba/F3-HER2insYVMA cells were suspended in an RPMI-1640 medium supplemented with 10% FBS, 100 U/mL penicillin, and 100 μg/mL streptomycin. The cell suspension was seeded in each well of a 96-well flat-bottom microplate, and was then cultured in a 5% carbon dioxide gas-containing culture vessel at 37° C. for 1 day. The compound (I) obtained according to the method in Synthesis Example 1 was dissolved in DMSO, and was then diluted with DMSO or the medium used in the suspension of the cells. The obtained solution was then added to each well of the culture plate, so that the final concentration of DMSO became 0.2%. The obtained mixture was further cultured in the 5% carbon dioxide gas-containing culture vessel at 37° C. for 3 days. After completion of the culture for 3 days in the presence of the compound, the cells were counted using CellTiter-Glo 2.0 (manufactured by Promega), and the growth inhibition percentage was then calculated according to the following equation. The concentration of the compound, in which the growth of the cells can be inhibited by 50%, was defined as IC50 (nM).

$$\text{Growth inhibitory percentage (\%)}=(C-T)/(C)\times 100$$

T: Emission intensity from the well to which the test compound was added

C: Emission intensity from the well to which the test compound was not added

The results are shown in the following Table 8.

TABLE 8

| SK-BR-3 cell growth inhibitory activity IC50 value (nM) | HER2ex20insYVMA cell growth inhibitory activity IC50 value (nM) |
|---|---|
| 6.6 | 29 |

From the above results, it was found that the compound (I) has excellent cell growth inhibitory activity even against the HER2 expressing cell line (SK-BR-3) and also, against the HER2 exon 20 insertion mutant expressing cell line (Ba/F3-HER2insYVMA).

Test Example 5 Measurement of Growth Inhibitory Activity Against HER2 Expressing Cell Line (NCI-N87)

NCI-N87 cells as a HER2 overexpressing human stomach cancer cell line (American Type Culture Collection, Cat No. ATCC (registered trademark) CRL-5822) were suspended in an RPMI1640 medium (Wako Pure Chemical Industries, Ltd.) supplemented with 10% fetal bovine serum. Subsequently, the cell suspension was seeded in each well of a 96-well flat-bottom microplate, and was then cultured in a 5% carbon dioxide gas-containing culture vessel at 37° C. for 1 day. Thereafter, the compound (I) obtained according to the method in Synthesis Example 1 was dissolved in DMSO, and the compound was diluted to 1000 times the final concentration in DMSO. The compound (I) in the DMSO solution was diluted with the medium used in the suspension of the cells, and the obtained solution was then added to each well of the culture plate, so that the final concentration of DMSO became 0.1%. Regarding a control well, DMSO was diluted with the medium used in the suspension of the cells, and the obtained solution was then added to each well of the culture plate, so that the final concentration of DMSO became 0.1%. After addition of a drug solution, the obtained mixture was further cultured in the 5% carbon dioxide gas-containing culture vessel at 37° C. for 3 days. After completion of the culture for 3 days in the presence of the compound, the cells were counted using CellTiter-Glo 2.0 (manufactured by Promega) in accordance with the protocols recommended by Promega. The growth inhibition percentage was calculated according to the following equation. The concentration of the compound, in which the growth of the cells can be inhibited by 50%, was defined as IC50 (nM).

$$\text{Growth inhibitory percentage (\%)}=(C-T)/(C)\times 100$$

T: Emission intensity from the well to which the test compound was added

C: Emission intensity from the well to which the test compound was not added

The results are shown in the following Table 9.

TABLE 9

| NCI-N87 cell growth inhibitory activity IC50 value (nM) |
|---|
| 9.9 |

From the above results, it was found that the compound (I) has excellent cell growth inhibitory activity even against the HER2 overexpressing cell line (NCI-N87).

Test Example 6 Evaluation of Oral Absorbability

The compound (I) obtained according to the method in Synthesis Example 1 was suspended or dissolved in 0.5% HPMC aqueous solution and 0.1 N hydrochloric acid, and the obtained suspension or solution was orally administered to BALB/cA mice (CLEA Japan, Inc.) at a dose of 50 mg/kg/day. At 0.5, 1, 2, 4 and 6 hours after completion of the oral administration, blood was collected from the facial vein over time, so as to obtain plasma. The concentration of the compound in the obtained plasma was measured by LC-MS/MS, and the oral absorbability of the present compound was evaluated.

The results are shown in the following Table 10.

TABLE 10

| AUC 0-6 hr (μM · hr) |
|---|
| 31 |

From the above results, it was found that the compound of the present invention was contained in a sufficient concentration in the plasma, so that the compound (I) exhibited favorable oral absorbability.

Test Example 7 Evaluation of Brain Penetration Properties

The compound (I) obtained according to the method in Synthesis Example 1 was suspended or dissolved in 0.5% HPMC aqueous solution and 0.1 N hydrochloric acid, and the obtained suspension or solution was orally administered to BALB/cA mice (CLEA Japan, Inc.) at a dose of 50 mg/kg/day. At 0.5 hours after completion of the oral administration, blood was collected from the facial vein, and whole brain was then excised, so as to obtain plasma and brain samples. Water was added to the obtained brain sample in 3 times the volume of the brain sample, and the resultant was then homogenized using an ultrasonic homogenizer, so as to obtain a brain homogenate. The concentration of the compound in the obtained plasma and brain homogenate was measured by LC-MS/MS, and the brain penetration properties of the present compound were evaluated from the brain/plasma concentration of the compound.

The results are shown in the following Table 11.

TABLE 11

| Compound concentration in plasma (μM) | Compound concentration in brain (μM) | Kp value (Compound concentration in brain/plasma) |
|---|---|---|
| 12 | 2.7 | 0.23 |

From the above results, it was found that the compound (I) exhibited favorable brain penetration properties.

Test Example 8 Antitumor Effect Confirmation Test (In Vivo) on Direct Brain Transplantation Models, into which Luciferase Gene-Introduced HER2 Expressing Cell Line (NCI-N87-Luc) is Directly Transplanted In order to confirm the antitumor effects of a test compound on direct brain transplantation models, NCI-N87-Luc, which was obtained by introducing a luciferase gene into NCI-N87 that was a human stomach cancer tumor cell line purchased from American Type Culture Collection, was used. The NCI-N87-Luc was added into a 10% fetal bovine serum (FBS)-containing RPMI-1640 medium (supplemented with 4.5 g/L glucose, 10 mM HEPES, and 1 mM sodium pyruvate) (Wako Pure Chemical Industries, Ltd.), and this cell line was then cultured in a 5% CO2 incubator at 37° C.

The NCI-N87-Luc cells were re-suspended in PBS in a concentration of $6.25\times10^7$ cells/mL.

Using a mouse ear bar, a nude mouse with 6 to 7 weeks old (BALB/cAJcl-nu/nu, CLEA Japan, Inc.) was fixed in a brain stereotaxic apparatus, and the skin on the upper brain portion was disinfected with alcohol cotton and was then excised with a surgical knife.

A microdrill was used to drill a hole in the skull, and then, using a needle, a manipulator, and a syringe pump, 4 μL of the cell suspension was transplanted into the brain at a rate of 0.8 L/min.

As a reference of the amount of brain tumor, approximately 3 weeks after the transplantation, Total Flux (Photon/sec) was measured in all of the survival cases, using IVIS (PerkinElmer, Inc., model: Lumina II). Based on the obtained results, 6 animals were assigned to each group, using the grouping program of MiSTAT (Ver. 2.00).

The test compound was orally administered to the mice once a day, every day, for 21 days from the following day of the grouping (Days 1-21).

For judgment of the presence or absence of effects, the value (Log 10) obtained by logarithmic transformation of the total flux on the judgment date was used. The compound (I) obtained according to the method in Synthesis Example 1 as a test compound was administered to the mice at a dose of 25 mg/kg/day.

A graph was prepared with the value obtained by logarithmic transformation (Log 10) of the average total flux as a vertical axis, and with the number of days (Day) after the transplantation as a horizontal axis. The transition of the total flux over time in the drug administration period was observed.

As a control, 0.1 N HCl and 0.5% HPMC aqueous solution were used.

The results are shown in the following FIG. 31 and FIG. 32. The value obtained by logarithmic transformation (Log 10) of the total flux on Day 22 in each group was analyzed by a significance test. As a result, it was demonstrated that the aforementioned value of the compound was statistically significantly lower than the value of the control group (significance level (both sides): 5%). For the measurement of the body weight, an animal electronic balance was used. A body weight change percentage (Body weight change; BWCn) from the body weight on the $n^{th}$ day (BWn) was calculated according to the following equation:

BWCn (%)=[(body weight on $n^{th}$ day)−(body weight on grouping day)]/[(body weight on grouping day)]×100.

From the results of this test, it was found that the compound (I) has excellent antitumor effects against the HER2 overexpressing cell line (NCI-N87-luc) transplanted into the nude mice. Moreover, a body weight reduction of −20% or more was not observed in all of the mice had been administered. Accordingly, it was found that there were no serious side effects.

Test Example 9

Solid Stability Test

The free-form type II crystals of the compound (I) and type II crystals thereof with 1 equivalent of fumaric acid obtained in the Examples and Comparative Examples were evaluated for solid stability after storage for 4 weeks.

Storage condition: 60° C. (closed system)

Storage period: 4 weeks

Stored amount: Approximately 30 mg

Storage container: Glass bottle

The results are shown in the following Table 12.

TABLE 12

| | Free-form type II crystal | Type II crystal with 1 equivalent of fumaric acid |
|---|---|---|
| Chemical purity before storage (%) | 99.87 | 99.85 |
| Chemical purity after storage (%) | 99.88 | 99.85 |
| Amount of related substances before storage (%) | 0.13 | 0.15 |
| Amount of related substances after storage (%) | 0.12 | 0.15 |

Approximately 1 mg of a sample was weighed, dissolved in approximately 1 mL of a liquid mixture of water/acetonitrile (1:1), and 5 μL of this solution was accurately measured. Changes in the amount of related substances (the amount of substances detected other compound (I)) were analyzed by HPLC by the following method.

Hplc Analysis Method (Stability Test)

The amount of related substances in the sample solution was measured by HPLC analysis. Handling of the apparatuses, including data processing, was in accordance with the methods and procedures instructed for each apparatus.

Column: XSelect CSH C18 (4.6×150 mm, 3.5 μm) manufactured by Waters

UV detection: 246 nm

Column temperature: 40° C.

Flow rate: 1.0 mL/min

Sample cooler: 5° C.

Sample concentration: 1 mg/mL

Mobile phase A: Liquid mixture of 5 mmol/L ammonium formate buffer (pH 6.5)/acetonitrile (9:1)

Mobile phase B: Acetonitrile

The gradients are shown in Table 13.

TABLE 13

| Time (min) | Mobile phase A (vol %) | Mobile phase B (vol %) |
|---|---|---|
| 0-31 | 90→30 | 10→70 |
| 31-36 | 30 | 70 |
| 36-37 | 30→90 | 70→10 |

As a result, no change in the powder X-ray diffraction pattern was observed in either the free-form type II crystal of compound (I) or the type II crystal of the same with 1 equivalent of fumaric acid, and almost no increase in related substances was observed. They were found to be extremely stable crystals.

Test Example 10

Dynamic Vapor Sorption (DVS) Test

Dynamic vapor sorption tests were conducted using a type II crystal of compound (I) with1 equivalent of fumaric acid, a free-form type II crystal of the same, a free-form type I crystal of the same, a type V crystal of the same with 1 equivalent of fumaric acid, and a crystal of the same with 1 equivalent of L-tartaric acid obtained in the Examples and Reference Examples.

The dynamic vapor sorption test was conducted for measurement according to the following conditions.

Approximately 10 mg of each sample was packed in a dedicated quartz holder, and the weight of the sample at each humidity was continuously measured and recorded under the following conditions. Handling of the apparatuses, including data processing, was in accordance with the methods and procedures instructed for each apparatus.

Apparatus: VTI SA+ (manufactured by TA Instruments)

Drying temperature: 60° C.

Temperature increase rate: 1° C./min

Equilibrium of drying: It was confirmed that a decrease by 0.01 wt % in 5 minutes did not occur within the range not exceeding 300 minutes.

Measurement temperature: 25° C.

Equilibrium of humidification: It was confirmed that an increase by 0.01 wt % in 5 minutes did not occur within the range not exceeding 120 minutes.

Relative humidity program: Increase by 5% RH from 5% RH to 95% RH and decrease by 5% RH from 95% RH to 5% RH The weight changes in the range of measurement conditions obtained in these tests are shown in Tables 14 to 18.

TABLE 14

Results of dynamic vapor sorption test of type II crystal of compound (I) with 1 equivalent of fumaric acid

| Relative humidity (%) | Weight change rate (%) Adsorption | Desorption |
|---|---|---|
| 5 | 0.01 | 0.04 |
| 20 | 0.11 | 0.13 |
| 40 | 0.18 | 0.20 |
| 60 | 0.27 | 0.30 |
| 80 | 0.34 | 0.34 |
| 95 | 0.38 | 0.38 |

TABLE 15

Results of dynamic vapor sorption test of free-form type II crystal of compound (I)

| Relative humidity (%) | Weight change rate (%) Adsorption | Desorption |
|---|---|---|
| 5 | 0.01 | 0.01 |
| 20 | 0.02 | 0.03 |
| 40 | 0.05 | 0.06 |
| 60 | 0.08 | 0.08 |
| 80 | 0.10 | 0.11 |
| 95 | 0.12 | 0.12 |

TABLE 16

Results of dynamic vapor sorption test of free-form type I crystal of compound (I)

| Relative humidity (%) | Weight change rate (%) Adsorption | Desorption |
|---|---|---|
| 5 | 0.01 | 0.01 |
| 20 | 0.04 | 0.04 |
| 40 | 0.10 | 0.13 |
| 60 | 0.26 | 0.60 |
| 80 | 0.50 | 0.69 |
| 95 | 0.72 | 0.72 |

TABLE 17

Results of dynamic vapor sorption test of type V crystal of compound (I) with 1 equivalent of fumaric acid

| Relative humidity (%) | Weight change rate (%) Adsorption | Desorption |
|---|---|---|
| 5 | 0.01 | 0.06 |
| 20 | 0.11 | 0.16 |
| 40 | 0.21 | 0.27 |
| 60 | 0.33 | 0.39 |
| 80 | 0.47 | 0.51 |
| 95 | 0.59 | 0.59 |

TABLE 18

Results of dynamic vapor sorption test of crystal of compound (I) with 1 equivalent of L-tartaric acid

| Relative humidity (%) | Weight change rate (%) Adsorption | Desorption |
|---|---|---|
| 5 | 0.50 | 0.54 |
| 20 | 1.05 | 1.16 |
| 40 | 1.60 | 1.67 |
| 60 | 2.16 | 2.38 |
| 80 | 3.26 | 3.64 |
| 95 | 6.41 | 6.41 |

As shown in Table 14, the type II crystal of compound (I) with 1 equivalent of fumaric acid had a weight increase of 0.38% in a dynamic vapor sorption test under 95% relative humidity, which was less than 1%. The crystal was determined to be almost non-hygroscopic. Similarly, the free-form type II crystal of compound (I), the free-form type I crystal of the same, and the type V crystal of the same with 1 equivalent of fumaric acid also had a mass increase of less than 1% in a dynamic vapor sorption test under 95% relative humidity, which was less than 1%. The crystals were determined to be almost non-hygroscopic (Tables 15 to 17). Meanwhile, as shown in Table 18, the crystal of compound (I) with 1 equivalent of L-tartaric acid had a mass increase of as high as 6.41% in a dynamic vapor sorption test under 95% relative humidity, which was less than 1%. The crystal was determined to be highly hygroscopic.

Therefore, since the type II crystal of compound (I) with 1 equivalent of fumaric acid, the free-form type II crystal of the same, the free-form type I crystal of the same, and the type V crystal with 1 equivalent of fumaric acid are less hygroscopic than the crystal of compound (I) with 1 equivalent of L-tartaric acid, they are considered to be excellent candidate compounds for drug development in terms of industrial manufacturing of pharmaceutical products with stable quality. The type II crystal of compound (I) with 1 equivalent of fumaric acid, the free-form type II crystal of the same, the free-form type I crystal of the same, and the type V crystal of the same with 1 equivalent of fumaric acid were confirmed to have excellent properties as pharmaceutical products or active pharmaceutical ingredients.

Test Example 11

Blood Concentration Measurement Test

Blood concentration measurement tests were conducted for the type I crystal of compound (I), the type II crystal of compound (I), and the type II crystal of compound (I) with 1 equivalent of fumarate obtained in the Examples. Specifically, 0.5% HPMC containing 0.1N hydrochloric acid was used for the type I crystal of compound (I) and 0.5% HPMC was used for the type II crystal of compound (I) and the type II crystal of compound (I) with 1 equivalent of fumaric acid to convert each crystal into the compound (I) (free-form) in terms of molecular weight so as to prepare suspensions of 100 mg/10 mL and 300 mg/10 mL. These administration solutions were orally administered to female rats (Crl:CD (SD), Charles River Laboratories Japan, Inc.) kept under feeding conditions at a volume of 10 mL/kg body weight using an oral administration sonde. After administration, the rats were returned to the rat cage and their conditions were checked. Water and feeding were freely available in the cage. At 0.5, 1, 2, 4, and 6 hours after administration, the rats were anesthetized with isoflurane, and approximately 80 μL of blood was collected from the jugular vein using a heparin-coated syringe and an injection needle (25 G).

The collected blood was ice-cooled and plasma was separated by centrifugation. After the blood collection was completed, the rats were returned to the rat cage and the state after awakening of anesthesia was checked. After the final blood collection, the depth of isoflurane anesthesia was checked. Then, the limbs were fixed in a supine position with a small animal experiment holding apparatus, and the abdomen was opened such that each rat was euthanized by exsanguination through an incision in the abdominal aorta and vena cava.

AUC0-6 hr (Area under the blood concentration-time curve for 0 to 6 hours after administration calculated by the trapezoidal method), Cmax (maximum blood concentration), and Tmax (time to reach maximum blood concentration) were calculated from the concentration of the compound (I) in each plasma measured by the MRM method using LC/MS/MS and quantified from the calibration curve using Phoenix WinNonlin (v6.4.0,Certara USA, Inc.).

The results are shown in Table 19. When the dose was increased from 100 mg/kg to 300 mg/kg, for the type I crystal of compound (I) with hydrochloric acid and the type II crystal of compound (I), Cmax increased 0.8 times and 1.2 times, respectively, and AUC 0-6 hr increased 1.0 times and 1.5 times, respectively. Meanwhile, for the type II crystal of compound (I) with 1 equivalent of fumaric acid, each of $C_{max}$ and AUC0-6 hr increased 1.9 times. In addition, at a dose of 300 mg/kg, $C_{max}$ of the type II crystal of compound (I) with 1 equivalent of fumaric acid was 1.7 times the value of the type I crystal of compound (I) with the acid and 1.4 times the value of the type II crystal of compound (I), and $AUC_{0\text{-}6\ hr}$ of the type II crystal of compound (I) with 1 equivalent of fumaric acid was 2.4 times the values of the type I crystal of compound (I) with the acid and the type II crystal of compound (I). Therefore, the type II crystal of compound (I) with 1 equivalent of fumaric acid according to the present invention was confirmed to show more favorable oral absorbability.

TABLE 19

| | | Oral administration | | |
|---|---|---|---|---|
| Dose | Parameter | Type I crystal of compound (I) (with hydrochloric acid) | Type II crystal of compound (I) | Type II crystal of compound (I) with 1 equivalent of fumaric acid |
| 100 mg/kg | $AUC_{0\text{-}6hr}$ (μM · hr) | 7.42 | 5.79 | 6.14 |
| | $C_{max}$ (μM) | 2.67 | 1.88 | 2.74 |
| | $T_{max}$ (hr) | 0.75 | 1.50 | 1.25 |
| 300 mg/kg | $AUC_{0\text{-}6hr}$ (μM · hr) | 7.11 | 8.53 | 11.9 |
| | $C_{max}$ (μM) | 2.25 | 2.25 | 5.34 |
| | $T_{max}$ (hr) | 3.25 | 3.33 | 0.5 |

It is to be noted that all documents and publications cited in the present description are incorporated herein by reference in their entirety, regardless of the purpose thereof. Moreover, the present description includes the contents disclosed in the claims, specification and drawings of Japanese Patent Application No. 2020-121520 (filed on Jul. 15, 2020), from which the present application claims priority.

Several embodiments of the present invention are described above. However, these embodiments are provided for illustrative purpose only, and thus, are not intended to limit the scope of the present invention. These novel embodiments can be carried out in various other forms, and various abbreviations, substitutions and alternations can be carried out, unless they are deviated from the spirit of the invention. These embodiments and the modifications thereof are included in the scope or spirit of the invention, and are also included in the invention according to the claims and the scope equivalent thereto.

The invention claimed is:

1. A crystal having peaks at three or more diffraction angles (2θ±0.2°) selected from 5.5°, 6.8°, 9.3°, 13.4°, 15.3°, 16.3°, 18.5°, 19.8°, 22.0°, and 24.5° in a powder X-ray diffraction spectrum, which is a type II crystal of 7-((3R, 5S)-1-acryloyl-5-methylpyrrolidin-3-yl)-4-amino-6-(cyclopropylethynyl)-N—((R)-1-phenylethyl)-7H-pyrrolo[2,3-d] pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2,3-d] pyrimidine-5-carboxamide to fumaric acid is 1:1.

2. The crystal according to claim 1, which has peaks at diffraction angles (2θ±0.2°) of 5.5°, 6.8°, 9.3°, 13.4°, 15.3°, 16.3°, 18.5°, 19.8°, 22.0°, and 24.5° in a powder X-ray diffraction spectrum.

3. The crystal according to claim 1, which has an endothermic peak determined by simultaneous thermogravimetry-differential thermal analysis at around 178° C.

4. A crystal having peaks at three or more diffraction angles (2θ±0.2°) selected from 8.3°, 14.8°, 17.3°, 18.0°, 19.1°, 20.3°, 21.0°, 22.5°, 23.0°, and 26.2° in a powder X-ray diffraction spectrum, which is a type II crystal of 7-((3R,5S)-1-acryloyl-5-methylpyrrolidin-3-yl)-4-amino-6-(cyclopropylethynyl)-N—((R)-1-phenylethyl)-7H-pyrrolo [2,3-d]pyrimidine-5-carboxamide.

5. The crystal according to claim 4, which has peaks at diffraction angles (2θ±0.2°) of 8.3°, 14.8°, 17.3°, 18.0°, 19.1°, 20.3°, 21.0°, 22.5°, 23.0°, and 26.2° in a powder X-ray diffraction spectrum.

6. The crystal according to claim 4, which has an endothermic peak determined by simultaneous thermogravimetry-differential thermal analysis at around 182° C.

7. A crystal having peaks at three or more diffraction angles (2θ±0.2°) selected from 9.9°, 11.7°, 13.2°, 17.7°, 18.1°, 18.8°, and 20.8° in a powder X-ray diffraction spectrum, which is a type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide.

8. The crystal according to claim 7, which has peaks at diffraction angles (2θ±0.2°) of 9.9°, 11.7°, 13.2°, 17.7°, 18.1°, 18.8°, and 20.8° in a powder X-ray diffraction spectrum.

9. The crystal according to claim 7, which has an endothermic peak determined by simultaneous thermogravimetry-differential thermal analysis at around 183° C.

10. A crystal having peaks at four or more diffraction angles (2θ±0.2°) selected from 6.9°, 9.4°, 10.2°, 13.7°, 21.1°, 23.6°, and 26.5° in a powder X-ray diffraction spectrum, which is a type V crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2, 3-d]pyrimidine-5-carboxamide to fumaric acid is 1:1.

11. The crystal according to claim 10, which has peaks at diffraction angles (2θ±0.2°) of 6.9°, 9.4°, 10.2°, 13.7°, 21.1°, 23.6°, and 26.5° in a powder X-ray diffraction spectrum.

12. The crystal according to claim 10, which has an endothermic peak determined by simultaneous thermogravimetry-differential thermal analysis at around 151° C.

13. A crystal having peaks at four or more diffraction angles (2θ±0.2°) selected from 6.4°, 10.3°, 12.8°, 15.0°, 20.7°, 23.4°, and 26.6° in a powder X-ray diffraction spectrum, which is a type I crystal of 7-((3R,5S)-1-acryloyl-5-methylpyrrolidin-3-yl)-4-amino-6-(cyclopropylethynyl)-N—((R)-1-phenylethyl)-7H-pyrrolo[2,3-d]pyrimidine-5-carboxamide with fumaric acid, wherein a molar ratio of 7-((3R,5S)-1-acryloyl-5-methylpyrrolidin-3-yl)-4-amino-6-(cyclopropylethynyl)-N—((R)-1-phenylethyl)-7H-pyrrolo2, 3-d]pyrimidine-5-carboxamide to fumaric acid is 1:1.

14. The crystal according to claim 13, which has peaks at diffraction angles (2θ±0.2°) of 6.4°, 10.3°, 12.8°, 15.0°, 20.7°, 23.4°, and 26.6° in a powder X-ray diffraction spectrum.

15. The crystal according to claim 13, which has an endothermic peak determined by simultaneous thermogravimetry-differential thermal analysis at around 153° C.

16. A pharmaceutical composition, comprising the crystal according to claim 1.

17. A pharmaceutical composition for oral administration, comprising the crystal according to claim 1.

18. An antitumor agent, comprising the crystal according to claim 1.

* * * * *

SEQUENCE LISTING

```
<160> NUMBER OF SEQ ID NOS: 6

<210> SEQ ID NO 1
<211> LENGTH: 4664
<212> TYPE: DNA
<213> ORGANISM: Homo sapiens

<400> SEQUENCE: 1

gcttgctccc aatcacagga gaaggaggag gtggaggagg agggctgctt gaggaagtat      60

aagaatgaag ttgtgaagct gagattcccc tccattggga ccggagaaac caggggagcc     120

ccccgggcag ccgcgcgccc cttcccacgg ggccctttac tgcgccgcgc gcccggcccc     180

cacccctcgc agcaccccgc gccccgcgcc ctcccagccg ggtccagccg gagccatggg     240

gccggagccg cagtgagcac catggagctg gcggccttgt gccgctgggg gctcctcctc     300

gccctcttgc cccccggagc cgcgagcacc caagtgtgca ccggcacaga catgaagctg     360

cggctccctg ccagtcccga gacccacctg gacatgctcc gccacctcta ccagggctgc     420

caggtggtgc agggaaacct ggaactcacc tacctgccca ccaatgccag cctgtccttc     480

ctgcaggata tccaggaggt gcagggctac gtgctcatcg ctcacaacca agtgaggcag     540

gtcccactgc agaggctgcg gattgtgcga ggcacccagc tctttgagga caactatgcc     600

ctggccgtgc tagacaatgg agacccgctg aacaatacca cccctgtcac aggggcctcc     660
```

-continued

```
ccaggaggcc tgcgggagct gcagcttcga agcctcacag agatcttgaa aggaggggtc    720
ttgatccagc ggaaccccca gctctgctac caggacacga ttttgtggaa ggacatcttc    780
cacaagaaca accagctggc tctcacactg atagacacca accgctctcg ggcctgccac    840
ccctgttctc cgatgtgtaa gggctcccgc tgctggggag agagttctga ggattgtcag    900
agcctgacgc gcactgtctg tgccggtggc tgtgcccgct gcaaggggcc actgcccact    960
gactgctgcc atgagcagtg tgctgccggc tgcacgggcc ccaagcactc tgactgcctg   1020
gcctgcctcc acttcaacca cagtggcatc tgtgagctgc actgcccagc cctggtcacc   1080
tacaacacag acacgtttga gtccatgccc aatcccgagg gccggtatac attcggcgcc   1140
agctgtgtga ctgcctgtcc ctacaactac ctttctacgg acgtgggatc ctgcaccctc   1200
gtctgccccc tgcacaacca agaggtgaca gcagaggatg gaacacagcg gtgtgagaag   1260
tgcagcaagc cctgtgcccg agtgtgctat ggtctgggca tggagcactt gcgagaggtg   1320
agggcagtta ccagtgccaa tatccaggag tttgctggct gcaagaagat ctttgggagc   1380
ctggcatttc tgccggagag ctttgatggg gacccagcct ccaacactgc cccgctccag   1440
ccagagcagc tccaagtgtt tgagactctg gaagagatca caggttacct atacatctca   1500
gcatggccgg acagcctgcc tgacctcagc gtcttccaga acctgcaagt aatccgggga   1560
cgaattctgc acaatggcgc ctactcgctg accctgcaag ggctgggcat cagctggctg   1620
gggctgcgct cactgaggga actgggcagt ggactggccc tcatccacca taacacccac   1680
ctctgcttcg tgcacacggt gccctgggac cagctctttc ggaacccgca ccaagctctg   1740
ctccacactg ccaaccggcc agaggacgag tgtgtgggcg agggcctggc ctgccaccag   1800
ctgtgcgccc gagggcactg ctggggtcca gggcccaccc agtgtgtcaa ctgcagccag   1860
ttccttcggg gccaggagtg cgtggaggaa tgccgagtac tgcaggggct ccccagggag   1920
tatgtgaatg ccaggcactg tttgccgtgc caccctgagt gtcagcccca gaatggctca   1980
gtgacctgtt ttggaccgga ggctgaccag tgtgtggcct gtgcccacta taaggaccct   2040
cccttctgcg tggcccgctg ccccagcggt gtgaaacctg acctctccta catgcccatc   2100
tggaagtttc cagatgagga gggcgcatgc cagccttgcc ccatcaactg cacccactcc   2160
tgtgtggacc tggatgacaa gggctgcccc gccgagcaga gagccagccc tctgacgtcc   2220
atcatctctg cggtggttgg cattctgctg gtcgtggtct tgggggtggt ctttgggatc   2280
ctcatcaagc gacggcagca gaagatccgg aagtacacga tgcggagact gctgcaggaa   2340
acggagctgg tggagccgct gacacctagc ggagcgatgc ccaaccaggc gcagatgcgg   2400
atcctgaaag agacggagct gaggaaggtg aaggtgcttg gatctggcgc ttttggcaca   2460
gtctacaagg gcatctggat ccctgatggg gagaatgtga aaattccagt ggccatcaaa   2520
gtgttgaggg aaaacacatc ccccaaagcc aacaaagaaa tcttagacga agcatacgtg   2580
atggctggtg tgggctcccc atatgtctcc cgccttctgg gcatctgcct gacatccacg   2640
gtgcagctgg tgacacagct tatgccctat ggctgcctct tagaccatgt ccgggaaaac   2700
cgcggacgcc tgggctccca ggacctgctg aactggtgta tgcagattgc caaggggatg   2760
agctacctgg aggatgtgcg gctcgtacac agggacttgg ccgctcggaa cgtgctggtc   2820
aagagtccca accatgtcaa aattacagac ttcgggctgg ctcggctgct ggacattgac   2880
gagacagagt accatgcaga tgggggcaag gtgcccatca agtggatggc gctggagtcc   2940
attctccgcc ggcggttcac ccaccagagt gatgtgtgga gttatggtgt gactgtgtgg   3000
```

-continued

```
gagctgatga cttttggggc caaaccttac gatgggatcc cagcccggga gatccctgac   3060

ctgctggaaa agggggagcg gctgccccag cccccccatct gcaccattga tgtctacatg   3120

atcatggtca aatgttggat gattgactct gaatgtcggc caagattccg ggagttggtg   3180

tctgaattct cccgcatggc cagggacccc cagcgctttg tggtcatcca gaatgaggac   3240

ttgggcccag ccagtccctt ggacagcacc ttctaccgct cactgctgga ggacgatgac   3300

atgggggacc tggtggatgc tgaggagtat ctggtacccc agcagggctt cttctgtcca   3360

gaccctgccc cgggcgctgg gggcatggtc caccacaggc accgcagctc atctaccagg   3420

agtggcggtg gggacctgac actagggctg gagccctctg aagaggaggc ccccaggtct   3480

ccactggcac cctccgaagg ggctggctcc gatgtatttg atggtgacct gggaatgggg   3540

gcagccaagg ggctgcaaag cctcccccaca catgacccca gccctctaca gcggtacagt   3600

gaggacccca cagtacccct gccctctgag actgatggct acgttgcccc cctgacctgc   3660

agcccccagc ctgaatatgt gaaccagcca gatgttcggc cccagccccc ttcgccccga   3720

gagggccctc tgcctgctgc ccgacctgct ggtgccactc tggaaaggcc caagactctc   3780

tccccaggga agaatggggt cgtcaaagac gtttttgcct ttgggggtgc cgtggagaac   3840

cccgagtact tgacacccca gggaggagct gcccctcagc ccccaccctcc tcctgccttc   3900

agcccagcct tcgacaacct ctattactgg gaccaggacc caccagagcg gggggctcca   3960

cccagcacct tcaaagggac acctacggca gagaacccag agtacctggg tctggacgtg   4020

ccagtgtgaa ccagaaggcc aagtccgcag aagccctgat gtgtcctcag ggagcaggga   4080

aggcctgact tctgctggca tcaagaggtg ggagggccct ccgaccactt ccaggggaac   4140

ctgccatgcc aggaacctgt cctaaggaac cttccttcct gcttgagttc ccagatggct   4200

ggaaggggtc cagcctcgtt ggaagaggaa cagcactggg gagtctttgt ggattctgag   4260

gccctgccca atgagactct agggtccagt ggatgccaca gcccagcttg gccctttcct   4320

tccagatcct gggtactgaa agccttaggg aagctggcct gagaggggaa gcggccctaa   4380

gggagtgtct aagaacaaaa gcgacccatt cagagactgt ccctgaaacc tagtactgcc   4440

ccccatgagg aaggaacagc aatggtgtca gtatccaggc tttgtacaga gtgcttttct   4500

gtttagtttt tacttttttt gttttgtttt tttaaagatg aaataaagac ccagggggag   4560

aatgggtgtt gtatggggag gcaagtgtgg ggggtccttc tccacaccca ctttgtccat   4620

ttgcaaatat attttggaaa acagctaaaa aaaaaaaaaa aaaa                    4664
```

<210> SEQ ID NO 2
<211> LENGTH: 1255
<212> TYPE: PRT
<213> ORGANISM: Homo sapiens

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80
```

-continued

```
Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
```

-continued

```
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925
```

```
Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His His  Arg His Arg Ser Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro Leu  Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val Pro Val
    1250                1255


<210> SEQ ID NO 3
<211> LENGTH: 4940
<212> TYPE: DNA
<213> ORGANISM: Homo sapiens

<400> SEQUENCE: 3

aagttcctgt gttctttatt ctactctccg ctgaagtcca cacagtttaa attaaagttc     60

ccggattttt gtgggcgcct gccccgcccc tcgtcccccct gctgtgtcca tatatcgagg    120
```

-continued

```
cgatagggtt aagggaaggc ggacgcctga tgggttaatg agcaaactga agtgttttcc    180
atgatctttt ttgagtcgca attgaagtac cacctcccga gggtgattgc ttccccatgc    240
ggggtagaac ctttgctgtc ctgttcacca ctctacctcc agcacagaat ttggcttatg    300
cctactcaat gtgaagatga tgaggatgaa aacctttgtg atgatccact tccacttaat    360
gaatggtggc aaagcaaagc tatattcaag accacatgca aagctactcc ctgagcaaag    420
agtcacagat aaaacggggg caccagtaga atggccagga caaacgcagt gcagcacaga    480
gactcagacc ctggcagcca tgcctgcgca ggcagtgatg agagtgacat gtactgttgt    540
ggacatgcac aaaagtgaga tacttcaaag attccagaag atatgccccg ggggtcctgg    600
aagccacaag tgtgcaccgg cacagacatg aagctgcggc tccctgccag tcccgagacc    660
cacctggaca tgctccgcca cctctaccag ggctgccagg tggtgcaggg aaacctggaa    720
ctcacctacc tgcccaccaa tgccagcctg tccttcctgc aggatatcca ggaggtgcag    780
ggctacgtgc tcatcgctca caaccaagtg aggcaggtcc cactgcagag gctgcggatt    840
gtgcgaggca cccagctctt tgaggacaac tatgccctgg ccgtgctaga caatggagac    900
ccgctgaaca ataccacccc tgtcacaggg gcctccccag gaggcctgcg ggagctgcag    960
cttcgaagcc tcacagagat cttgaaagga ggggtcttga tccagcggaa cccccagctc   1020
tgctaccagg acacgatttt gtggaaggac atcttccaca agaacaacca gctggctctc   1080
acactgatag acaccaaccg ctctcgggcc tgccacccct gttctccgat gtgtaagggc   1140
tcccgctgct ggggagagag ttctgaggat tgtcagagcc tgacgcgcac tgtctgtgcc   1200
ggtggctgtg cccgctgcaa ggggccactg cccactgact gctgccatga gcagtgtgct   1260
gccggctgca cgggccccaa gcactctgac tgcctggcct gcctccactt caaccacagt   1320
ggcatctgtg agctgcactg cccagccctg gtcacctaca acacagacac gtttgagtcc   1380
atgcccaatc ccgagggccg gtatacattc ggcgccagct gtgtgactgc ctgtccctac   1440
aactaccttt ctacggacgt gggatcctgc accctcgtct gcccccctgca caaccaagag   1500
gtgacagcag aggatggaac acagcggtgt gagaagtgca gcaagccctg tgcccgagtg   1560
tgctatggtc tgggcatgga gcacttgcga gaggtgaggg cagttaccag tgccaatatc   1620
caggagtttg ctggctgcaa gaagatcttt gggagcctgg catttctgcc ggagagcttt   1680
gatggggacc cagcctccaa cactgccccg ctccagccag agcagctcca agtgtttgag   1740
actctggaag agatcacagg ttacctatac atctcagcat ggccggacag cctgcctgac   1800
ctcagcgtct tccagaacct gcaagtaatc cggggacgaa ttctgcacaa tggcgcctac   1860
tcgctgaccc tgcaagggct gggcatcagc tggctggggc tgcgctcact gagggaactg   1920
ggcagtggac tggccctcat ccaccataac acccacctct gcttcgtgca cacggtgccc   1980
tgggaccagc tctttcggaa cccgcaccaa gctctgctcc acactgccaa ccggccagag   2040
gacgagtgtg tgggcgaggg cctggcctgc caccagctgt gcgcccgagg gcactgctgg   2100
ggtccagggc ccacccagtg tgtcaactgc agccagttcc ttcggggcca ggagtgcgtg   2160
gaggaatgcc gagtactgca ggggctcccc agggagtatg tgaatgccag gcactgtttg   2220
ccgtgccacc ctgagtgtca gccccagaat ggctcagtga cctgttttgg accggaggct   2280
gaccagtgtg tggcctgtgc ccactataag gaccctccct tctgcgtggc ccgctgcccc   2340
agcggtgtga aacctgacct ctcctacatg cccatctgga agtttccaga tgaggagggc   2400
gcatgccagc cttgccccat caactgcacc cactcctgtg tggacctgga tgacaagggc   2460
tgccccgccg agcagagagc cagccctctg acgtccatca tctctgcggt ggttggcatt   2520
```

-continued ctgctggtcg tggtcttggg ggtggtcttt gggatcctca tcaagcgacg gcagcagaag 2580
atccggaagt acacgatgcg gagactgctg caggaaacgg agctggtgga gccgctgaca 2640
cctagcggag cgatgcccaa ccaggcgcag atgcggatcc tgaaagagac ggagctgagg 2700
aaggtgaagg tgcttggatc tggcgctttt ggcacagtct acaagggcat ctggatccct 2760
gatggggaga atgtgaaaat tccagtggcc atcaaagtgt tgagggaaaa cacatccccc 2820
aaagccaaca aagaaatctt agacgaagca tacgtgatgg ctggtgtggg ctccccatat 2880
gtctcccgcc ttctgggcat ctgcctgaca tccacggtgc agctggtgac acagcttatg 2940
ccctatggct gcctcttaga ccatgtccgg gaaaaccgcg gacgcctggg ctcccaggac 3000
ctgctgaact ggtgtatgca gattgccaag ggatgagct acctggagga tgtgcggctc 3060
gtacacaggg acttggccgc tcggaacgtg ctggtcaaga gtcccaacca tgtcaaaatt 3120
acagacttcg ggctggctcg gctgctggac attgacgaga cagagtacca tgcagatggg 3180
ggcaaggtgc ccatcaagtg gatggcgctg gagtccattc tccgccggcg gttcacccac 3240
cagagtgatg tgtggagtta tggtgtgact gtgtgggagc tgatgacttt tggggccaaa 3300
ccttacgatg ggatcccagc ccgggagatc cctgacctgc tggaaaaggg ggagcggctg 3360
ccccagcccc ccatctgcac cattgatgtc tacatgatca tggtcaaatg ttggatgatt 3420
gactctgaat gtcggccaag attccgggag ttggtgtctg aattctcccg catggccagg 3480
gacccccagc gctttgtggt catccagaat gaggacttgg gcccagccag tcccttggac 3540
agcaccttct accgctcact gctggaggac gatgacatgg gggacctggt ggatgctgag 3600
gagtatctgg taccccagca gggcttcttc tgtccagacc ctgcccccggg cgctgggggc 3660
atggtccacc acaggcaccg cagctcatct accaggagtg gcggtgggga cctgacacta 3720
gggctggagc cctctgaaga ggaggccccc aggtctccac tggcaccctc cgaaggggct 3780
ggctccgatg tatttgatgg tgacctggga atgggggcag ccaaggggct gcaaagcctc 3840
cccacacatg accccagccc tctacagcgg tacagtgagg accccacagt acccctgccc 3900
tctgagactg atggctacgt tgcccccctg acctgcagcc cccagcctga atatgtgaac 3960
cagccagatg ttcggcccca gcccccttcg ccccgagagg gccctctgcc tgctgcccga 4020
cctgctggtg ccactctgga aaggcccaag actctctccc cagggaagaa tggggtcgtc 4080
aaagacgttt ttgcctttgg gggtgccgtg gagaaccccg agtacttgac accccaggga 4140
ggagctgccc ctcagcccca ccctcctcct gccttcagcc cagccttcga caacctctat 4200
tactgggacc aggacccacc agagcggggg gctccaccca gcaccttcaa agggacacct 4260
acggcagaga acccagagta cctgggtctg gacgtgccag tgtgaaccag aaggccaagt 4320
ccgcagaagc cctgatgtgt cctcagggag cagggaaggc ctgacttctg ctggcatcaa 4380
gaggtgggag ggccctccga ccacttccag gggaacctgc catgccagga acctgtccta 4440
aggaaccttc cttcctgctt gagttcccag atggctggaa ggggtccagc ctcgttggaa 4500
gaggaacagc actggggagt ctttgtggat tctgaggccc tgcccaatga gactctaggg 4560
tccagtggat gccacagccc agcttggccc tttccttcca gatcctgggt actgaaagcc 4620
ttagggaagc tggcctgaga ggggaagcgg ccctaaggga gtgtctaaga acaaaagcga 4680
cccattcaga gactgtccct gaaacctagt actgcccccc atgaggaagg aacagcaatg 4740
gtgtcagtat ccaggctttg tacagagtgc ttttctgttt agtttttact ttttttgttt 4800
tgttttttta aagatgaaat aaagacccag gggagaatg ggtgttgtat ggggaggcaa 4860

```
gtgtgggggg tccttctcca cacccacttt gtccatttgc aaatatattt tggaaaacag   4920

ctaaaaaaaa aaaaaaaaaa                                               4940
```

<210> SEQ ID NO 4
<211> LENGTH: 1240
<212> TYPE: PRT
<213> ORGANISM: Homo sapiens

<400> SEQUENCE: 4

```
Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
```

-continued

```
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
    690                 695                 700

Leu Arg Lys Val Lys Val Leu Gly Ser Gly Ala Phe Gly Thr Val Tyr
705                 710                 715                 720

Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
            740                 745                 750

Leu Asp Glu Ala Tyr Val Met Ala Gly Val Gly Ser Pro Tyr Val Ser
        755                 760                 765

Arg Leu Leu Gly Ile Cys Leu Thr Ser Thr Val Gln Leu Val Thr Gln
    770                 775                 780
```

-continued

```
Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
        835                 840                 845

Phe Gly Leu Ala Arg Leu Leu Asp Ile Asp Glu Thr Glu Tyr His Ala
    850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
        915                 920                 925

Pro Pro Ile Cys Thr Ile Asp Val Tyr Met Ile Met Val Lys Cys Trp
    930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly  Asp Leu Val Asp Ala  Glu Glu Tyr
        995                 1000                1005

Leu Val  Pro Gln Gln Gly Phe  Phe Cys Pro Asp Pro  Ala Pro Gly
    1010                1015                1020

Ala Gly  Gly Met Val His His  Arg His Arg Ser Ser  Ser Thr Arg
    1025                1030                1035

Ser Gly  Gly Gly Asp Leu Thr  Leu Gly Leu Glu Pro  Ser Glu Glu
    1040                1045                1050

Glu Ala  Pro Arg Ser Pro Leu  Ala Pro Ser Glu Gly  Ala Gly Ser
    1055                1060                1065

Asp Val  Phe Asp Gly Asp Leu  Gly Met Gly Ala Ala  Lys Gly Leu
    1070                1075                1080

Gln Ser  Leu Pro Thr His Asp  Pro Ser Pro Leu Gln  Arg Tyr Ser
    1085                1090                1095

Glu Asp  Pro Thr Val Pro Leu  Pro Ser Glu Thr Asp  Gly Tyr Val
    1100                1105                1110

Ala Pro  Leu Thr Cys Ser Pro  Gln Pro Glu Tyr Val  Asn Gln Pro
    1115                1120                1125

Asp Val  Arg Pro Gln Pro Pro  Ser Pro Arg Glu Gly  Pro Leu Pro
    1130                1135                1140

Ala Ala  Arg Pro Ala Gly Ala  Thr Leu Glu Arg Pro  Lys Thr Leu
    1145                1150                1155

Ser Pro  Gly Lys Asn Gly Val  Val Lys Asp Val Phe  Ala Phe Gly
    1160                1165                1170

Gly Ala  Val Glu Asn Pro Glu  Tyr Leu Thr Pro Gln  Gly Gly Ala
    1175                1180                1185
```

-continued

```
Ala Pro  Gln Pro His Pro Pro  Pro Ala Phe Ser Pro  Ala Phe Asp
    1190                 1195                 1200

Asn Leu  Tyr Tyr Trp Asp Gln  Asp Pro Pro Glu Arg  Gly Ala Pro
    1205                 1210                 1215

Pro Ser  Thr Phe Lys Gly Thr  Pro Thr Ala Glu Asn  Pro Glu Tyr
    1220                 1225                 1230

Leu Gly  Leu Asp Val Pro Val
    1235                 1240


<210> SEQ ID NO 5
<211> LENGTH: 4889
<212> TYPE: DNA
<213> ORGANISM: Homo sapiens

<400> SEQUENCE: 5

aagttcctgt gttctttatt ctactctccg ctgaagtcca cacagtttaa attaaagttc     60

ccggattttt gtgggcgcct gccccgcccc tcgtcccccct gctgtgtcca tatatcgagg    120

cgatagggtt aagggaaggc ggacgcctga tgggttaatg agcaaactga agtgttttcc    180

atgatctttt ttgagtcgca attgaagtac cacctcccga gggtgattgc ttccccatgc    240

ggggtagaac ctttgctgtc ctgttcacca ctctacctcc agcacagaat ttggcttatg    300

cctactcaat gtgaagatga tgaggatgaa aacctttgtg atgatccact tccacttaat    360

gaatggtggc aaagcaaagc tatattcaag accacatgca aagctactcc ctgagcaaag    420

agtcacagat aaaacggggg caccagtaga atggccagga caaacgcagt gcagcacaga    480

gactcagacc ctggcagcca tgcctgcgca ggcagtgatg agagtgacat gtactgttgt    540

ggacatgcac aaaagtgagt gtgcaccggc acagacatga agctgcggct ccctgccagt    600

cccgagaccc acctggacat gctccgccac ctctaccagg gctgccaggt ggtgcaggga    660

aacctggaac tcacctacct gcccaccaat gccagcctgt ccttcctgca ggatatccag    720

gaggtgcagg gctacgtgct catcgctcac aaccaagtga ggcaggtccc actgcagagg    780

ctgcggattg tgcgaggcac ccagctcttt gaggacaact atgccctggc cgtgctagac    840

aatggagacc cgctgaacaa taccacccct gtcacagggg cctccccagg aggcctgcgg    900

gagctgcagc ttcgaagcct cacagagatc ttgaaaggag ggtcttgat ccagcggaac    960

ccccagctct gctaccagga cacgattttg tggaaggaca tcttccacaa gaacaaccag   1020

ctggctctca cactgataga caccaaccgc tctcgggcct gccacccctg ttctccgatg   1080

tgtaagggct cccgctgctg gggagagagt tctgaggatt gtcagagcct gacgcgcact   1140

gtctgtgccg gtggctgtgc ccgctgcaag gggccactgc ccactgactg ctgccatgag   1200

cagtgtgctg ccggctgcac gggccccaag cactctgact gcctggcctg cctccacttc   1260

aaccacagtg gcatctgtga gctgcactgc ccagccctgg tcacctacaa cacagacacg   1320

tttgagtcca tgcccaatcc cgagggccgg tatacattcg gcgccagctg tgtgactgcc   1380

tgtccctaca actacctttc tacggacgtg ggatcctgca ccctcgtctg ccccctgcac   1440

aaccaagagg tgacagcaga ggatggaaca cagcggtgtg agaagtgcag caagccctgt   1500

gcccgagtgt gctatggtct gggcatggag cacttgcgag aggtgagggc agttaccagt   1560

gccaatatcc aggagtttgc tggctgcaag aagatctttg ggagcctggc atttctgccg   1620

gagagctttg atggggaccc agcctccaac actgccccgc tccagccaga gcagctccaa   1680

gtgtttgaga ctctggaaga gatcacaggt tacctataca tctcagcatg gccggacagc   1740

ctgcctgacc tcagcgtctt ccagaacctg caagtaatcc ggggacgaat tctgcacaat   1800
```

```
ggcgcctact cgctgaccct gcaagggctg ggcatcagct ggctggggct gcgctcactg   1860
agggaactgg gcagtggact ggccctcatc caccataaca cccacctctg cttcgtgcac   1920
acggtgccct gggaccagct ctttcggaac ccgcaccaag ctctgctcca cactgccaac   1980
cggccagagg acgagtgtgt gggcgagggc ctggcctgcc accagctgtg cgcccgaggg   2040
cactgctggg gtccagggcc cacccagtgt gtcaactgca gccagttcct tcggggccag   2100
gagtgcgtgg aggaatgccg agtactgcag gggctcccca gggagtatgt gaatgccagg   2160
cactgtttgc cgtgccaccc tgagtgtcag ccccagaatg gctcagtgac ctgttttgga   2220
ccggaggctg accagtgtgt ggcctgtgcc cactataagg accctccctt ctgcgtggcc   2280
cgctgcccca gcggtgtgaa acctgacctc tcctacatgc ccatctggaa gtttccagat   2340
gaggagggcg catgccagcc ttgccccatc aactgcaccc actcctgtgt ggacctggat   2400
gacaagggct gccccgccga gcagagagcc agccctctga cgtccatcat ctctgcggtg   2460
gttggcattc tgctggtcgt ggtcttgggg gtggtctttg ggatcctcat caagcgacgg   2520
cagcagaaga tccggaagta cacgatgcgg agactgctgc aggaaacgga gctggtggag   2580
ccgctgacac ctagcggagc gatgcccaac caggcgcaga tgcggatcct gaaagagacg   2640
gagctgagga aggtgaaggt gcttggatct ggcgcttttg gcacagtcta caagggcatc   2700
tggatccctg atggggagaa tgtgaaaatt ccagtggcca tcaaagtgtt gagggaaaac   2760
acatccccca aagccaacaa agaaatctta gacgaagcat acgtgatggc tggtgtgggc   2820
tccccatatg tctcccgcct tctgggcatc tgcctgacat ccacggtgca gctggtgaca   2880
cagcttatgc cctatggctg cctcttagac catgtccggg aaaaccgcgg acgcctgggc   2940
tcccaggacc tgctgaactg gtgtatgcag attgccaagg ggatgagcta cctggaggat   3000
gtgcggctcg tacacaggga cttggccgct cggaacgtgc tggtcaagag tcccaaccat   3060
gtcaaaatta cagacttcgg gctggctcgg ctgctggaca ttgacgagac agagtaccat   3120
gcagatgggg gcaaggtgcc catcaagtgg atggcgctgg agtccattct ccgccggcgg   3180
ttcacccacc agagtgatgt gtggagttat ggtgtgactg tgtgggagct gatgactttt   3240
ggggccaaac cttacgatgg gatcccagcc cgggagatcc ctgacctgct ggaaaagggg   3300
gagcggctgc cccagccccc catctgcacc attgatgtct acatgatcat ggtcaaatgt   3360
tggatgattg actctgaatg tcggccaaga ttccgggagt tggtgtctga attctcccgc   3420
atggccaggg acccccagcg ctttgtggtc atccagaatg aggacttggg cccagccagt   3480
cccttggaca gcaccttcta ccgctcactg ctggaggacg atgacatggg ggacctggtg   3540
gatgctgagg agtatctggt accccagcag ggcttcttct gtccagaccc tgccccgggc   3600
gctgggggca tggtccacca caggcaccgc agctcatcta ccaggagtgg cggtggggac   3660
ctgacactag ggctggagcc ctctgaagag gaggccccca ggtctccact ggcaccctcc   3720
gaaggggctg gctccgatgt atttgatggt gacctgggaa tgggggcagc caaggggctg   3780
caaagcctcc ccacacatga ccccagccct ctacagcggt acagtgagga ccccacagta   3840
cccctgccct ctgagactga tggctacgtt gccccccctga cctgcagccc ccagcctgaa   3900
tatgtgaacc agccagatgt tcggccccag ccccccttcgc cccgagaggg ccctctgcct   3960
gctgcccgac ctgctggtgc cactctggaa aggcccaaga ctctctcccc agggaagaat   4020
ggggtcgtca aagacgtttt tgcctttggg ggtgccgtgg agaaccccga gtacttgaca   4080
ccccagggag gagctgcccc tcagccccac cctcctcctg ccttcagccc agccttcgac   4140
```

-continued

```
aacctctatt actgggacca ggacccacca gagcgggggg ctccacccag caccttcaaa   4200

gggacaccta cggcagagaa cccagagtac ctgggtctgg acgtgccagt gtgaaccaga   4260

aggccaagtc cgcagaagcc ctgatgtgtc ctcagggagc agggaaggcc tgacttctgc   4320

tggcatcaag aggtgggagg gccctccgac cacttccagg ggaacctgcc atgccaggaa   4380

cctgtcctaa ggaaccttcc ttcctgcttg agttcccaga tggctggaag gggtccagcc   4440

tcgttggaag aggaacagca ctggggagtc tttgtggatt ctgaggccct gcccaatgag   4500

actctagggt ccagtggatg ccacagccca gcttggccct ttccttccag atcctgggta   4560

ctgaaagcct tagggaagct ggcctgagag gggaagcggc cctaagggag tgtctaagaa   4620

caaaagcgac ccattcagag actgtccctg aaacctagta ctgcccccca tgaggaagga   4680

acagcaatgg tgtcagtatc caggctttgt acagagtgct ttctgttta gtttttactt    4740

tttttgtttt gtttttttaa agatgaaata aagacccagg gggagaatgg gtgttgtatg   4800

gggaggcaag tgtggggggt ccttctccac acccactttg tccatttgca aatatatttt   4860

ggaaaacagc taaaaaaaaa aaaaaaaaa                                     4889


<210> SEQ ID NO 6
<211> LENGTH: 1225
<212> TYPE: PRT
<213> ORGANISM: Homo sapiens

<400> SEQUENCE: 6

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240
```

-continued

```
Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
```

```
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe  Phe Cys Pro Asp Pro  Ala Pro Gly
        995                 1000                1005

Ala Gly  Gly Met Val His His  Arg His Arg Ser Ser  Ser Thr Arg
    1010                1015                1020

Ser Gly  Gly Gly Asp Leu Thr  Leu Gly Leu Glu Pro  Ser Glu Glu
    1025                1030                1035

Glu Ala  Pro Arg Ser Pro Leu  Ala Pro Ser Glu Gly  Ala Gly Ser
    1040                1045                1050

Asp Val  Phe Asp Gly Asp Leu  Gly Met Gly Ala Ala  Lys Gly Leu
    1055                1060                1065

Gln Ser  Leu Pro Thr His Asp  Pro Ser Pro Leu Gln  Arg Tyr Ser
    1070                1075                1080
```

-continued

```
Glu Asp  Pro Thr Val Pro Leu  Pro Ser Glu Thr Asp  Gly Tyr Val
    1085                 1090                 1095

Ala Pro  Leu Thr Cys Ser Pro  Gln Pro Glu Tyr Val  Asn Gln Pro
    1100                 1105                 1110

Asp Val  Arg Pro Gln Pro Pro  Ser Pro Arg Glu Gly  Pro Leu Pro
    1115                 1120                 1125

Ala Ala  Arg Pro Ala Gly Ala  Thr Leu Glu Arg Pro  Lys Thr Leu
    1130                 1135                 1140

Ser Pro  Gly Lys Asn Gly Val  Val Lys Asp Val Phe  Ala Phe Gly
    1145                 1150                 1155

Gly Ala  Val Glu Asn Pro Glu  Tyr Leu Thr Pro Gln  Gly Gly Ala
    1160                 1165                 1170

Ala Pro  Gln Pro His Pro Pro  Pro Ala Phe Ser Pro  Ala Phe Asp
    1175                 1180                 1185

Asn Leu  Tyr Tyr Trp Asp Gln  Asp Pro Pro Glu Arg  Gly Ala Pro
    1190                 1195                 1200

Pro Ser  Thr Phe Lys Gly Thr  Pro Thr Ala Glu Asn  Pro Glu Tyr
    1205                 1210                 1215

Leu Gly  Leu Asp Val Pro Val
    1220                 1225
```